United States Patent
Abe et al.

(10) Patent No.: US 10,000,492 B2
(45) Date of Patent: Jun. 19, 2018

(54) PROCESS FOR PRODUCING DIAZABICYCLOOCTANE DERIVATIVE

(71) Applicant: MEIJI SEIKA PHARMA CO., LTD., Chuo-ku, Tokyo (JP)

(72) Inventors: Takao Abe, Kanagawa (JP); Takeshi Furuuchi, Kanagawa (JP); Yoshiaki Sakamaki, Kanagawa (JP); Nakako Mitsuhashi, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days. days.

(21) Appl. No.: 15/613,620

(22) Filed: Jun. 5, 2017

(65) Prior Publication Data
US 2017/0283415 A1 Oct. 5, 2017

Related U.S. Application Data

(62) Division of application No. 15/023,976, filed as application No. PCT/JP2014/075203 on Sep. 24, 2014.

(30) Foreign Application Priority Data

Sep. 24, 2013 (JP) ................. 2013-197110

(51) Int. Cl.
*C07D 471/08* (2006.01)
*C07D 401/12* (2006.01)
*C07D 211/60* (2006.01)

(52) U.S. Cl.
CPC .......... *C07D 471/08* (2013.01); *C07D 211/60* (2013.01); *C07D 401/12* (2013.01); *Y02P 20/55* (2015.11)

(58) Field of Classification Search
CPC .................................................. C07D 471/08
See application file for complete search history.

(56) References Cited

U.S. PATENT DOCUMENTS

| | | |
|---|---|---|
| 5,286,856 A | 2/1994 | Kaneko et al. |
| 5,424,069 A | 6/1995 | Kaneko et al. |
| 6,111,098 A | 8/2000 | Inoue et al. |
| 7,112,592 B2 | 9/2006 | Lampilas et al. |
| 7,612,087 B2 | 11/2009 | Aszodi et al. |
| 7,638,529 B2 | 12/2009 | Lampilas et al. |
| 7,732,610 B2 | 6/2010 | Lampilas et al. |
| 8,178,554 B2 | 5/2012 | Lampilas et al. |
| 8,288,553 B2 | 10/2012 | Priour et al. |
| 8,471,025 B2 | 6/2013 | Dedhiya et al. |
| 8,487,093 B2 | 7/2013 | Blizzard et al. |
| 8,772,490 B2 | 7/2014 | Abe et al. |

(Continued)

FOREIGN PATENT DOCUMENTS

| | | |
|---|---|---|
| EP | 01213595 | 3/1987 |
| EP | 0533149 A1 | 3/1993 |

(Continued)

OTHER PUBLICATIONS

Japanese Office Action dated Sep. 12, 2017 which issued in Japanese Application No. 2014-518712.
In edited by Chemical Society of Japan, "4th Edition Experimental Science Lecture 1 basic operation I", The Maruzen Co., Ltd.: pp. 184-189.
Brown et al, "Some Active Derivatives of Penicillin", Applied Microbiology 1969, vol. 17, No. 3, pp. 339-343.
Flow of research of Ryuichi Kato and optical isomerism medicine, Time Signal Company, Oct. 1, 1987, 29th volume, No. 10: pp. 2039-2042.

(Continued)

*Primary Examiner* — Noble E Jarrell
*Assistant Examiner* — John S Kenyon
(74) *Attorney, Agent, or Firm* — Holtz, Holtz & Volek PC

(57) ABSTRACT

A process for producing a compound represented by a Formula (III), including reacting a compound of the following formula

I

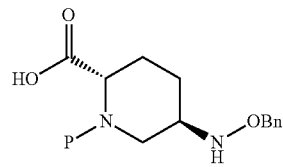

with a compound selected from the group consisting of 1-hydroxypyrrolidine-2,5-dione, 2-hydroxy-3a,4,7,7a-tetrahydro-1H-isoindol-1,3(2H)-dione, 2-hydroxyhexahydro-1H-isoindol-1,3(2H)-dione and 4-hydroxy-4-azatricyclo[5.2.1.0$^{2,6}$]dec-8-ene-3,5-dione, carrying out a carbonylation to obtain a compound of the following formula

II

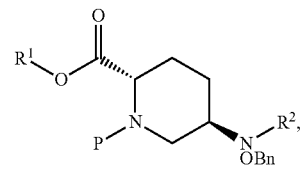

removing the NH protecting group P and treating the resultant compound with a base to produce a compound represented by the following formula

III

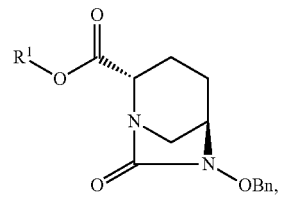

wherein OBn is benzyloxy and R$^2$ is hydrogen, ClCO— or Cl$_3$COCO—.

12 Claims, No Drawings

(56) References Cited

U.S. PATENT DOCUMENTS

| | | |
|---|---|---|
| 8,796,257 B2 | 8/2014 | Maiti et al. |
| 8,822,450 B2 | 9/2014 | Patel et al. |
| 8,829,191 B2 | 9/2014 | Ronsheim et al. |
| 8,835,455 B2 | 9/2014 | Dedhiya et al. |
| 8,877,743 B2 | 11/2014 | Maiti et al. |
| 8,969,566 B2 | 3/2015 | Ronsheim et al. |
| 9,006,230 B2 | 4/2015 | Bhagwat et al. |
| 9,035,062 B2 | 5/2015 | Abe et al. |
| 9,062,053 B2 | 6/2015 | Dedhiya et al. |
| 9,181,250 B2 | 11/2015 | Abe et al. |
| 9,284,273 B2 | 3/2016 | Abe et al. |
| 9,284,314 B2 | 3/2016 | Ronsheim et al. |
| 2003/0199541 A1 | 10/2003 | Lampilas et al. |
| 2003/0220521 A1 | 11/2003 | Reitz et al. |
| 2005/0020572 A1 | 1/2005 | Aszodi et al. |
| 2005/0245505 A1 | 11/2005 | Aszodi et al. |
| 2006/0046995 A1 | 3/2006 | Lampilas et al. |
| 2006/0189652 A1 | 8/2006 | Lampilas et al. |
| 2007/0299108 A1 | 12/2007 | Aszodi et al. |
| 2009/0215747 A1 | 8/2009 | Aszodi et al. |
| 2010/0048528 A1 | 2/2010 | Aszodi et al. |
| 2010/0087648 A1 | 4/2010 | Lampilas et al. |
| 2010/0197928 A1 | 8/2010 | Priour et al. |
| 2011/0021772 A1 | 1/2011 | Lampilas et al. |
| 2011/0046102 A1 | 2/2011 | Ledoussal et al. |
| 2011/0152311 A1 | 6/2011 | Dedhiya et al. |
| 2011/0213147 A1 | 9/2011 | Lampilas et al. |
| 2011/0245254 A1 | 10/2011 | Aszodi et al. |
| 2011/0294777 A1 | 12/2011 | Blizzard et al. |
| 2012/0053350 A1 | 3/2012 | Mangion et al. |
| 2013/0012712 A1 | 1/2013 | Priour et al. |
| 2013/0225554 A1 | 8/2013 | Maiti et al. |
| 2013/0267480 A1 | 10/2013 | Dedhiya et al. |
| 2013/0274475 A1 | 10/2013 | Mangion et al. |
| 2013/0281359 A1 | 10/2013 | Maiti et al. |
| 2014/0221341 A1 | 8/2014 | Maiti et al. |
| 2014/0288051 A1 | 9/2014 | Maiti et al. |
| 2014/0303375 A1 | 10/2014 | Abe et al. |
| 2015/0239840 A1 | 8/2015 | Abe et al. |
| 2015/0246920 A1 | 9/2015 | Dedhiya et al. |
| 2016/0024090 A1 | 1/2016 | Abe et al. |
| 2016/0137645 A1 | 5/2016 | Abe et al. |
| 2016/0264573 A1 | 9/2016 | Abe |
| 2016/0272641 A1 | 9/2016 | Abe et al. |
| 2017/0233393 A1 | 8/2017 | Abe et al. |

FOREIGN PATENT DOCUMENTS

| | | |
|---|---|---|
| GB | 1589317 A | 5/1981 |
| JP | 60019759 B2 | 5/1985 |
| JP | 2843444 B2 | 1/1990 |
| JP | 03074643 B2 | 11/1991 |
| JP | 2767171 B2 | 6/1998 |
| JP | 2004505088 A | 2/2004 |
| JP | 2005518333 A | 6/2005 |
| JP | 2005523897 A | 8/2005 |
| JP | 2010138206 A | 6/2010 |
| JP | 1515704 B2 | 8/2010 |
| JP | 2010539147 A | 12/2010 |
| JP | 2011510012 A | 3/2011 |
| JP | 2011518871 A | 6/2011 |
| JP | 2011207900 A | 10/2011 |
| JP | 2012504593 A | 2/2012 |
| JP | 5038509 B2 | 10/2012 |
| WO | 9529913 A1 | 11/1995 |
| WO | 0210172 A1 | 2/2002 |
| WO | 02100860 A2 | 12/2002 |
| WO | 03063864 A2 | 8/2003 |
| WO | 2009090320 A1 | 7/2009 |
| WO | 2009091856 A2 | 7/2009 |
| WO | 2009133442 A1 | 11/2009 |
| WO | 2010038115 A1 | 4/2010 |
| WO | 2010126820 A2 | 11/2010 |
| WO | 2011042560 A1 | 4/2011 |
| WO | 2012086241 A1 | 6/2012 |
| WO | 2012172368 A1 | 12/2012 |
| WO | 2013030735 A1 | 3/2013 |
| WO | 2013038330 A1 | 3/2013 |
| WO | 2013180197 A1 | 12/2013 |

OTHER PUBLICATIONS

International Search Report (ISR) dated Nov. 18, 2014 issued in International Application No. PCT/JP2014/075203.

Mangion et al, "A Concise Synthesis of a β-Lactamase Inhibitor", Organic Letters, 2011, vol. 13, No. 20, pp. 5480-5483.

Noriaki Hirayama, Yuki Kagobutsu Kessho Sakusei Handbook—Genri to Know-how-, Maruzen Co., Ltd., Jul. 25, 2008, pp. 57-84.

Baldwin, et al. "A Novel Entry to *Carbenoid* Species via β-Ketosulfoxonium Ylides", Journal of the Chemical Society, Chemical Communications, 1993, pp. 1434-1435.

Caira, "Crystalline Polymorphism of Organic Compounds", Topics in Current Chemistry, Springer, Berlin, DE, vol. 198, Jan. 1, 1998: pp. 163-208.

Cerfontain, et al., "Sulfur Trioxide", Encyclopedia of Reagents for Organic Synthesis, vol. 7, edited by Leo A. Paquette, 1995, John Wiley and Sons, pp. 4699-4702.

Dolence, et al., "Synthesis and Siderophore Activity of Albomycin-like Peptides Derived from N5-Acetyl-N5-hydroxy-L-ornithine", Journal of Medicinal Chemistry, 1991, vol. 34, No. 3, pp. 956-968.

Freed, et al., "Synthesis of 5-Ketopipecolic Acid from Glutamic Acid", The Journal of Organic Chemistry, Dec. 1960, vol. 25, No. 12, pp. 2105-2107.

Hirayama, "Organic compound crystal production handbooks", 2008: pp. 17-23, 37-40, 45-51, 57-65.

Jung, et al., "Diastereoselective synthesis of (2S,5S)- and (2S,5R)-N-benzyloxycarbonyl-5-hydroxypipecolic acids from trans-4-hydroxy-L-proline", Tetrahedron: Asymmetry 17 (2006), pp. 2479-2486.

King, et al., "The Chemistry of Extractives from Hardwoods. Part III. Baikiain, an Amino-acid Present in Baikiaea plurijuga", Journal of the Chemical Society, 1950, pp. 3590-3597.

Knight, "N-Hydroxysuccinimide", Encyclopedia of Reagents for Organic Synthesis, vol. 4, Edited by Leo A. Paquette, 1995, John Wiley and Sons, pp. 2780-2781.

Mangion, et al., "Iridium-Catalyzed X-H Insertions of Sulfoxonium Ylides", Organic Letters, 2009, vol. 11, No. 16, pp. 3566-3569.

McIntosh, "Sulfur Troxide-1, 4-Dioxane", Encyclopedia of Reagents for Organic Synthesis, vol. 7, Edited by Leo A. Paquette, 1995, John Wiley and Sons, pp. 4702-4703.

Nohira, "Agricultural chemicals, medicine, optically active substance, The organic industrial chemistry", Asakura Publishing Co.,Ltd., Jan. 20, 1989, 1st printing: pp. 20, 21.

Pettit, et al., "8-Hydroxy-5-trifluoromethylquinoline", Journal of Chemical Society (1954), 3852-3854.

Teruzo, "Solvent Handbook", Incorporated Company Kodansha, 1985: pp. 47-51.

Tidwell, "Sulfur Trioxide-Pyridine", Encyclopedia of Reagents for Organic Synthesis, vol. 7, Edited by Leo A Paquette, 1995, John Wiley and Sons, pp. 4703-4704.

Witkop, et al., "The Configuration of 5-Hydroxypipecolic Acid from Dates", Journal of the American Chemical Society, Jan. 5, 1957, vol. 79, No. 1, pp. 192-197.

Yamanaka, et al., "The Preparation, bioactive and use of an optically active substance, Quarterly Chemistry Survey—Separation of an optical isomer", Japan Scientific Societies Press, Inc., Jun. 10, 1989, No. 6: pp. 8-9,124, 212-213.

U.S. Appl. No. 15/532,281, filed Jun. 1, 2017.

Rowe, "Handbook of Pharmaceutical Excipients", 5th Edition, 2006.

Walker, "The Management of Chemical Process Development in the Pharmaceutical Industry", 2008, John Wiley & Sons, p. 186.

Korey, et al., "Effects of Excipients on the Crystallization of Pharmaceutical Compounds During Lyophilization", Jounral of Parenteral Science & Technology, vol. 43, No. 2, Mar.-Apr. 1989, pp. 80-83.

PROCESS FOR PRODUCING DIAZABICYCLOOCTANE DERIVATIVE

CROSS-REFERENCE TO RELATED APPLICATIONS

This application is a Divisional application of application Ser. No. 15/023,976, filed Mar. 22, 2016, which is a U.S. national phase application of International application PCT/JP2014/075203, filed Sep. 24, 2014. The entire contents of each of application Ser. No. 15/023,976 and PCT/JP2014/075203 are incorporated herein by reference.

TECHNICAL FIELD

The present invention relates to a process for producing a diazabicyclooctane derivative represented by Formula (IV) and intermediates thereof.

BACKGROUND ART

Japanese Patent No. 4515704 (Patent Document 1) indicates a novel heterocyclic compound, a production process thereof, and the medicinal use thereof, and discloses as a typical example of a compound thereof trans-7-oxo-6-(sulfooxy)-1,6-diazabicyclo[3.2.1]octane-2-carboxamide (NXL104). Production processes of an intermediate in the form of a specific piperidine derivative are also indicated in Japanese Unexamined Patent Publication No. 2010-138206 (Patent Document 2) and Japanese Unexamined Patent Application Publication (Translation of PCT Application) No. 2010-539147 (Patent Document 3), while a production process of NXL104 and crystalline forms thereof is disclosed in International Publication No. WO 2011/042560 (Patent Document 4).

In addition, Japanese Patent No. 5038509 (Patent Document 5) indicates (2S,5R)-7-oxo-N-(piperidin-4-yl)-6-(sulfooxy)-1,6-diazabicyclo[3.2.1]octane-2-carboxamide (MK-7655), while a production process of a specific piperidine derivative and MK7655 are disclosed in Japanese Unexamined Patent Publication No. 2011-207900 (Patent Document 6) and International Publication No. WO 2010/126820 (Patent Document 7).

The inventors of the present invention also disclose novel diazabicyclooctane derivatives represented by Formulae (IV), (V) and (VI) and a production process thereof, and particularly a process for producing a compound represented by the following Formula (VI-1) in the following Scheme 1 in Japanese Patent Application No. 2012-122603 (Patent Document 8):

Scheme 1

[Chemical Formula 1]

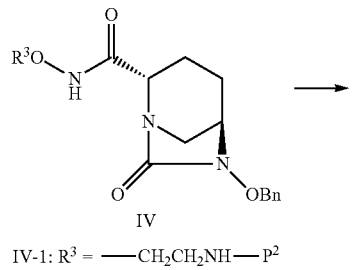

IV-1: $R^3$ = —$CH_2CH_2NH$—$P^2$

-continued

V

IV-1: $R^3$ = —$CH_2CH_2NH$—$P^2$

VI

IV-1: $R^3$ = —$CH_2CH_2NH_2$ (wherein OBn is benzyloxy, $P^2$ is tert-butoxycarbonyl (Boc) or benzyloxycarbonyl (Cbz), and $R^3$ is same as will be subsequently described).

PRIOR ART DOCUMENTS

Patent Documents

Patent Document 1: Japanese Patent No. 4515704 specification
Patent Document 2: Japanese Unexamined Patent Publication No. 2010-138206 specification
Patent Document 3: Japanese Unexamined Patent Application Publication (Translation of PCT Application) No. 2010-539147 specification
Patent Document 4: International Publication No. WO 2011/042560
Patent Document 5: Japanese Patent No. 5038509 specification
Patent Document 6: Japanese Unexamined Patent Publication No. 2011-207900 specification
Patent Document 7: International Publication No. WO 2010/126820
Patent Document 8: Japanese Patent Application No. 2012-122603 specification

SUMMARY OF THE INVENTION

Problems to be Solved by the Invention

The inventors of the present invention previously disclosed a process that proceeds from a compound represented by Formula (3) through a compound represented by Formula (4) and a process that proceeds from a compound represented by Formula (5) through a compound represented by Formula (6) and a compound represented by Formula (7) in the following Scheme 2 as a process for producing the aforementioned compound represented by Formula (IV), and particularly a compound represented by Formula (IV-1), but during the course of studying a process for enlarging the production scale of the development candidate, the processes were shown to not necessarily be industrially optimal process for reasons that, in addition to the former having only a moderate yield when proceeding from a compound represented by Formula (2) to the compound represented by Formula (3) and from the compound represented by Formula (3) to the compound represented by Formula (4), synthesis of the compound represented by Formula (IV) from the compound represented by Formula (4) did not have a satisfactory yield due to low reactivity attributed to steric hindrance of the environment surrounding the carboxyl group as well as purification loss during removal of byproduct, while the latter had low yield from the compound represented by Formula (7) to the compound represented by Formula (IV), and results in increased production costs due to the introduction of an $R^3O$—NH side chain early in the process:

the compound represented by the aforementioned Formula (4), the desired compound was able to be obtained only in a moderate yield due to the low reactivity of the compound represented by Formula (4). Next, phosgenation, deprotection and then cyclization reaction were attempted on a compound represented by Formula (8) or a compound represented by Formula (9) in the following Scheme 3 as a preliminary study conducted for the purpose of obtaining the compound represented by Formula (IV) without proceeding from the compound represented by the aforementioned Formula (6) through the compound represented by Formula (7). As a result, although a compound represented by Formula (10) was able to be derived from the compound Scheme 2

[Chemical Formula 2]

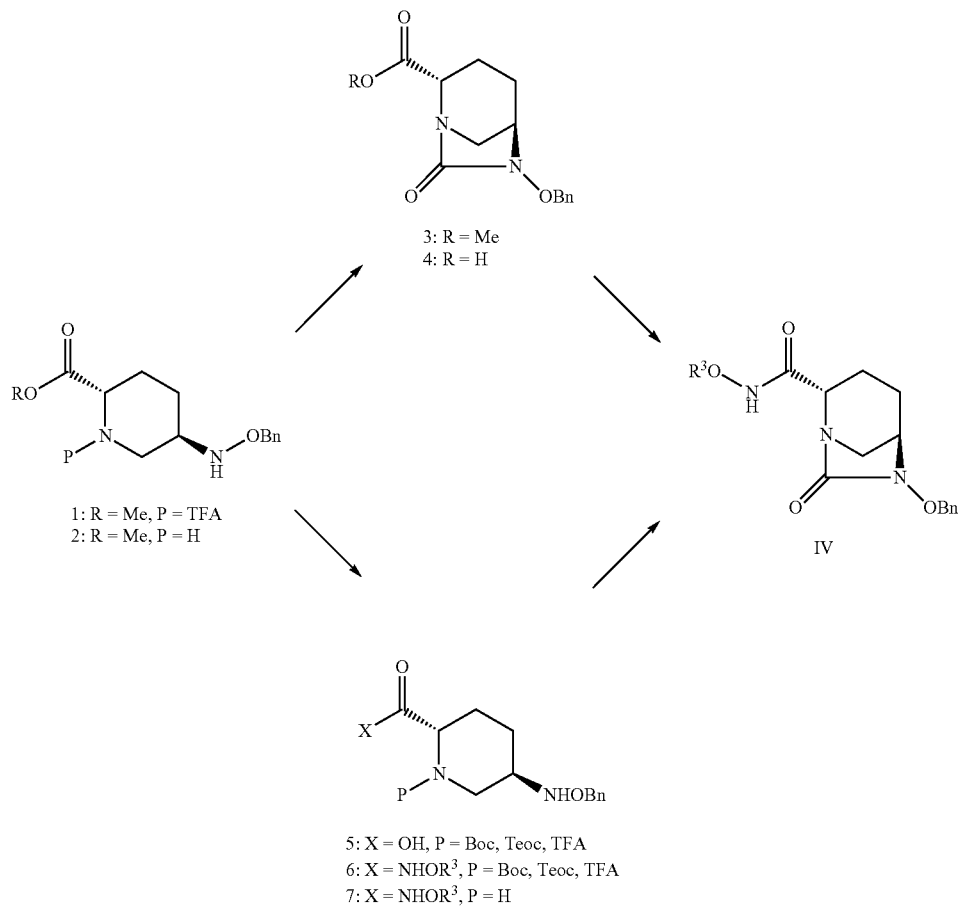

(wherein OBn is benzyloxy, TFA is 2,2,2-trifluoroacetyl, Boc is tert-butoxycarbonyl, Teoc is 2-trimethylsilylethoxycarbonyl, and $R^3$ is same as will be subsequently described).

While intramolecular ureation was attempted after using an active group as X of the compound represented by the aforementioned Formula (5) and deprotecting, the active group also ended up being removed under the conditions used for deprotection, or only a complex mixture was obtained due to the occurrence of decomposition caused by an intermolecular reaction occurring under the conditions of phosgenation. In addition, although an attempt was made to isolate an intermediate introduced with an active group from represented by Formula (8) without any problems without having to add an activating agent such as 4-dimethylaminopyridine during cyclization reaction, the desired compound represented by Formula (11) was indicated to be unable to be obtained at all from the compound represented by Formula (9).

With the foregoing in view, the inventors of the present invention conducted extensive studies on a novel and efficient process for producing a compound represented by the aforementioned Formula (IV) with the aim of developing a process for producing a compound represented by Formula (VI) industrially.

Scheme 3

[Chemical Formula 3]

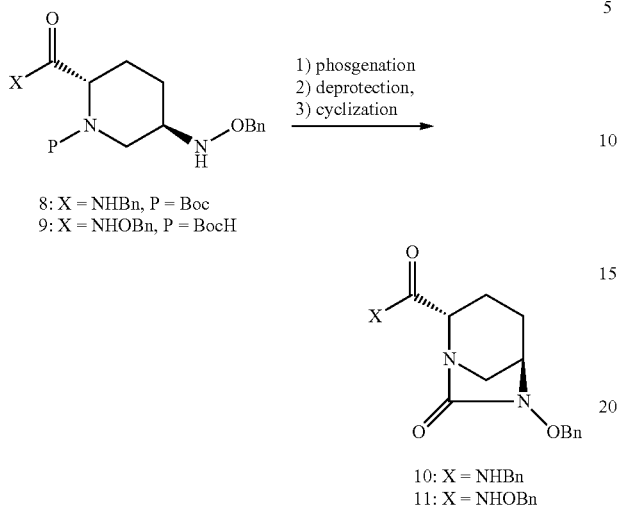

8: X = NHBn, P = Boc
9: X = NHOBn, P = BocH

10: X = NHBn
11: X = NHOBn (In the above formulas, OBn is benzyloxy, and Boc is tert-butoxycarbonyl.)

Means for Solving the Problems

The present inventors introduced various active groups employed in peptide synthesis for $R^1$ into the carboxyl group of a compound represented by Formula (I) of the following Scheme 4 instead of direct activation of the less reactive carboxyl group of the compound represented by the aforementioned Formula (4), and examined a synthetic process that goes through a compound represented by Formula (III) to a compound represented by Formula (IV). In particular, in the case of a compound having a 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2,6}$]dec-8-en-4-yl group as $R^1$ represented by Formula (II), the present inventors found that a protecting group P is selectively deprotected without having an effect on the active group under mildly acidic conditions following phosgenation, that the reaction subsequently proceeds continuously through the cyclization reaction by treating the reaction solution with a base, and that a compound represented by Formula (III) is obtained in a satisfactory yield. Moreover, the present inventors succeeded in deriving the compound represented by Formula (IV) without producing byproduct and in high yield by directly reacting the resulting compound represented by Formula (III) with $R^3ONH_2$ than the process that goes through the compound represented by the aforementioned Formula (4):

Scheme 4

[Chemical Formula 4]

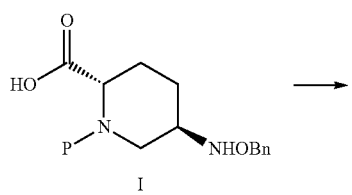

I (wherein P is an NH protecting group capable of being removed with an acid, $R^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2,6}$]dec-8-en-4-yl, $R^2$ is hydrogen, ClCO— or $Cl_3COCO$— and $R^3$ is same as will be subsequently described).

Namely, (1) the present invention relates to a process for producing a compound represented by the following Formula (IV):

[Chemical Formula 5]

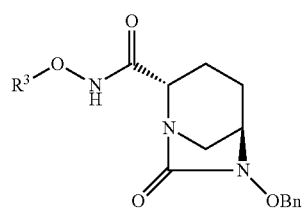

IV comprising: reacting a compound represented by general Formula (I):

[Chemical Formula 6]

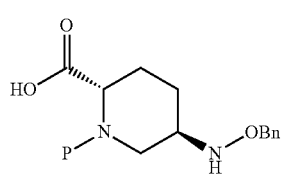

I with $R^1OH$ selected from 1-hydroxypyrrolidin-2,5-dione, 2-hydroxy-3a,4,7,7a-tetrahydro-1H-isoindol-1,3(2H)-dione, 2-hydroxyhexahydro-1H-isoindol-1,3(2H)-dione, and 4-hydroxy-4-azatricyclo[5.2.1.0$^{2,6}$]dec-8-ene-3,5-dione followed by allowing a carbonylation agent selected from phosgene, diphosgene and triphosgene to act thereon to obtain a compound represented by the following Formula (II):

[Chemical Formula 7]

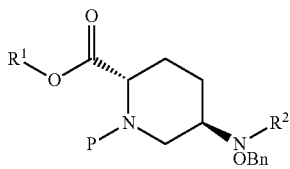

II removing a protecting group P and treating with a base to obtain a compound represented by the following Formula (III):

[Chemical Formula 8]

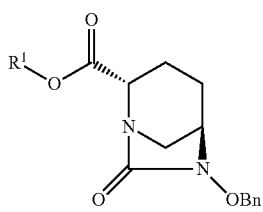

III and reacting with a compound: R$^3$ONH$_2$ (in the aforementioned Formulas (I), (II), (III) and (IV), OBn is benzyloxy, P is an NH protecting group capable of being removed with an acid, R$^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2,6}$]dec-8-en-4-yl, R$^2$ is hydrogen, ClCO— or Cl$_3$COCO—, R$^3$ is C$_{1-6}$ alkyl or heterocyclyl, or forms a 3- to 7-membered heterocyclic ring together with the adjacent —O—NH—. R$^3$ may be modified with 0 to 5 R$^4$, and R$^4$ may be consecutively substituted. Here, R$^4$ is C$_{1-6}$ alkyl, C$_{1-6}$ alkoxy, C$_{1-6}$ alkylsulfonyl, heterocyclyl, heterocyclylcarbonyl, R$^5$(R$^6$)N— or a protecting group. R$^5$ and R$^6$ are each independently hydrogen or C$_{1-6}$ alkyl or together form a 3- to 7-membered heterocyclic ring. Further, R$^3$, R$^5$ and R$^6$ can undergo ring closure at an arbitrary position).

In addition, (2) another aspect of the present invention relates to a process for producing a compound represented by Formula (IV), comprising: allowing a carbonylation agent selected from phosgene, diphosgene and triphosgene to act on a compound represented by the following Formula (II), wherein R$^2$ is hydrogen:

[Chemical Formula 9]

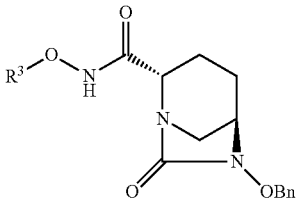

II followed by removing the protecting group P, treating with a base and further reacting with a compound: R$^3$ONH$_2$ to produce the compound represented by the following Formula (IV):

[Chemical Formula 10]

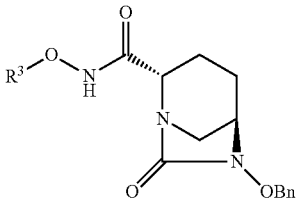

IV (in the aforementioned Formulas (II) and (IV), OBn, P, R$^1$, R$^2$ and R$^3$ are same as described above).

In addition, (3) another aspect of the present invention relates to the process described in (1) or (2) above, which proceeds through a compound represented by the Formula (I) or (II), wherein P is tert-butoxycarbonyl (Boc).

In addition, (4) another aspect of the present invention relates to the process described in any of (1) to (3) above, which proceeds through a compound represented by the Formula (II) or (III), wherein R$^1$ is 2,5-dioxopyrrolidin-1-yl.

In addition, (5) another aspect of the present invention relates to the process described in any of (1) to (3), which proceeds through a compound represented by the Formula (II) or (III), wherein R$^1$ is 1,3-dioxo-3a,4,7,7a-tetrahydro-1H-isoindol-2(3H)-yl.

In addition, (6) another aspect of the present invention relates to the process described in any of (1) to (3), which proceeds through a compound represented by the Formula (II) or (III), wherein R$^1$ is 1,3-dioxohexahydro-1H-isoindol-2(3H)-yl.

In addition, (7) another aspect of the present invention relates to the process described in any of (1) to (3) above, which proceeds through a compound represented by the Formula (II) or (III), wherein R$^1$ is 3,5-dioxo-4-azatricyclo[5.2.1.0$^{2,6}$]dec-8-en-4-yl.

In addition, (8) another aspect of the present invention relates to the process described in any of (1) to (7) above for producing a compound represented by the Formula (IV), wherein R$^3$ is selected from:
2-(tert-butoxycarbonylamino)ethyl;
2-((tert-butoxycarbonyl)(methyl)amino)ethyl;
2-((tert-butoxycarbonyl)(isopropyl)amino)ethyl;
2-(dimethylamino)ethyl;
(2S)-2-((tert-butoxycarbonyl)amino)propyl;
(2R)-2-((tert-butoxycarbonyl)amino)propyl;
3-((tert-butoxycarbonyl)amino)propyl;
(2S)-tert-butoxycarbonylazetidin-2-ylmethyl;
(2R)-tert-butoxycarbonylpyrrolidin-2-ylmethyl;
(3R)-tert-butoxycarbonylpiperidin-3-ylmethyl;
(3S)-tert-butoxycarbonylpyrrolidin-3-yl;
1-(tert-butoxycarbonyl)azetidin-3-yl;
2-(benzyloxycarbonylamino)ethyl;
2-((benzyloxycarbonyl)(methyl)amino)ethyl;
2-((benzyloxycarbonyl)(isopropyl)amino)ethyl;
(2S)-2-((benzyloxycarbonyl)amino)propyl;
(2R)-2-((benzyloxycarbonyl)amino)propyl;
3-((benzyloxycarbonyl)amino)propyl;
(2S)-benzyloxycarbonylazetidin-2-ylmethyl;
(2R)-benzyloxycarbonylpyrrolidin-2-ylmethyl;

(3R)-benzyloxycarbonylpiperidin-3-ylmethyl;
(3S)-benzyloxycarbonylpyrrolidin-3-yl; and
1-(benzyloxycarbonyl)azetidin-3-yl.

In addition, (9) another aspect of the present invention relates to the process described in any of (1) to (7) above for producing a compound represented by the following Formula (IV-1):

[Chemical Formula 11]

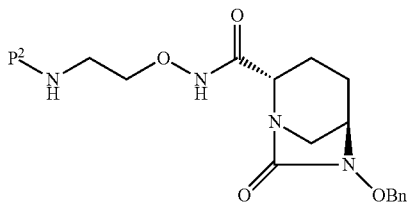

IV-1
IV-1-1: $P^2$ = Boc
IV-1-2: $P^2$ = Cbz (wherein $P^2$ is tert-butoxycarbonyl (Boc) or benzyloxycarbonyl (Cbz) and OBn is benzyloxy).

In addition, (10) another aspect of the present invention relates to the process described in any of (1) to (7) above for producing a compound represented by the following Formula (IV-1-1):

[Chemical Formula 12]

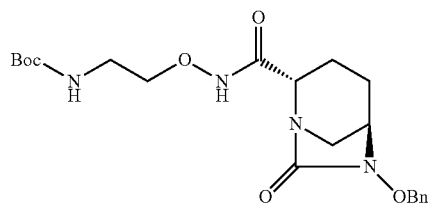

IV-1-1

(wherein Boc is tert-butoxycarbonyl and OBn is benzyloxy).

In addition, (11) another aspect of the present invention relates to a process for producing a compound represented by Formula (III), comprising: reacting a compound represented by the following Formula (I):

[Chemical Formula 13]

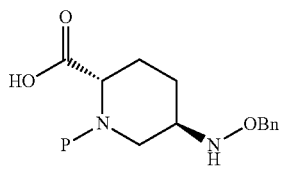

I with $R^1$OH selected from 1-hydroxypyrrolidin-2,5-dione, 2-hydroxy-3a,4,7,7a-tetrahydro-1H-isoindol-1,3(2H)-dione, 2-hydroxyhexahydro-1H-isoindol-1,3(2H)-dione, or 4-hydroxy-4-azatricyclo[5.2.1.0$^{2,6}$]dec-8-ene-3,5-dione to allow a carbonylating agent selected from phosgene, diphosgene and triphosgene to act thereon to obtain a compound represented by the following Formula (II):

[Chemical Formula 14]

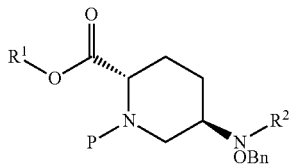

II removing the protecting group P and treating with a base to produce the compound represented by the following Formula (III):

[Chemical Formula 15]

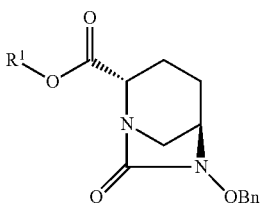

III (in the aforementioned Formulas (I), (II) and (III), OBn, P, $R^1$ and $R^2$ are same as described above).

In addition, (12) another aspect of the present invention relates to a process for producing a compound represented by Formula (III), comprising: allowing a carbonylating agent selected from phosgene, diphosgene and triphosgene to act on a compound represented by the following Formula (II), wherein $R^2$ is hydrogen:

[Chemical Formula 16]

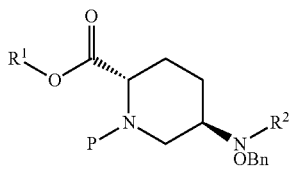

II followed by removing the protecting group P and treating with a base to produce the compound represented by the following Formula (III):

[Chemical Formula 17]

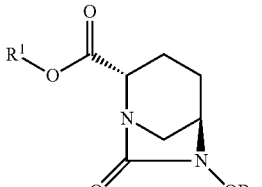

III (in the aforementioned Formulas (II) and (III), OBn, P, $R^1$ and $R^2$ are same as described above).

In addition, (13) another aspect of the present invention relates to the process described in (11) or (12) above, which proceeds through a compound represented by the Formula (I) or (II), wherein P is tert-butoxycarbonyl (Boc).

In addition, (14) another aspect of the present invention relates to the process described in any of (11) to (13) above for producing a compound represented by the Formula (III), wherein $R^1$ is 2,5-dioxypyrrolidin-1-yl.

In addition, (15) another aspect of the present invention relates to the process described in any of (11) to (13) above for producing a compound represented by the Formula (III), wherein $R^1$ is 1,3-dioxo-3a,4,7,7a-tetrahydro-1H-isoindol-2(3H)-yl.

In addition, (16) another aspect of the present invention relates to the process described in any of (11) to (13) above for producing a compound represented by the Formula (III), wherein $R^1$ is 1,3-dioxohexahydro-1H-isoindol-2(3H)-yl.

In addition, (17) another aspect of the present invention relates to the process described in any of (11) to (13) above for producing a compound represented by the Formula (III), wherein $R^1$ is 3,5-dioxo-4-azatricyclo[5.2.1.0$^{2,6}$]dec-8-en-4-yl.

In addition, (18) another aspect of the present invention relates to a compound represented by the following Formula (III-58):

[Chemical Formula 18]

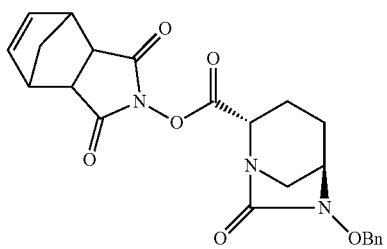

III-58

(wherein OBn is benzyloxy).

In addition, (19) another aspect of the present invention relates to a compound represented by the following Formula (III-59):

[Chemical Formula 19]

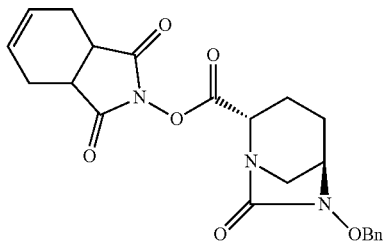

III-59

(wherein OBn is benzyloxy).

In addition, (20) another aspect of the present invention relates to a compound represented by the following Formula (III-60):

[Chemical Formula 20]

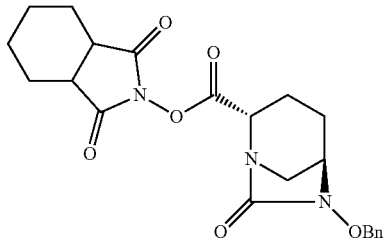

III-60

(wherein OBn is benzyloxy).

In addition, (21) another aspect of the present invention relates to a compound represented by the following Formula (II-30):

[Chemical Formula 21]

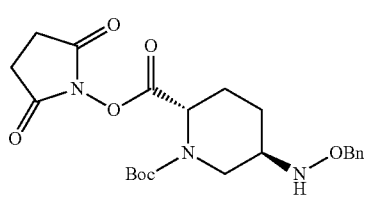

II-30

(wherein Boc is tert-butoxycarbonyl and OBn is benzyloxy).

In addition, (22) another aspect of the present invention relates to a compound represented by the following Formula (II-31):

[Chemical Formula 22]

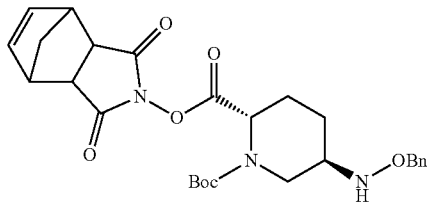

II-31

(wherein Boc is tert-butoxycarbonyl and OBn is benzyloxy).

In addition, (23) another aspect of the present invention relates to a compound represented by the following Formula (II-32):

[Chemical Formula 23]

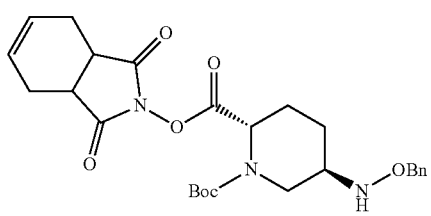

II-32

(wherein Boc is tert-butoxycarbonyl and OBn is benzyloxy).

In addition, (24) another aspect of the present invention relates to a compound represented by the following Formula (II-33):

[Chemical Formula 24]

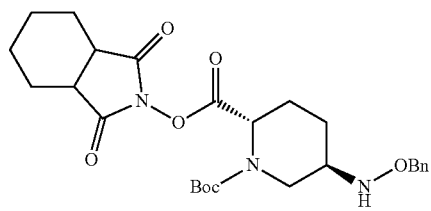

II-33

(wherein Boc is tert-butoxycarbonyl and OBn is benzyloxy).

Effects of the Invention

The present production process is a process for efficiently obtaining a compound represented by the aforementioned Formula (IV) both more easily and in higher yield than by going through a compound represented by Formula (2) to a compound represented by Formula (4) of the aforementioned Scheme 2. The carboxyl group of the compound represented by the aforementioned Formula (I) can be more easily modified than the carboxyl group of a compound represented by Formula (4). Intramolecular ureation of a compound represented by Formula (II) easily proceeds in higher yield than a compound represented by Formula (2). In the reaction between the carboxyl group of the compound represented by the aforementioned Formula (4) and the $R^3ONH_2$ group, although a large amount of byproducts were formed and a satisfactory yield was unable to be obtained due to steric hindrance of the environment surrounding the carboxyl group even if carried out using a commonly employed dehydration condensation agent or mixed acid anhydride method, since an intermediate in the form of a compound represented by the aforementioned Formula (III) has an active ester, it is a highly versatile compound that enables the compound represented by the aforementioned Formula (IV) to be derived more selectively and directly. In particular, instead of going through the compound represented by Formula (4), the compound represented by the aforementioned Formula (III-58) can be obtained in high yield by continuously synthesizing from the compound represented by Formula (I) that is quantitatively obtained from the compound represented by Formula (2) without isolating the compound represented by Formula (II) as indicated in the following Scheme 5, demonstrates storage stability equal to that of the compound represented by Formula (4), and allows the compound represented by Formula (IV), and particularly the compound represented by the following Formula (IV-1-1), to be obtained in high purity and high yield without forming byproduct simply by subjecting to extraction and washing treatment, thereby offering numerous advantages in terms of attempting to realize industrialization. The process for producing the compound represented by Formula (IV), and particularly the compound represented by Formula (IV-1-1), according to the present invention is highly useful as a production process suitable for commercialization of compounds represented by the aforementioned Formula (VI-1).

Scheme 5

[Chemical Formula 25]

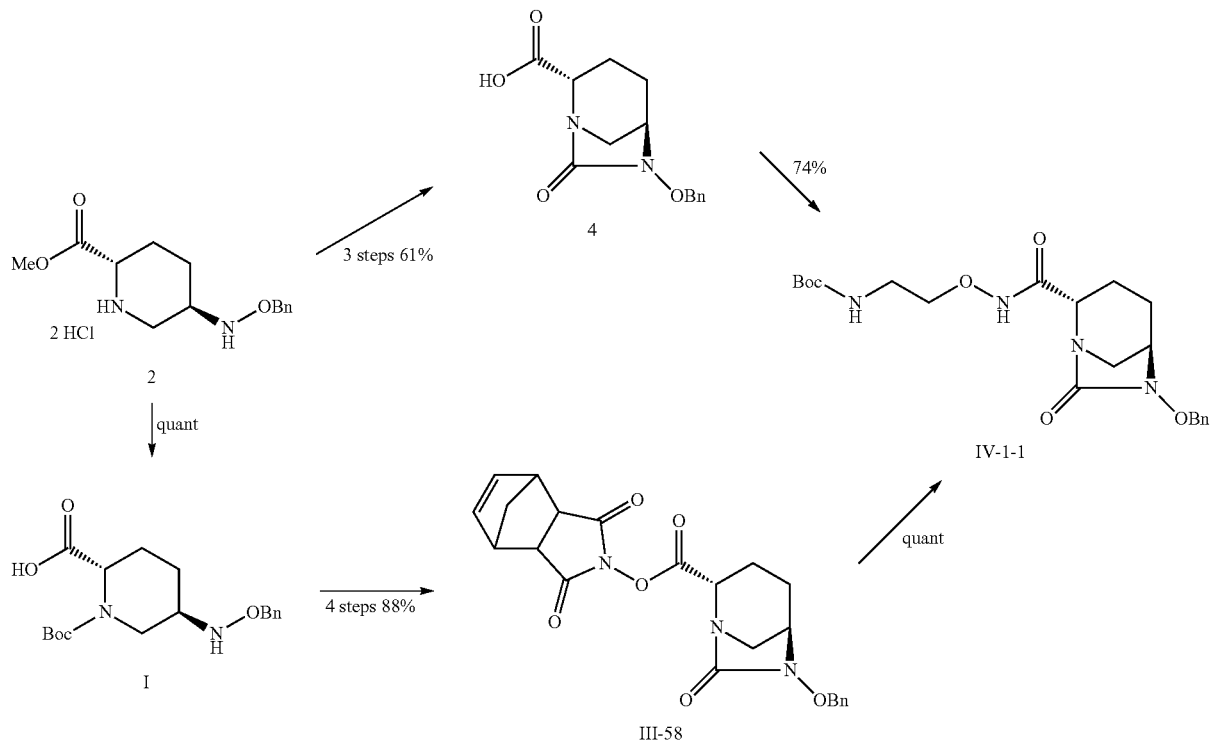

(In the above formulas, Boc is tert-butoxycarbonyl and OBn is benzyloxy.)

Mode For Carrying Out the Invention

As was previously described, the present invention provides a process for producing a diazabicyclooctane derivative represented by the following Formula (IV) and intermediates thereof:

[Chemical Formula 26]

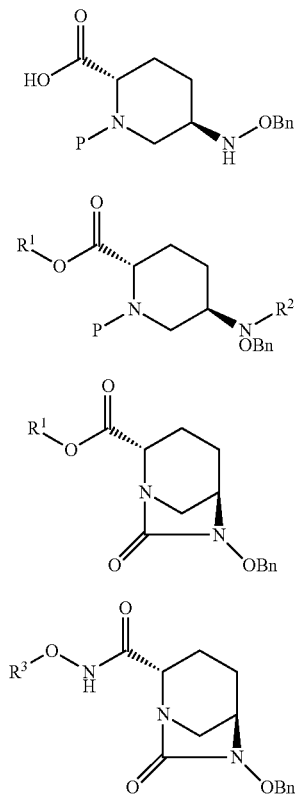

(in the aforementioned Formulas (I), (II), (III) and (IV), OBn is benzyloxy, P is an NH protecting group capable of being removed with an acid, $R^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2,6}$]dec-8-en-4-yl, $R^2$ is hydrogen, ClCO— or $Cl_3COCO$—, $R^3$ is $C_{1-6}$ alkyl or heterocyclyl, or forms a 3- to 7-membered heterocyclic ring together with the adjacent —O—NH—, $R^3$ may be modified with 0 to 5 $R^4$, $R^4$ may be consecutively substituted. Here, $R^4$ is $C_{1-6}$ alkyl, $C_{1-6}$ alkoxy, $C_{1-6}$ alkylsulfonyl, heterocyclyl, heterocyclylcarbonyl, $R^5(R^6)N$— or a protecting group. $R^5$ and $R^6$ each independently is hydrogen or $C_{1-6}$ alkyl or together forms a 3- to 7-membered heterocyclic ring. Further, $R^3$, $R^5$ and $R^6$ can undergo ring closure at an arbitrary position).

Although the following provides a detailed explanation of the process of the present invention for producing a diazabicyclooctane derivative represented by Formula (IV) and intermediates thereof, the present invention is not limited to the scope of the indicated specific examples thereof.

An "active group" and "active ester" refer to functional groups that fulfill the role of enhancing reaction yield and selectivity of the amine component by coupling to a carboxyl group.

"$C_{1-6}$ alkyl" refers to an alkyl group having 1 to 6 carbon atoms which may be linear, branched or cyclic. "$C_{1-6}$ alkoxy" refers to an alkoxy group having 1 to 6 carbon atoms which may be linear, branched or cyclic. "$C_{1-6}$ alkylsulfonyl" refers to a sulfonyl group coupled to an alkyl group having 1 to 6 carbon atoms wherein the alkyl moiety may be linear, branched or cyclic.

"Heterocyclyl" refers to a 3- to 7-membered monocyclic heterocyclic saturated ring or non-aromatic ring having a total of 1 to 3 heteroatoms selected from a nitrogen atom, oxygen atom and sulfur atom as ring constituents thereof. "Heterocyclylcarbonyl" refers to a carbonyl group coupled to the heterocyclyl.

"$R^5(R^6)N$—" refers to an amino substituted with $R^5$ and $R^6$, namely an amino, mono-$C_{1-6}$ alkylamino or di-$C_{1-6}$ alkylamino. Alternatively, in "$R^5(R^6)N$—", $R^5$ and $R^6$ may together form a 3- to 7-membered heterocyclic ring.

"Modified" with respect to $R^3$ refers to a hydrogen in $R^3$ being substituted with or connected to $R^4$.

"$R^3$ may be modified with 0 to 5 $R^4$, and $R^4$ may be consecutively substituted" means that $R^4$ that modifies $R^3$ may be further modified with $R^4$, and examples thereof include $R^3$—$(R^4)_{0-5}$, $R^3$—$(R^4$—$R^4{}_{0-4})$, $R^3$—$(R^4$—$R^4{}_{0-3})_2$, $R^3$—$(R^4$—$R^4{}_{0-2})_3$ and $R^3$—$(R^4$—$R^4{}_{0-1})_4$.

Specific examples of protecting groups include carbamate-type protecting groups and trialkylsilyl groups that are protecting groups of amino groups and hydroxyl groups as described in Protective Groups in Organic Synthesis (T. W. Greene et al., Wiley, New York (1999)), and preferable examples thereof include triisopropylsilyl (TIPS), tert-butyldimethylsilyl (TBDMS or TBS), tert-butoxycarbonyl (Boc), trimethylsilylethoxycarbonyl (Teoc), 4-methoxybenzyloxycarbonyl (PMZ, Moz), allyloxycarbonyl (Alloc), diphenylmethoxycarbonyl, 9-fluororenylmethoxycarbonyl (Fmoc) and benzyloxycarbonyl (Cbz, Z).

Specific examples of "$C_{1-6}$ alkyl" include $C_{1-6}$ alkyl groups such as a methyl, ethyl, propyl, isopropyl, butyl, tert-butyl, s-butyl, isobutyl, pentyl, 1,1-dimethylpropyl, 1,2-dimethylpropyl, neopentyl, 1-methylbutyl, 2-methylbutyl, isopentyl and hexyl group, $C_{3-6}$ cycloalkyl groups such as a cyclopropyl, cyclobutyl, cyclopentyl and cyclohexyl group, and methyl groups substituted with a $C_{3-5}$ cycloalkyl group such as a cyclopropylmethyl, cyclobutylmethyl or cyclopentylmethyl group, and preferably include methyl, ethyl, propyl, isopropyl, butyl, tert-butyl, cyclopropyl, cyclobutyl, cyclopropylmethyl and cyclobutylmethyl groups.

Specific examples of "$C_{1-6}$ alkoxy" include a variety of alkoxy having "$C_{1-6}$ alkyl" specifically illustrated above.

Specific examples of "$C_{1-6}$ alkylsulfonyl" include a variety of alkylsulfonyl having "$C_{1-6}$ alkyl" specifically illustrated above.

Specific examples of "heterocyclyl" groups include aziridine, oxirane, thiirane, azetidine, oxetane, thietane, pyrrolidine, tetrahydrofuran, tetrahydrothiophene, imidazolidine, oxazolidine, thiazolidine, pyrazolidine, piperidine, tetrahydro-2H-pyran, tetrahydro-2H-thiopyran, hexahydropyridazine, piperazine, morpholine, thiomorpholine, 1,2-oxazolidine, 1,3-oxazolidine, 1,2-oxazinane, 1,3-oxazinane, 1,4-dioxane, 1,2-thiazolidine, 1,3-thiazolidine, 1,2-thiazinane, 1,3-thiazinane, azepane, oxepane, thiepane, 1,4-diazepane, 1,4-oxazepane, 1,4-thiazepane, 1,2,5-triazepane, 1,4,5-oxadiazepane, 1,2,5-oxadiazepane, 1,4,5-thiadiazepane, 1,5,2-dioxazepane, 1,5,2-oxathiazepane, 3,4-dihydro-2H-pyrrole, 4,5-dihydro-1H-pyrazole, 4,5-dihydro-1H-imidazole, 4,5-dihydro-1,2-oxazole, 4,5-dihydro-1,3-oxazole, 4,5-dihydro-1,3-thiazole, 2,3,4,5-tetrahydropyridine, 1,2,3,6-tetrahydropyrazine, 5,6-dihydro-4H-1,2-oxazine and 3,6- dihydro-2-H-1,4-oxazine and preferably include azetidine, pyrrolidine, tetrahydrofuran, piperidine, tetrahydro-2H-pyran, imidazolidine, 1,3-oxazolidine, 1,3-thiazolidine, hexahydropyridazine, piperazine, morpholine, 1,2-oxazinane, azepane, 1,4-diazepane or 1,2-oxazepane.

Specific examples of "heterocyclylcarbonyl" include a variety of heterocyclylcarbonyl having "heterocyclyl" specifically illustrated above.

Specific examples of "$R^5(R^6)N$—" groups include amino, methylamino, ethylamino, propylamino, isopropylamino, butylamino, tert-butylamino, s-butylamino, isobutylamino, pentylamino, 1,1-dimethylpropylamino, 1,2-dimethylpropylamino, neopentylamino, 1-methylbutylamino, 2-methylbutylamino, isopentylamino, hexylamino, N,N-dimethylamino, N,N-diethylamino, N,N-dipropylamino, N,N-di(isopropyl)amino, N,N-dibutylamino, N,N-di(tert-butyl)amino, N,N-di(s-butyl)amino, N,N-di(isobutyl)amino, N,N-dipentylamino, N,N-di(1,1-dimethylpropyl)amino, N,N-di(1,2-dimethylpropyl)amino, N,N-di(neopentyl)amino, N,N-di(1-methylbutyl)amino, N,N-di(2-methylbutyl)amino, N,N-di(isopentyl)amino and N,N-di(hexyl)amino and preferably include amino, methylamino, ethylamino, propylamino, isopropylamino, N,N-dimethylamino and N,N-diethylamino.

Specific examples of groups formed in the case of $R^5$ and $R^6$ of $R^5(R^6)N$-connecting to form a heterocyclyl group include azetidin-1-yl, pyrrolidin-1-yl, piperidin-1-yl and azepan-1-yl groups. It goes without saying that the aforementioned specific examples include those connected with a protecting group in the form of a tert-butoxycarbonyl (Boc) and benzyloxycarbonyl (Cbz, Z) group.

Specific examples of compounds represented by chemical Formula (II) provided by the present invention include:
1-tert-butyl 2-(2,5-dioxopyrrolidin-1-yl) (2S,5R)-5-((benzyloxy)amino) piperidine-1,2-dicarboxylate;
1-tert-butyl 2-(2,5-dioxopyrrolidin-1-yl) (2S,5R)-5-((benzyloxy) ((trichloromethoxy)carbonyl)amino)piperidine-1,2-dicarboxylate;
1-tert-butyl 2-(2,5-dioxopyrrolidin-1-yl) (2S,5R)-5-((benzyloxy) (chlorocarbonyl)amino)piperidine-1,2-dicarboxylate;
1-tert-butyl 2-(1,3-dioxo-3a,4,7,7a-tetrahydro-1H-isoindol-2(3H)-yl) (2S,5R)-5-((benzyloxy)amino)piperidine-1,2-dicarboxylate;
1-tert-butyl 2-(1,3-dioxo-3a,4,7,7a-tetrahydro-1H-isoindol-2(3H)-yl) (2S,5R)-5-((benzyloxy)((trichloromethoxy)carbonyl)amino)piperidine-1,2-dicarboxylate;
1-tert-butyl 2-(1,3-dioxo-3a,4,7,7a-tetrahydro-1H-isoindol-2(3H)-yl) (2S,5R)-5-((benzyloxy)(chlorocarbonyl)amino)piperidine-1,2-dicarboxylate;
1-tert-butyl 2-(1,3-dioxohexahydro-1H-isoindol-2(3H)-yl) (2S,5R)-5-((benzyloxy)amino)piperidine-1,2-dicarboxylate;
1-tert-butyl 2-(1,3-dioxohexahydro-1H-isoindol-2(3H)-yl) (2S,5R)-5-((benzyloxy)((trichloromethoxy)carbonyl)amino)piperidine-1,2-dicarboxylate;
1-tert-butyl 2-(1,3-dioxohexahydro-1H-isoindol-2(3H)-yl) (2S,5R)-5-((benzyloxy)(chlorocarbonyl)amino)piperidine-1,2-dicarboxylate;
1-tert-butyl 2-(3,5-dioxo-4-azatricyclo[5.2.1.0$^{2,6}$]dec-8-en-4-yl) (2S,5R)-5-((benzyloxy)amino)piperidine-1,2-dicarboxylate;
1-tert-butyl 2-(3,5-dioxo-4-azatricyclo[5.2.1.0$^{2,6}$]dec-8-en-4-yl) (2S,5R)-5-((benzyloxy)((trichloromethoxy)carbonyl)amino)piperidine-1,2-dicarboxylate; and
1-tert-butyl 2-(3,5-dioxo-4-azatricyclo[5.2.1.0$^{2,6}$]dec-8-en-4-yl) (2S,5R)-5-((benzyloxy)(chlorocarbonyl)amino)piperidine-1,2-dicarboxylate.

More preferably, these specific examples include:
1-tert-butyl 2-(2,5-dioxopyrrolidin-1-yl) (2S,5R)-5-((benzyloxy)amino) piperidine-1,2-dicarboxylate;
1-tert-butyl 2-(1,3-dioxo-3a,4,7,7a-tetrahydro-1H-isoindol-2(3H)-yl) (2S,5R)-5-((benzyloxy)amino)piperidine-1,2-dicarboxylate;
1-tert-butyl 2-(1,3-dioxohexahydro-1H-isoindol-2(3H)-yl) (2S,5R)-5-((benzyloxy)amino)piperidine-1,2-dicarboxylate; and
1-tert-butyl 2-(3,5-dioxo-4-azatricyclo[5.2.1.0$^{2,6}$]dec-8-en-4-yl) (2S,5R)-5-((benzyloxy)amino)piperidine-1,2-dicarboxylate;
and they are represented by the following Formulas (II-30), (II-31), (II-32), and (II-33).

[Chemical Formula 27]

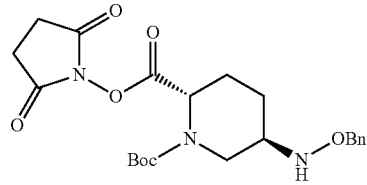

II-30

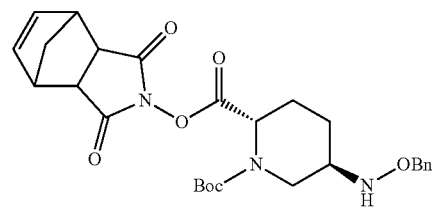

II-31

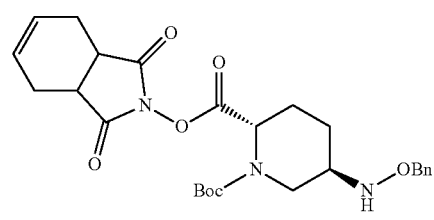

II-32

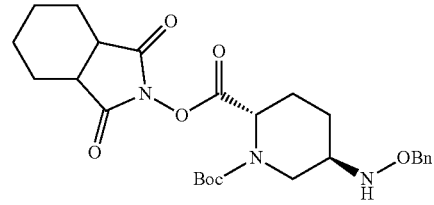

II-33

Specific examples of compounds represented by chemical Formula (III) provided by the present invention include:
2,5-dioxopyrrolidin-1-yl (2S,5R)-6-(benzyloxy)-7-oxo-1,6-diazabicyclo [3.2.1]octane-2-carboxylate;
1,3-dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate;
1,3-dioxohexahydro-1H-isoindol-2(3H)-yl (2S,5R)-6-(benzyloxy)-7-oxo-1,6-diazabicyclo[3.2.1]octane-2-carboxylate; and
3,5-dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate;

and they are represented by the following Formulas (III-57), (III-58), (III-59), and (III-60):

[Chemical Formula 28]

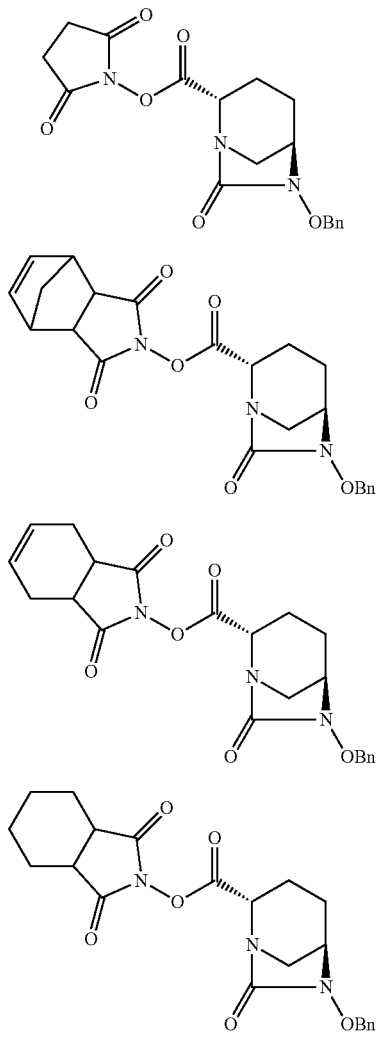

(wherein OBn is benzyloxy).

Continuing, specific examples of compounds formed in the case of a substituent defined by $R^4$ modifying a $C_{1-6}$ alkyl or heterocyclyl that forms $R^3O$— are explained by listing even more specific typical examples thereof, but it goes without saying that these compounds are not limited to the scope of the indicated specific examples.

Specific examples of an amino group ($H_2N$—) of a typical example of $R^5(R^6)N$-modifying a "$C_{1-6}$ alkyl" include 2-aminoethyl, 2-aminopropyl, 3-aminopropyl, 2-amino-1-methylethyl, 2-aminobutyl, 3-aminobutyl, 4-aminobutyl, 2-amino-1,1-dimethylethyl, 2-amino-1-methylpropyl, and 3-amino-2-methylpropyl. Here, it goes without saying that the aforementioned specific examples include those connected with a tert-butoxycarbonyl (Boc) or benzyloxycarbonyl (Cbz, Z) protecting group contained in $R^5OCO$—.

Specific examples of a methyl group of a typical example of a $C_{1-6}$ alkyl modifying a heterocyclyl include 1-methylazetidine, 3-methylazetidine, 1-methylpyrrolidine, 3-methylpyrrolidine, 1-methylimidazolidine, 3-methyloxazolidine, 1-methylpyrazolidine, 1-methylpiperidine, 4-methylpiperidine, 2-methyltetrahydro-2H-pyran, 4-methyltetrahydro-2H-pyran, 1-methylpiperazine, 1,4-dimethylpiperazine, 4-methylmorpholine, 4-methyl-thiomorpholine, 1-methylazepane, 1-methyl-1,4-diazepane and 1,4-dimethyl-1,4-diazepane. Here, it goes without saying that the aforementioned specific examples include those connected with a tert-butoxycarbonyl (Boc) or benzyloxycarbonyl (Cbz, Z) protecting group.

Specific examples of an amino group ($H_2N$—) of a typical example of $R^5(R^6)N$-modifying a heterocyclyl include 3-aminoazetidine, 3-aminopyrrolidine, 3-amino-tetrahydrofuran, 3-amino-tetrahydrothiophene, 4-aminopyrazolidine, 4-aminopiperidine, 4-amino-tetrahydro-2H-pyran, 4-amino-tetrahydro-2H-thiopyran, 4-amino-hexahydropyridazine, 4-amino-1,2-oxazolidine, 4-amino-1,2-oxazinane, 4-aminoazepane, 4-aminooxepane and 6-amino-1,4-diazepane. Here, it goes without saying that the aforementioned specific examples include those connected with a tert-butoxycarbonyl (Boc) or benzyloxycarbonyl (Cbz, Z) protecting group.

Specific examples of a heterocyclyl modifying a methyl or ethyl of a typical example of a $C_{1-6}$ alkyl include azetidin-2-ylmethyl, azetidin-3-ylmethyl, pyrrolidin-2-ylmethyl, pyrrolidin-3-ylmethyl, tetrahydrofuran-3-ylmethyl, tetrahydrothiophen-3-ylmethyl, pyrazolidin-4-ylmethyl, 1,2-oxazolidin-3-ylmethyl, piperidin-2-ylmethyl, piperidin-3-ylmethyl, piperidin-4-ylmethyl, tetrahydro-2H-pyran-4-ylmethyl, tetrahydro-2H-thiopyran-4-ylmethyl, hexahydropyridazin-4-ylmethyl, piperazin-2-ylmethyl, 1,2-oxazinan-3-ylmethyl, morpholin-2-ylmethyl, morpholin-3-ylmethyl, thiomorpholin-2-ylmethyl, thiomorpholin-3-ylmethyl, azepan-2-ylmethyl, azepan-4-ylmethyl, oxepan-2-ylmethyl, oxepan-4-ylmethyl, 1,4-diazepan-2-ylmethyl, 1,4-diazepan-6-ylmethyl, 2-(azetidin-1-yl)ethyl, 2-(pyrrolidin-1-yl)ethyl, 2-(pyrazolidin-1-yl)ethyl, 2-(piperidin-1-yl)ethyl, 2-(hexahydropyridazin-1-yl)ethyl, 2-(piperazin-1-yl)ethyl, 2-(morpholin-4-yl)ethyl, 2-(thiomorpholin-4-yl)ethyl, 2-(1,2-oxazolidin-2-yl)ethyl, 2-(1,2-oxazinan-2-yl)ethyl, 2-(azepan-1-yl)ethyl, and 2-(1,4-diazepan-1-yl)ethyl. Here, it goes without saying that the aforementioned specific examples include those connected with a tert-butoxycarbonyl (Boc) or benzyloxycarbonyl (Cbz, Z) protecting group.

Specific examples of compounds represented by chemical Formula (IV) provided by the present invention preferably include:
(2S,5R)-6-benzyloxy-N-methoxy-7-oxo-1,6-diazabicyclo [3.2.1]octane-2-carboxamide;
(2S,5R)-6-benzyloxy-N-ethoxy-7-oxo-1,6-diazabicyclo [3.2.1]octane-2-carboxamide;
(2S,5R)-6-benzyloxy-N-(cyclobutylmethoxy)-7-oxo-1,6-diazabicyclo[3.2.1] octane-2-carboxamide;
tert-butyl {2-[({[(2S,5R)-6-benzyloxy-7-oxo-1,6-diazabicyclo[3.2.1]oct-2-yl] carbonyl}amino)oxy] ethyl}carbamate;
tert-butyl {2-[({[(2S,5R)-6-benzyloxy-7-oxo-1,6-diazabicyclo[3.2.1] oct-2-yl]carbonyl}amino)oxy]ethyl}(methyl) carbamate;
tert-butyl {2-[({[(2S,5R)-6-benzyloxy-7-oxo-1,6-diazabicyclo[3.2.1] oct-2-yl]carbonyl}amino)oxy]ethyl}(ethyl)carbamate;
tert-butyl {2-[({[(2S,5R)-6-benzyloxy-7-oxo-1,6-diazabicyclo[3.2.1]oct-2-yl] carbonyl}amino)oxy]ethyl}(propyl) carbamate;
tert-butyl {2-[({[(2S,5R)-6-benzyloxy-7-oxo-1,6-diazabicyclo[3.2.1]oct-2-yl] carbonyl}amino)oxy]ethyl}(propan-2-yl)carbamate;

(2S,5R)-6-benzyloxy-N-[2-(dimethylamino)ethoxy]-7-oxo-1,6-diazabicyclo[3.2.1]octane-2-carboxamide;

tert-butyl {(2S)-1-[({[(2S,5R)-6-benzyloxy-7-oxo-1,6-diazabicyclo[3.2.1]oct-2-yl] carbonyl}amino)oxy]propan-2-yl}carbamate;

tert-butyl {(2R)-1-[({[(2S,5R)-6-benzyloxy-7-oxo-1,6-diazabicyclo[3.2.1]oct-2-yl] carbonyl}amino)oxy]propan-2-yl}carbamate;

tert-butyl {(2S)-2-[({[(2S,5R)-6-benzyloxy-7-oxo-1,6-diazabicyclo[3.2.1]oct-2-yl] carbonyl}amino)oxy]propyl}carbamate;

tert-butyl {3-[({[(2S,5R)-6-benzyloxy-7-oxo-1,6-diazabicyclo[3.2.1]oct-2-yl] carbonyl}amino)oxy]propyl}carbamate;

(2S,5R)-6-benzyloxy-2-(1,2-oxazolidin-2-ylcarbonyl)-1,6-diazabicyclo[3.2.1] octan-7-one;

(2S,5R)-6-benzyloxy-2-(1,2-oxazinan-2-ylcarbonyl)-1,6-diazabicyclo[3.2.1] octan-7-one;

(2S,5R)-6-benzyloxy-N-[2-(morpholin-4-yl)ethoxy]-7-oxo-1,6-diazabicyclo[3.2.1]octane-2-carboxamide;

tert-butyl 4-{2-[({[(2S,5R)-6-benzyloxy-7-oxo-1,6-diazabicyclo[3.2.1]oct-2-yl]carbonyl}amino)oxy]ethyl}piperazine-1-carboxylate;

tert-butyl 4-{2-[({[(2S,5R)-6-benzyloxy-7-oxo-1,6-diazabicyclo[3.2.1]oct-2-yl] carbonyl}amino)oxy]ethyl}-1,4-diazepane-1-carboxylate;

tert-butyl (2S)-2-[({[(2S,5R)-6-benzyloxy-7-oxo-1,6-diazabicyclo[3.2.1]oct-2-yl]carbonyl}amino)oxy]methyl}azetidine-1-carboxylate;

tert-butyl (2S)-2-{[({[(2S,5R)-6-benzyloxy-7-oxo-1,6-diazabicyclo[3.2.1]oct-2-yl] carbonyl}amino)oxy]methyl}pyrrolidine-1-carboxylate;

tert-butyl (2R)-2-[({[(2S,5R)-6-benzyloxy-7-oxo-1,6-diazabicyclo[3.2.1]oct-2-yl]carbonyl}amino)oxy]methyl}pyrrolidine-1-carboxylate;

tert-butyl (3R)-3-[({[(2S,5R)-6-benzyloxy-7-oxo-1,6-diazabicyclo[3.2.1]oct-2-yl] carbonyl}amino)oxy]methyl}piperidine-1-carboxylate;

tert-butyl 3-[({[(2S,5R)-6-benzyloxy-7-oxo-1,6-diazabicyclo[3.2.1]oct-2-yl] carbonyl}amino)oxy]azetidine-1-carboxylate;

tert-butyl (3R)-3-[({[(2S,5R)-6-benzyloxy-7-oxo-1,6-diazabicyclo[3.2.1]oct-2-yl] carbonyl}amino)oxy]pyrrolidine-1-carboxylate;

tert-butyl (3S)-3-[({[(2S,5R)-6-benzyloxy-7-oxo-1,6-diazabicyclo[3.2.1]oct-2-yl] carbonyl}amino)oxy]pyrrolidine-1-carboxylate;

tert-butyl 3-{[({[(2S,5R)-6-benzyloxy-7-oxo-1,6-diazabicyclo[3.2.1]oct-2-yl] carbonyl}amino)oxy]methyl}azetidine-1-carboxylate;

tert-butyl (3R)-3-[({[(2S,5R)-6-benzyloxy-7-oxo-1,6-diazabicyclo[3.2.1]oct-2-yl]carbonyl}amino)oxy]methyl}piperidine-1-carboxylate;

tert-butyl 4-[({[(2S,5R)-6-benzyloxy-7-oxo-1,6-diazabicyclo[3.2.1]oct-2-yl] carbonyl}amino)oxy]piperidine-1-carboxylate;

tert-butyl 4-{[({[(2S,5R)-6-benzyloxy-7-oxo-1,6-diazabicyclo[3.2.1]oct-2-yl] carbonyl}amino)oxy]methyl}piperidine-1-carboxylate;

(2S,5R)-6-benzyloxy-N-[2-(1H-imidazol-1-yl)ethoxy]-7-oxo-1,6-diazabicyclo[3.2.1]octane-2-carboxamide;

(2S,5R)-6-benzyloxy-7-oxo-N-[2-(1H-pyrrol-1-yl)ethoxy]-1,6-diazabicyclo[3.2.1]octane-2-carboxamide;

(2S,5R)-6-benzyloxy-N-[2-(dimethylamino)-2-oxoethoxy]-7-oxo-1,6-diazabicyclo[3.2.1]octane-2-carboxamide;

tert-butyl 4-{[({[(2S,5R)-6-benzyloxy-7-oxo-1,6-diazabicyclo[3.2.1]oct-2-yl] carbonyl}amino)oxy]acetyl}piperazine-1-carboxylate;

(2S,5R)-6-benzyloxy-N-[2-(morpholin-4-yl)-2-oxoethoxy]-7-oxo-1,6-diazabicyclo[3.2.1]octane-2-carboxamide;

tert-butyl 4-{[({[(2S,5R)-6-benzyloxy-7-oxo-1,6-diazabicyclo[3.2.1]oct-2-yl] carbonyl}amino)oxy]acetyl}-1,4-diazepane-1-carboxylate;

(2S,5R)-6-benzyloxy-7-oxo-N-[2-(2-oxopyrrolidin-1-yl)ethoxy]-1,6-diazabicyclo[3.2.1]octane-2-carboxamide;

(2S,5R)-6-benzyloxy-7-oxo-N-[2-(2-oxoimidazolidin-1-yl)ethoxy]-1,6-diazabicyclo[3.2.1]octane-2-carboxamide;

(2S,5R)-6-benzyloxy-7-oxo-N-(2-triisopropylsilyloxyethoxy)-1,6-diazabicyclo[3.2.1]octane-2-carboxamide;

(2S,5R)-6-benzyloxy-N-(2-methoxyethoxy)-7-oxo-1,6-diazabicyclo[3.2.1] octane-2-carboxamide;

(2S,5R)-6-benzyloxy-N-[2-(methylsulfonyl)ethoxy]-7-oxo-1,6-diazabicyclo[3.2.1]octane-2-carboxamide; and benzyl {2-[({[(2S,5R)-6-benzyloxy-7-oxo-1,6-diazabicyclo[3.2.1]oct-2-yl] carbonyl}amino)oxy]ethyl}carbamate.

More preferably, these specific examples include:

tert-butyl {2-[({[(2S,5R)-6-benzyloxy-7-oxo-1,6-diazabicyclo[3.2.1]oct-2-yl] carbonyl}amino)oxy]ethyl}carbamate;

benzyl {2-[({[(2S,5R)-6-benzyloxy-7-oxo-1,6-diazabicyclo[3.2.1]oct-2-yl] carbonyl}amino)oxy]ethyl}carbamate;

tert-butyl {2-[({[(2S,5R)-6-benzyloxy-7-oxo-1,6-diazabicyclo[3.2.1] oct-2-yl]carbonyl}amino)oxy]ethyl}(methyl)carbamate;

tert-butyl {2-[({[(2S,5R)-6-benzyloxy-7-oxo-1,6-diazabicyclo[3.2.1]oct-2-yl] carbonyl}amino)oxy]ethyl}(propan-2-yl)carbamate;

(2S,5R)-6-benzyloxy-N-[2-(dimethylamino)ethoxy]-7-oxo-1,6-diazabicyclo[3.2.1]octane-2-carboxamide;

tert-butyl {(2S)-1-[({[(2S,5R)-6-benzyloxy-7-oxo-1,6-diazabicyclo[3.2.1]oct-2-yl] carbonyl}amino)oxy]propan-2-yl}carbamate;

tert-butyl {(2R)-1-[({[(2S,5R)-6-benzyloxy-7-oxo-1,6-diazabicyclo[3.2.1]oct-2-yl] carbonyl}amino)oxy]propan-2-yl}carbamate;

tert-butyl {3-[({[(2S,5R)-6-benzyloxy-7-oxo-1,6-diazabicyclo[3.2.1]oct-2-yl] carbonyl}amino)oxy]propyl}carbamate;

tert-butyl (2S)-2-{[({[(2S,5R)-6-benzyloxy-7-oxo-1,6-diazabicyclo[3.2.1]oct-2-yl] carbonyl}amino)oxy]methyl}azetidine-1-carboxylate;

tert-butyl (2R)-2-[({[(2S,5R)-6-benzyloxy-7-oxo-1,6-diazabicyclo[3.2.1]oct-2-yl] carbonyl}amino)oxy]methyl}pyrrolidine-1-carboxylate;

tert-butyl (3R)-3-[({[(2S,5R)-6-benzyloxy-7-oxo-1,6-diazabicyclo[3.2.1]oct-2-yl] carbonyl}amino)oxy]methyl}piperidine-1-carboxylate;

tert-butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate; and tert-butyl 3-{[({[(2S,5R)-6-benzyloxy-7-oxo-1,6-diazabicyclo[3.2.1]oct-2-yl] carbonyl}amino)oxy]methyl}azetidine-1-carboxylate;

and most preferably include compounds selected from tert-butyl {2-[({[(2S,5R)-6-benzyloxy-7-oxo-1,6-diazabicyclo[3.2.1]oct-2-yl] carbonyl}amino)oxy]ethyl}carbamate; and benzyl {2-[({[(2S,5R)-6-benzyloxy-7-oxo-1,6-diazabicyclo[3.2.1]oct-2-yl] carbonyl}amino)oxy]ethyl}carbamate;

and compounds represented by the following chemical formulas:

[Chemical Formula 29]
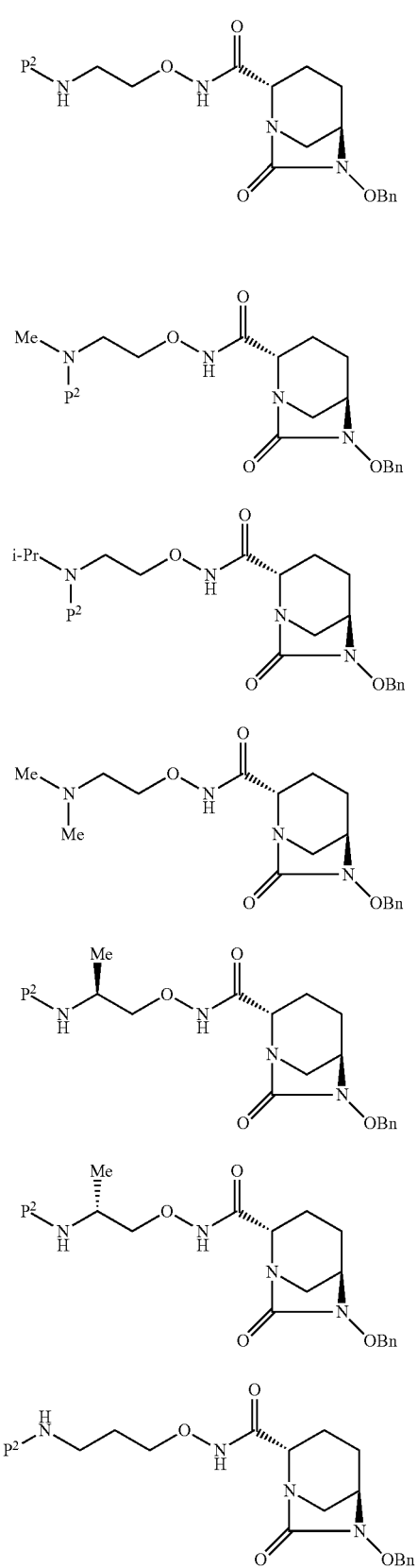
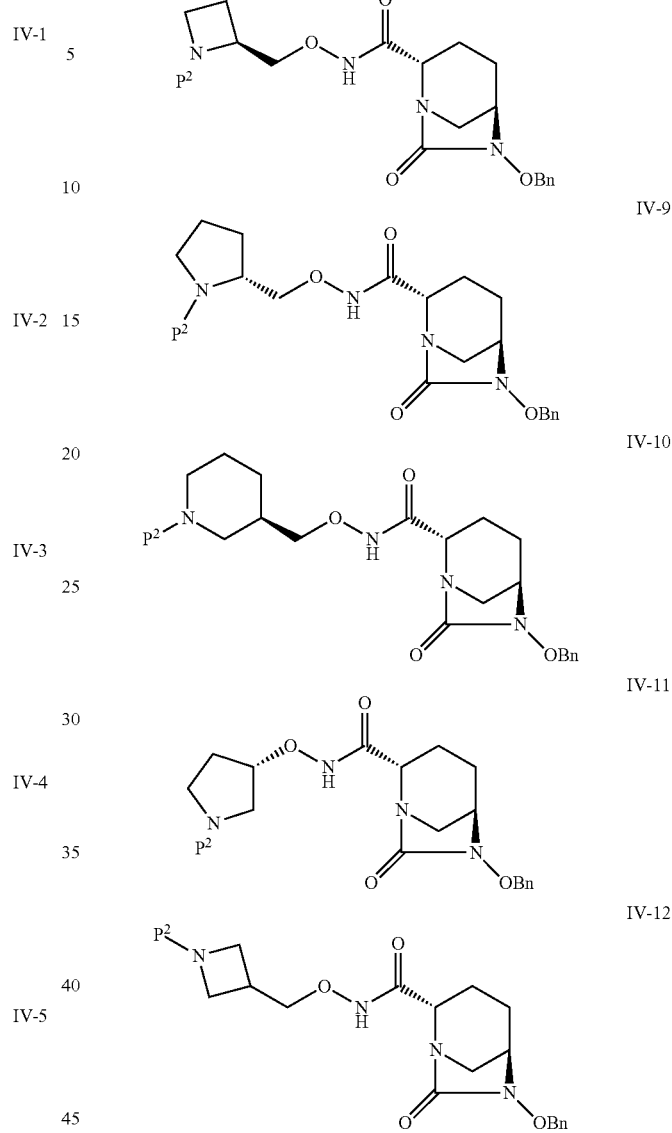
(wherein P² is tert-butoxycarbonyl (Boc) or benzyloxycarbonyl (Cbz) and OBn is benzyloxy).
The following provides sequentially explanations of the processes for producing compounds represented by the following Formulas (II), (III) and (IV) provided by the present invention.
Scheme 6
[Chemical Formula 30]
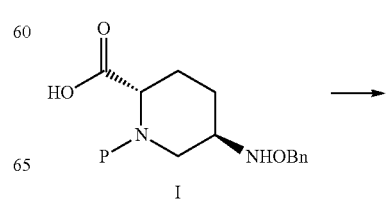

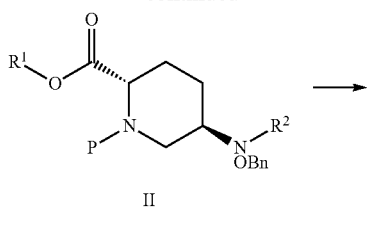

II

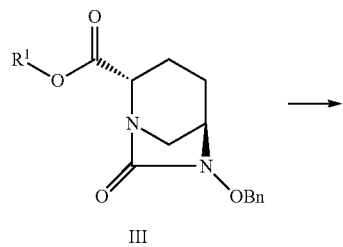

III

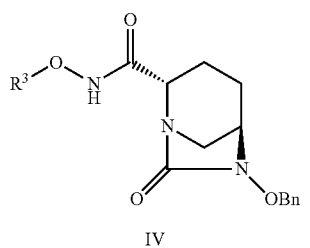

IV (In the aforementioned Formulas (I), (II), (III) and (IV), P, OBn, $R^1$, $R^2$ and $R^3$ are same as described above.)

A protecting group of an amino group able to be removed with an acid as described in Protective Groups in Organic Synthesis (T. W. Greene et al., Wiley, New York (1999)) can be employed as a suitable protecting group represented by P in the starting material represented by the following Formula (I) used as a starting material in the production process of the present invention:

[Chemical Formula 31]

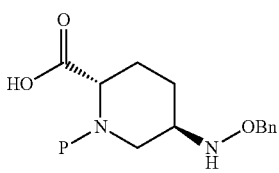

I (wherein OBn is benzyloxy and P is an NH protecting group capable of being removed with an acid). Specific examples thereof include tert-butoxycarbonyl (Boc), 2-trimethylsilylethoxycarbonyl (Teoc), 1-methyl-1-(4-biphenylyl)ethoxycarbonyl, 1-methylcyclobutoxycarbonyl, 1-adamantyloxycarbonyl, vinyloxycarbonyl, allyloxycarbonyl (Alloc), cinnamyloxycarbonyl, 4-methoxybenzyloxycarbonyl (PMZ, Moz) and diphenylmethoxycarbonyl groups, and preferred is a tert-butoxycarbonyl (Boc) group.

The step for obtaining a compound represented by the following Formula (II):

[Chemical Formula 32]

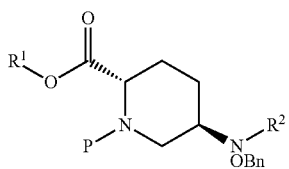

II (in the Formula (II), OBn, P and $R^1$ are same as described above) wherein $R^2$ is a hydrogen, from the compound represented by the aforementioned Formula (I), is carried out by esterification of the compound represented by the aforementioned Formula (I) with $R^1OH$ selected from 1-hydroxypyrrolidine-2,5-dione, 2-hydroxy-3a,4,7,7a-tetrahydro-1H-isoindol-1,3(2H)-dione, 2-hydroxyhexahydro-1H-isoindol-1,3(2H)-dione, or 4-hydroxy-4-azatricyclo[5.2.1.0$^{2,6}$]dec-8-ene-3,5-dione.

Esterification is carried out with a dehydration condensation agent or by a mixed acid anhydride method in the presence of a base.

Examples of reaction solvent used in esterification include ethyl acetate, toluene, tetrahydrofuran, 2-methyltetrahydrofuran, dioxane, acetonitrile, dichloromethane, chloroform, dichloroethane, dimethylformamide and dimethylacetamide, preferable examples include ethyl acetate, tetrahydrofuran, dichloromethane, chloroform, acetonitrile, dimethylformamide and dimethylacetamide, and these reaction solvents are used alone or as a mixture.

Examples of base used in the esterification reaction include sodium hydrogencarbonate, potassium hydrogencarbonate, sodium carbonate, potassium carbonate, cesium carbonate, sodium hydroxide, potassium hydroxide, triethylamine, diisopropylethylamine, dimethylbutylamine, tributylamine, N-methylmorpholine, pyridine, N-methylimidazole and 4-dimethylaminopyridine, preferable examples include triethylamine, diisopropylethylamine and 4-dimethylaminopyridine, and the base is used as necessary within the range of 1 to 2 equivalents, and preferably 0.5 to 1.5 equivalents, based on the compound represented by Formula (I).

The $R^1OH$ selected from 1-hydroxypyrrolidine-2,5-dione, 2-hydroxy-3a,4,7,7a-tetrahydro-1H-isoindol-1,3(2H)-dione, 2-hydroxyhexahydro-1H-isoindol-1,3(2H)-dione, or 4-hydroxy-4-azatricyclo[5.2.1.0$^{2,6}$]dec-8-ene-3,5-dione used in esterification is used as necessary within the range of 1 to 3 equivalents, and preferably 1 to 2 equivalents, based on the compound represented by Formula (I).

Examples of reagents used for the dehydration condensation agent and mixed acid anhydride method used in the esterification reaction include carbodiimides such as N,N'-diisopropylcarbodiimide, N,N'-dicyclohexylcarbodiimide or 1-ethyl-3-(3-dimethylaminopropyl)carbodiimide hydrochloride, propylphosphonic acid anhydride, diphenylphosphinyl chloride, bis(2-oxo-3-oxazolidinyl)phosphinyl chloride, ethyl chloroformate, isobutyl chloroformate, 2,4,6-trichlorobenzoyl chloride, methanesulfonyl chloride, 4-toluenesulfonyl chloride, dimethylsulfamoyl chloride, bis(2-pyridyl)carbonate or bis(2-thienyl)carbonate, and preferable examples include isobutyl chloroformate and 1-ethyl-3-(3-dimethylaminopropyl)carbodiimide hydrochloride. The reagent used for the dehydration condensation agent and mixed acid anhydride method is used as necessary within the range of 0.8 to 2 equivalents, and preferably 1 to 1.5 equivalents, based on the compound represented by Formula (I).

The reaction temperature is within the range of −40° C. to room temperature and preferably within the range of −20° C. to room temperature. The reaction time is within the range of 30 minutes to 1 day and preferably within the range of 2 to 16 hours.

The compound represented by Formula (II) can be isolated following completion of the reaction by diluting the reaction solution with a suitable solvent and sequentially washing with water, diluted acid and an aqueous basic solution (such as diluted hydrochloric acid, potassium hydrogensulfate, citric acid and aqueous sodium bicarbonate or saturated brine) followed by concentrating by evaporating the solvent. Examples of organic solvents used for dilution include diethyl ether, ethyl acetate, butyl acetate, toluene, dichloromethane and chloroform, and ethyl acetate is preferable.

Carbonylation of a compound obtained by the aforementioned esterification is carried out in the manner described below.

Examples of solvents used in the reaction include ethyl acetate, toluene, tetrahydrofuran, 2-methyltetrahydrofuran, dioxane, acetonitrile, dichloromethane, chloroform, dichloroethane, dimethylformamide and dimethylacetamide, preferable examples include ethyl acetate, tetrahydrofuran, dichloromethane, chloroform and acetonitrile, and the solvents are used alone or as a mixture.

Carbonylation is preferably carried out in the presence of a base. Examples of base used in the reaction include triethylamine, diisopropylethylamine, dimethylbutylamine, tributylamine, N-methylmorpholine, pyridine, N-methylimidazole and 4-dimethylaminopyridine, preferable examples include triethylamine and diisopropylethylamine, and the base is used within the range of 1 to 6 equivalents, and preferably within the range of 2 to 3 equivalents, based on the compound obtained by esterification.

Examples of carbonylation agents used in the reaction include phosgene, diphosgene and triphosgene, triphosgene is preferable, and the carbonylation agent is used within the range of 0.33 to 2 equivalents, and preferably within the range of 0.33 to 1 equivalent, based on the compound obtained by esterification.

The reaction temperature is within the range of −25 to 50° C. and preferably within the range of −15 to 30° C. The reaction time is 10 minutes to 24 hours and preferably 1 to 4 hours. Following completion of the reaction, the production process proceeds to the next step without isolating or purifying the reaction product after confirming the presence thereof in the form of trichloromethoxycarbamate or chlorocarbamate and completion of the reaction by an analytical means such as TLC.

Deprotection of the protecting group P of the compound represented by Formula (II) obtained by the aforementioned step under acidic conditions is carried out in the manner described below.

Examples of solvents used include water, methanol, ethanol, isopropanol, ethyl acetate, tetrahydrofuran, dioxane, dichloromethane, chloroform, 1,2-dichloroethane and 2,2,2-trifluoroethanol, preferable examples include ethyl acetate, dioxane, dichloromethane, chloroform and dichloroethane, and the solvents are used alone or as a mixture. Examples of acids used for deprotection include hydrochloric acid, sulfuric acid, phosphoric acid, formic acid, trifluoroacetic acid, methanesulfonic acid, trifluoromethanesulfonic acid, chloromethanesulfonic acid and tetrafluoroboric acid, and preferable examples include hydrochloric acid, sulfuric acid, trifluoroacetic acid, methanesulfonic acid and tetrafluoroboric acid. Methanesulfonic acid is more preferable. The acid is used within the range of 1 equivalent based on the compound represented by Formula (II) to the amount of solvent, and preferably within the range of 5 to 20 equivalents, based on the compound represented by Formula (II). The reaction temperature is within the range of −25 to 50° C. and preferably within the range of −10 to 30° C. The reaction time is within the range of 1 minute to 1 hour and preferably within the range of 5 to 30 minutes. Following completion of the reaction, the production process proceeds to the next step without isolating or purifying the reaction product after confirming the presence thereof in the form of a salt of the acid used and completion of the reaction by an analytical means such as TLC.

Continuing, a cyclization reaction for obtaining a compound represented by the following Formula (III):

[Chemical Formula 33]

$$R^1\text{-O-C(=O)-[piperidine ring]-N-N(OBn)-C(=O)}$$

III (wherein OBn and $R^1$ are same as described above) from a compound represented by the aforementioned Formula (II) following removal of the protecting group P is carried out in the manner described below.

The reaction is carried out by continuously treating the reaction solution of a compound represented by the aforementioned Formula (II) with a base.

Examples of base used in the reaction include sodium hydrogencarbonate, potassium hydrogencarbonate, sodium carbonate, potassium carbonate, cesium carbonate, sodium hydroxide, potassium hydroxide, triethylamine, diisopropylethylamine, dimethylbutylamine, tributylamine, N-methylmorpholine, pyridine, N-methylimidazole and 4-dimethylaminopyridine, preferable examples include sodium hydrogencarbonate, potassium hydrogencarbonate, triethylamine and diisopropylethylamine, and an aqueous solution can be used in the case of using an inorganic base. The base is used in slight excess based on the acid used to deprotect Formula (II), and is preferably used at 5 to 20 times the amount of the compound represented by Formula (II). The reaction temperature is within the range of −25 to 50° C. and preferably within the range of −10 to 10° C. The reaction time is within the range of 0.5 to 3 hours and preferably within the range of 0.5 to 1 hour.

The compound represented by Formula (III) can be isolated by diluting the reaction solution with a suitable solvent following completion of the reaction, and sequentially washing with water, diluted acid and an aqueous basic solution (such as dilute hydrochloric acid, potassium hydrogensulfate, citric acid and aqueous sodium bicarbonate or saturated brine) followed by concentrating by evaporating the solvent. Examples of organic solvents used for dilution include diethyl ether, ethyl acetate, butyl acetate, toluene, dichloromethane and chloroform, and ethyl acetate is preferable.

Purification is carried out by an ordinary procedure such as silica gel column chromatography, precipitation or crystallization.

Continuing, synthesis of a compound represented by the following Formula (IV):

[Chemical Formula 34]

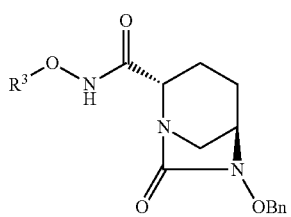

(wherein OBn and $R^3$ are same as described above) from a compound represented by the aforementioned Formula (III) is carried out in the manner described below.

Examples of solvents used in the reaction include water, methanol, ethanol, isopropanol, ethyl acetate, tetrahydrofuran, dioxane, dichloromethane, chloroform, 1,2-dichloroethane and 2,2,2-trifluoroethanol, preferable examples include ethyl acetate, dioxane, dichloromethane, chloroform and dichloroethane, and the solvents are used alone or as a mixture.

The compound: $R^3ONH_2$ used in the reaction can be preferably selected from those listed in the specific examples of $R^3$, and is used within the range of 1 to 2 equivalents, and preferably within the range of 1 to 1.3 equivalents, based on a compound represented by Formula (III).

Examples of base used in the reaction include sodium hydrogencarbonate, potassium hydrogencarbonate, sodium carbonate, potassium carbonate, cesium carbonate, sodium hydroxide, potassium hydroxide, triethylamine, diisopropylethylamine, dimethylbutylamine, tributylamine, N-methylmorpholine, pyridine, N-methylimidazole and 4-dimethylaminopyridine, preferable examples include sodium hydrogencarbonate, potassium hydrogencarbonate, triethylamine and diisopropylethylamine, and an aqueous solution can be used in the case of using an inorganic base. The base is used within the range of 0 to 2 equivalents and preferably within the range of 0 to 1.5 equivalents based on a compound represented by Formula (III). $R^3ONH_2$ is used within the range of 0 to 2 equivalents and preferably within the range of 0 to 1.5 equivalents based on a compound represented by Formula (III). The reaction temperature is within the range of −25 to 50° C. and preferably within the range of −10 to 10° C. The reaction time is within the range of 1 to 24 hours and preferably within the range of 1 to 16 hours.

The compound represented by Formula (IV) can be isolated by diluting the reaction solution with a suitable solvent following completion of the reaction, and sequentially washing with water, diluted acid and an aqueous basic solution (such as dilute hydrochloric acid, potassium hydrogensulfate, citric acid and aqueous sodium bicarbonate or saturated brine) followed by concentrating by evaporating the solvent. Examples of organic solvents used for dilution include diethyl ether, ethyl acetate, butyl acetate, toluene, dichloromethane and chloroform, and ethyl acetate is preferable. Purification is carried out by an ordinary procedure such as silica gel column chromatography, precipitation or crystallization.

EXAMPLES

The present invention will be described below in more detail by way of Examples, but the present invention is not intended to be limited by these Examples, and various modifications can be made.

Reference Example 1

Methyl (2S,5R)-5-(benzyloxyamino)piperidine-2-carboxylate (2) dihydrochloride

Step 1

Methyl (2S,5S)-5-hydroxypiperidine-2-carboxylate

To 2 M hydrogen chloride-methanol solution (12.8 L) was added commercially available (2S,5S)-5-hydroxypiperidine-2-carboxylic acid (prelabel HPLC content 84%, net 912.22 g, washed with 3.1 L of 2 M hydrogen chloride-methanol), followed by refluxing for 3 hours (internal temperatures of from 63 to 67° C.). After the reaction solution was cooled, 1,4-dioxane (12.8 L) was added, and the solvent was distilled off under reduced pressure. To the residue (4.1 kg) were added ethyl acetate (18.3 L) and an ice-cold 44% potassium carbonate (23.7 L) and the organic layer was separated, and the aqueous layer was further extracted with ethyl acetate (3×18.3 L). Each of the organic layers was washed with a 50% potassium carbonate (7.3 L). The organic layers were combined, dried over anhydrous potassium carbonate (2.37 kg) and filtered, and the solvent was distilled off under reduced pressure. The residue was dissolved in toluene (9.1 L), and 9.2 g of activated carbon was added, followed by stirring for 30 minutes and filtering. The solvent was then distilled off under reduced pressure. The solvent of the residue was switched to ethyl acetate (9.1 L) to afford 1130 g of the title compound as a pale yellow-oil (prelabel HPLC content 78.9%, net 891.57 g, yield 89%).

Step 2

Methyl (2S,5S)-5-hydroxy-1-(2,2,2-trifluoroacetyl)piperidine-2-carboxylate

A solution of methyl (2S,5S)-5-hydroxypiperidine-2-carboxylate (prelabel HPLC content 78.8%, net 459.48 g) in dehydrated ethyl acetate (7.4 L) was cooled to −40° C., followed by addition of triethylamine (1300 g) and then dropwise addition of trifluoroacetic acid anhydride (1349 g, washed with 100 ml of dehydrated ethyl acetate) at −40 to −12° C. for 30 minutes. After completion of the dropwise addition, the temperature was elevated to −2° C. in 15 minutes, and the mixture was stirred for 75 minutes, and to the mixture was further added water (1277 mL), followed by stirring at 25° C. for 1 hour. The mixture was introduced into water (8.4 L) (washed with 4.5 L of ethyl acetate) and further extracted with ethyl acetate (2×9.8 L), and the combined organic layer was washed sequentially with 1 M hydrochloric acid (8.5 L), saturated sodium bicarbonate (8.5 L), and saturated brine (8.5 L), dried over anhydrous sodium sulfate (1.8 kg), and filtered. After the solvent of the organic layer was distilled off under reduce pressure, to the residue was added ethyl acetate (3.6 L), followed by concentration. The residue was then dried in vacuo to afford 793.4 g of the title compound (HPLC content 81.5%, net 648.66 g, yield 88%).

Step 3

Methyl (2S,5R)-5-(benzyloxyamino)-1-(2,2,2-trifluoroacetyl)piperidine-2-carboxylate 4.0 L of a solution of methyl (2S,5S)-5-hydroxy-1-(2,2,2-trifluoroacetyl) piperidine-2-carboxylate (HPLC content 81.5%, net 556.23 g) in dehydrated acetonitrile was cooled to −40° C., and 2,6-lutidine (259.24 g) was added (washed with 100 mL of acetonitrile), followed by dropwise addition of trifluoromethanesulfonic anhydride (645.72 g) at −43 to −37° C. over 1 hour and 10 minutes (washed with 100 mL of acetonitrile). The reaction solution was stirred at −35° C. for 50 minutes, and then benzyloxyamine (550.27 g) was added dropwise at −35° C. or less, followed by washing with acetonitrile (500 mL). After gradually elevating the temperature of the reaction solution to −5° C., 2,6-lutidine (259.24 g) was added, followed by stirring at 5° C. for 40 hours. After concentration to 1.8 L, the mixture was diluted with ethyl acetate (12.4 L), and washed sequentially with water (12.4 L), 10% citric acid (4×8 L+4.7 L), saturated sodium bicarbonate (6.3 L), and saturated brine (7.2 L). The organic layer was dried over anhydrous sodium sulfate, filtered, and then concentrated under reduced pressure. The residue was dried in vacuo to afford 867.73 g of the title compound (HPLC content 71.56%, yield 79%).

Step 4

Methyl (2S,5R)-5-(benzyloxyamino)-1-(2,2,2-trifluoroacetyl)piperidine-2-carboxylate hydrochloride Methyl (2S,5R)-5-(benzyloxyamino)-1-(2,2,2-trifluoroacetyl)piperidine-2-carboxylate (HPLC content 70.13%, net 673.20 g) was diluted with ethyl acetate (4.8 L), and 48 g of activated carbon was added, followed by stirring for 1 hour. The mixture was filtered and washed with 2 L of ethyl acetate. The filtrate was diluted with 4.7 L of ethyl acetate, and 1 M hydrogen chloride in ethyl acetate (2.7 L) was added at room temperature, followed by stirring for 15 minutes, and then 28.6 L of hexane was added, followed by cooling to 0° C. After stirring and aging for 3 hours, the crystalline solid was filtered, washed with hexane/ethyl acetate=4/1 (3 L), and dried in vacuo to afford 724.0 g of the title compound (HPLC content 91.72%, yield 90%).

Step 5

Methyl (2S,5R)-5-(benzyloxyamino)piperidine-2-carboxylate (2) dihydrochloride

Methyl (2S,5R)-5-(benzyloxyamino)-1-(2,2,2-trifluoroacetyl)piperidine-2-carboxylate (HPLC content 92.01%, net 732.25 g) was dissolved in 2 M hydrogen chloride in methanol (15 L), followed by heating at reflux for 27 hours. The mixture was cooled to room temperature and concentrated under reduced pressure to 3 L. The mixture was diluted with 2.7 L of methanol, and then 16.3 L of ethyl acetate was added, followed by stirring for 1 hour. The precipitated crystalline-solid was filtered, washed with ethyl acetate (3×1.1 L), and dried in vacuo to afford 572.0 g of the title compound (HPLC content 98.06%, yield 92%).

$^1$H NMR (400 MHz, D$_2$O) δ 1.40-1.51 (m, 1H), 1.61-1.72 (m, 1H), 1.90-1.94 (m, 1H), 2.25-2.30 (m, 1H), 2.80 (t, J=11.2 Hz, 1H), 3.19-3.27 (m, 1H), 3.51-3.55 (m, 1H), 3.66 (s, 3H), 3.87-3.91 (m, 1H), 4.68 (s, 2H), 7.27 (s, 5H); MS m/z 265 [M−2HCl+H]$^+$.

Reference Example 2

(2S,5R)-6-(Benzyloxy)-7-oxo-1,6-diazabicyclo[3.2.1]octane-2-carboxylic acid (4)

Step 1

Methyl (2S,5R)-5-(benzyloxyamino)piperidine-2-carboxylate (2)

To methyl (2S,5R)-5-(benzyloxyamino)piperidine-2-carboxylate dihydrochloride (1.319 g) were added ethyl acetate (20 mL) and a 50% aqueous potassium carbonate solution (20 mL) to separate the layers. The aqueous layer was extracted three times with ethyl acetate (15 mL). The organic layer was washed with saturated brine, dried over anhydrous sodium sulfate, filtered, then concentrated under reduced pressure and dried in vacuo overnight to afford 975 mg of the title compound (yield 94%).

$^1$H NMR (400 MHz, CDCl$_3$) δ 1.25-1.35 (m, 1H), 1.49-1.59 (m, 1H), 1.89-2.11 (m, 2H), 2.45 (t, J=11.7 Hz, 1H), 2.96-3.03 (m, 1H), 3.28-3.39 (m, 2H), 3.72 (s, 3H), 4.68 (s, 2H), 7.26-7.35 (m, 5H); MS m/z 265 [M+H]$^+$.

Step 2

Methyl (2S,5R)-6-(benzyloxy)-7-oxo-1,6-diazabicyclo[3.2.1]octane-2-carboxylate (3)

To methyl (2S,5R)-5-(benzyloxyamino)piperidine-2-carboxylate (1.154 g, 4.37 mmol) was added dehydrated acetonitrile (198 mL), followed by ice-cooling. At 5° C. or less, triethylamine (1.60 mL) and diphosgene (0.389 mL) were sequentially added dropwise, followed by stirring at 2° C. for 20 minutes. To the reaction solution was then added 4-dimethylaminopyridine (70.0 mg), followed by stirring at room temperature for 10 hours. The reaction solution was concentrated under reduced pressure and solvent-switched three times to ethyl acetate, and the solution was then concentrated to 30 mL. To this were added ethyl acetate (20 mL) and water (40 mL) to separate the solution into layers. The separated aqueous layer was extracted twice with ethyl acetate (30 mL). The combined organic layer was washed sequentially with 5% citric acid (40 mL), 6.5% sodium bicarbonate (30 mL), and 5% brine (30 mL), dried over anhydrous sodium sulfate, filtered, and then concentrated under reduced pressure. 1.16 g of the resulting residue was diluted with ethyl acetate (5.5 mL), n-hexane (11 mL) was added, and seed crystals were seeded and crystallized. n-Hexane (49 mL) was further added and stirred at 0° C. for 1 hour, and crystalline solid was then filtered, washed with n-hexane (60 mL), and dried in vacuo to afford 882.3 mg of the title compound as a colorless crystalline powder (yield 71%).

$^1$H NMR (400 MHz, CDCl$_3$) δ 1.65-1.70 (m, 1H), 2.03-2.12 (m, 3H), 2.90 (d, J=12.0 Hz, 1H), 3.07 (m, 1H), 3.32 (m, 1H), 3.79 (s, 3H), 4.12 (dd, J=4.6 & 4.4 Hz, 1H), 4.91 (d, J=11.2 Hz, 1H), 5.06 (d, J=11.2 Hz, 1H), 7.35-7.44 (m, 5H); MS m/z 291 [M+H]$^+$.

Step 3

(2S,5R)-6-(Benzyloxy)-7-oxo-1,6-diazabicyclo
[3.2.1]octane-2-carboxylic acid (4)

To methyl (2S,5R)-6-(benzyloxy)-7-oxo-1,6-diazabicyclo [3.2.1]octane-2-carboxylate (809.0 mg, 2.79 mmol) were added tetrahydrofuran (8 mL) and water (3.6 mL), followed by dropwise addition of a 0.5 M aqueous lithium hydroxide solution (6.41 mL) at 4.9° C. or less over 10 minutes. After stirring the reaction solution at 2° C. for 2 hours, water (30 mL) was added, followed by washing with ethyl acetate (25 mL). To the separated aqueous layer was added ethyl acetate (15 mL), and the pH of the aqueous layer was adjusted to 4.0 with 1 M hydrochloric acid, followed by extraction twice with ethyl acetate (ethyl acetate: 65 mL in total). The separated aqueous layer was adjusted to pH 3.4 with 1 M hydrochloric acid, extracted once with ethyl acetate, and then the aqueous layer was adjusted to pH 2.4 and extracted twice with ethyl acetate. The ethyl acetate-extract extracted five times in total (175 mL) was washed with saturated brine (40 mL), dried over anhydrous sodium sulfate, filtered, and then concentrated under reduced pressure. 759.1 mg of the resulting residue was diluted with ethyl acetate (5 mL), n-hexane (3 mL) was added, and seed crystals were seeded and crystallized. An ethyl acetate/n-hexane (5/3) solution (8 mL) was further added and stirred, and then n-hexane (20 mL) was added, followed by stirring at 4° C. for 14 hours. The crystalline solid was filtered, washed with n-hexane (55 mL), and then dried in vacuo to afford 633.6 mg of the title compound as a colorless crystalline powder (yield 82%). As a result of evaluation of the stability of this product, it remained stable in a refrigerator for one month.

$^1$H NMR (400 MHz, CDCl$_3$) δ 1.67 (m, 1H), 2.04-2.26 (m, 3H), 2.85 (d, J=12.0 Hz, 1H), 3.13 (m, 1H), 3.35 (m, 1H), 4.12 (m, 1H), 4.91 (d, J=11.3 Hz, 1H), 5.06 (d, J=11.3 Hz, 1H), 7.37-7.44 (m, 5H); MS m/z 277 [M+H]$^+$.

Reference Example 3

(2S,5R)—N-(2-Aminoethoxy)-7-oxo-6-(sulfooxy)-1,
6-diazabicyclo[3.2.1]octane-2-carboxamide (VI-1)

Step 1 tert-Butyl {2-[({[(2S,5R)-6-benzyloxy-7-oxo-1,6-
diazabicyclo[3.2.1]oct-2-yl] carbonyl}amino)oxy]
ethyl}carbamate (IV-1-1)

A solution of (2S,5R)-6-(benzyloxy)-7-oxo-1,6-diazabicyclo[3.2.1]octane-2-carboxylic acid (4.30 g, 15.56 mmol) in dehydrated ethyl acetate (47 mL) was cooled to −30° C., and isobutyl chloroformate (2.17 g, washed with 1 mL of dehydrated ethyl acetate) and triethylamine (1.61 g, washed with 1 mL of dehydrated ethyl acetate) were added dropwise sequentially, followed by stirring at −30° C. for 1 hour. To the reaction solution was added a solution of tert-butyl 2-(aminooxy)ethylcarbamate (3.21 g) in dehydrated ethyl acetate (4 mL) (washed with 1 mL of dehydrated ethyl acetate), and the temperature was elevated to 0° C. over 1.5 hours, followed by further stirring overnight. The mixture was washed sequentially with 8% citric acid (56 mL), saturated sodium bicarbonate (40 mL) and saturated brine (40 mL), dried over anhydrous magnesium sulfate, subsequently filtered, concentrated to 5 mL, and further substitution-concentrated with ethanol (10 mL) to 6 mL. To the resulting solution were added ethanol (3 mL) and hexane (8 mL), followed by ice cooling, seeding, and stirring for 15 minutes. To the mixture was added dropwise hexane (75 mL) over 2 hours, followed by stirring overnight. The precipitated crystalline solid was filtered, washed with hexane, and dried in vacuo to afford 5.49 g of the title compound (net 4.98 g, yield 74%).

$^1$H NMR (400 MHz, CDCl$_3$) δ 1.44 (s, 9H), 1.56-1.70 (m, 1H), 1.90-2.09 (m, 2H), 2.25-2.38 (m, 1H), 2.76 (d, J=11.6 Hz, 1H), 3.03 (br.d., J=11.6 Hz, 1H), 3.24-3.47 (m, 3H), 3.84-4.01 (m, 3H), 4.90 (d, J=11.6 Hz, 1H), 5.05 (d, J=11.6 Hz, 1H), 5.44 (br.s., 1H), 7.34-7.48 (m, 5H), 9.37 (br.s., 1H); MS m/z 435 [M+H]$^+$.

Step 2 tert-Butyl {2-[({[(2S,5R)-6-hydroxy-7-oxo-1,6-diaz-
abicyclo[3.2.1]oct-2-yl] carbonyl}amino)oxy]
ethyl}carbamate (V-1)

To a solution of tert-butyl {2-[({[(2S,5R)-6-benzyloxy-7-oxo-1,6-diazabicyclo [3.2.1]oct-2-yl]carbonyl}amino)oxy] ethyl}carbamate (3.91 g, 9.01 mmol) in methanol (80 mL) was added a 10% palladium carbon catalyst (50% wet, 803 mg), followed by stirring under a hydrogen atmosphere for 45 minutes. The reaction solution was filtered through a Celite pad and concentrated under reduced pressure, and then 3.11 g of the title compound was afforded (quantitative).

$^1$H NMR (400 MHz, CD$_3$OD) δ 1.44 (s, 9H), 1.73-1.83 (m, 1H), 1.86-1.99 (m, 1H), 2.01-2.12 (m, 1H), 2.22 (br.dd., J=15.0, 7.0 Hz, 1H), 3.03 (d, J=12.0 Hz, 1H), 3.12 (br.d., J=12.0 Hz, 1H), 3.25-3.35 (m, 2H), 3.68-3.71 (m, 1H), 3.82-3.91 (m, 3H); MS m/z 345 [M+H]$^+$.

Step 3

(2S,5R)—N-(2-Aminoethoxy)-7-oxo-6-(sulfooxy)-1,
6-diazabicyclo[3.2.1]octane-2-carboxamide (VI-1)

To a solution of tert-butyl {2-[({[(2S,5R)-6-hydroxy-7-oxo-1,6-diazabicyclo [3.2.1]oct-2-yl]carbonyl}amino)oxy] ethyl}carbamate (3.09 g, 8.97 mmol) in dichloromethane (80 mL) were added 2,6-lutidine (3.20 mL) and sulfur trioxide-pyridine complex (3.58 g), followed by stirring at room temperature overnight. The reaction solution was poured into semi-saturated sodium bicarbonate, the aqueous layer was washed with chloroform, and subsequently to the aqueous layer were added tetrabutylammonium hydrogen sulfate (3.47 g) and chloroform (30 mL), followed by stirring for 10 minutes. After the aqueous layer was extracted with chloroform, the resulting organic layer was dried over anhydrous sodium sulphate, filtered, and then concentrated under reduced pressure to afford 5.46 g of tetrabutylammonium tert-butyl {2-[({[(2S,5R)-7-oxo-6-(sulfooxy)-1,6-diazabicyclo[3.2.1]oct-2-yl] carbonyl}amino)oxy]ethyl}carbamate (yield 91%).

$^1$H NMR (400 MHz, CDCl$_3$) δ 1.01 (t, J=7.4 Hz, 12H), 1.37-1.54 (m, 8H), 1.45 (s, 9H), 1.57-1.80 (m, 9H), 1.85-1.98 (m, 1H), 2.14-2.24 (m, 1H), 2.30-2.39 (m, 1H), 2.83 (d, J=11.6 Hz, 1H), 3.20-3.50 (m, 11H), 3.85-3.99 (m, 3H), 4.33-4.38 (m, 1H), 5.51 (br s, 1H), 9.44 (br.s., 1H); MS m/z 425 [M-Bu$_4$N+2H]$^+$.

To a solution of this tetrabutylammonium salt (5.20 g, 7.82 mmol) in dichloromethane (25 mL) was added trifluoroacetic acid (25 mL) under ice cooling, followed by stirring at 0° C. for 1 hour. The reaction solution was concentrated under reduced pressure, the resulting residue was washed with diethyl ether, subsequently the pH was adjusted to 7 with a sodium bicarbonate aqueous solution, and octadecyl silica gel column chromatography purification (water) was carried out. After lyophilization, 1.44 g of the title compound was obtained (yield 57%).

$^1$H NMR (400 MHz, D$_2$O) δ 1.66-1.76 (m, 1H), 1.76-1.88 (m, 1H), 1.91-2.00 (m, 1H), 2.00-2.08 (m, 1H), 3.02 (d, J=12.0 Hz, 1H), 3.15 (t, J=5.0 Hz, 2H), 3.18 (br d, J=12.0 Hz, 1H), 3.95 (dd, J=7.8, 2.2 Hz, 1H), 4.04 (t, J=5.0 Hz, 2H), 4.07 (dd, J=6.4 & 3.2 Hz, 1H); MS m/z 325 [M+H]$^+$.

Reference Example 4

(2S,5R)-5-((Benzyloxy)amino)-1-(tert-butoxycarbonyl)piperidine-2-carboxylic acid (I)

Methyl (2S,5R)-5-(benzyloxyamino)piperidine-2-carboxylate, dihydrochloride (65.4 g, 200 mmol) was dissolved in water (400 mL) and 1,4-dioxane (270 mL), followed by ice cooling. 5 M sodium hydroxide (132 mL) was added, followed by stirring for 1 hour. To the reaction solution were added 5 M hydrochloric acid (12 mL), potassium carbonate (27.6 g) and di-tert-butyl dicarbonate (48 g), and the temperature was elevated to room temperature, followed by stirring overnight. The aqueous solution obtained by concentration of the reaction solution was washed with ethyl acetate, adjusted to pH 3.3 with citric acid•monohydrate, extracted twice with ethyl acetate (500 mL), washed with saturated brine, dried over anhydrous sodium sulfate, and filtered. The solvent was concentrated under reduced pressure, and further solvent-switched to ethyl acetate yielded 68.7 g of the title compound (quantitative). This compound was used in the next step without purification. A portion thereof was crystalized from ethyl acetate/hexane to confirm the structure.

$^1$H NMR (400 MHz, CDCl$_3$) δ 1.46 (s, 9H), 1.50-1.72 (m, 2H), 1.98-2.10 (m, 2H), 3.12-3.19 (m, 2H), 4.13-4.20 (m, 1H), 4.76 (d, J=11.5 Hz), 4.70 (d, J=11.5 Hz), 4.85-4.92 (m, 1H), 7.26-7.35 (m, 5H); MS m/z 351 [M+H]$^+$.

Reference Example 5 tert-Butyl {2-[({[(2S,5R)-6-hydroxy-7-oxo-1,6-diazabicyclo[3.2.1]oct-2-yl] carbonyl}amino)oxy] ethyl}carbamate (V-1)

Step 1

(2S,5R)—N-(2-benzyloxycarbonylaminoethoxy)-5-(benzyloxyamino)-1-(tert-butoxycarbonyl)piperidine-2-carboxamide (2S,5R)-5-((Benzyloxy)amino)-1-(tert-butoxycarbonyl) piperidine-2-carboxylic acid (1.879 g, 5.362 mmol), benzyl 2-(aminooxy)ethylcarbamate (1.41 g, 6.707 mmol) and 1-hydroxybenzotriazole•monohydrate (220 mg) were dissolved in dichloromethane (20 mL), followed by stirring under ice cooling.

N-Ethyl-N'-(3-dimethylaminopropyl)carbodiimide hydrochloride (1.29 g) was added thereto and the temperature was elevated to room temperature, followed by stirring overnight. The mixture was diluted with dichloromethane (20 mL), washed sequentially with water, 10% citric acid, saturated sodium bicarbonate and saturated brine, and dried over magnesium sulfate. The solvent was concentrated under reduced pressure to afford 2.91 g of the title compound (quantitative).

$^1$H NMR (400 MHz, CDCl$_3$) δ 1.46 (s, 9H), 1.50-1.93 (m, 4H), 3.40 (m, 2H), 3.89 (m, 2H), 4.15-4.21 (m, 1H), 4.61 (m, 1H), 4.69 (d, J=11.6 Hz, 1H), 4.76 (d, J=11.6 Hz, 1H), 5.11 (s, 2H), 5.86 (s, 1H), 7.27-7.36 (m, 5H), 9.28 (s, 1H); MS m/z 543 [M+H]$^+$.

Step 2

(2S,5R)—N-(2-Benzyloxycarbonylaminoethoxy)-5-(benzyloxyamino)piperidine-2-carboxamide (2S,5R)—N-(2-Benzyloxycarbonylaminoethoxy)-5-(benzyloxyamino)-1-(tert-butoxycarbonyl)piperidine-2-carboxamide (2.91 g, 5.362 mmol) was dissolved in 1,4-dioxane (5 mL), and 4 M hydrogen chloride in dioxane (10 mL) was added under ice cooling. After stirring for 2 hours, the mixture was concentrated under reduced pressure, dissolved in water (30 mL), and washed with ether. The aqueous layer was ice cooled and the pH was adjusted to about 7 with 5 M sodium hydroxide and acetic acid, followed by extraction with ethyl acetate. The organic layer was washed with saturated brine and dried over anhydrous sodium sulfate, and the solvent was concentrated under reduced pressure. The residue was subjected to silica gel column chromatography (chloroform→chloroform/methanol=3/1) to afford 2.27 g of the title compound (yield 95%).

$^1$H NMR (400 MHz, CDCl$_3$) δ 1.22-1.34 (m, 1H), 1.50-1.58 (m, 1H), 1.89-1.92 (m, 1H), 1.92-2.06 (m, 1H), 2.43-2.48 (m, 1H), 2.95 (m, 1H), 3.23-3.27 (m, 1H), 3.40-3.42 (m, 2H), 3.71-3.73 (m, 2H), 3.89-3.92 (m, 2H), 4.66 (s, 2H), 5.11 (s, 2H), 5.91 (s, 1H), 7.26-7.52 (m, 10H); MS m/z 443 [M+H]$^+$.

Step 3

Benzyl {2-[({[(2S,5R)-6-benzyloxy-7-oxo-1,6-diazabicyclo[3.2.1]oct-2-yl] carbonyl}amino)oxy] ethyl}carbamate (IV-1-2)

[Chemical Formula 35]

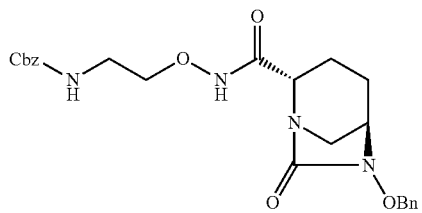

IV-1-2

A solution of (2S,5R)—N-(2-benzyloxycarbonylaminoethoxy)-5-(benzyloxyamino)piperidine-2-carboxamide (642 mg, 1.451 mmol) in acetonitrile (66 mL) was ice cooled, and triethylamine (709 μL) and chlorotrimethylsilane (203 μL) were added, followed by stirring for 1 hour. To this reaction solution was added diphosgene (105 μL), followed by stirring at the same temperature for 20 minutes. Then, to this reaction solution was added 4-(dimethylamino) pyridine (18 mg), and the temperature was elevated to room temperature, followed by stirring overnight. The reaction mixture was concentrated under reduced pressure, the resulting residue was diluted with ethyl acetate and washed sequentially with water, 5% citric acid, 6.5% sodium bicarbonate and saturated brine, the organic layer was dried over anhydrous magnesium sulfate, and the solvent was distilled off under reduced pressure. The resulting residue was purified by silica gel column chromatography (n-hexane/ethyl acetate=1/3) to afford 407 mg of the title compound (yield 60%).

$^1$H NMR (400 MHz, CDCl$_3$) δ 1.59-1.65 (m, 1H), 1.91-2.02 (m, 2H), 2.26-2.31 (m, 1H), 2.71-2.74 (d, J=11.6 Hz, 1H), 2.99-3.02 (br.d, J=11.2 Hz, 1H), 3.28 (s, 1H), 3.31-3.39 (m, 1H), 3.46-3.49 (m, 1H), 3.88-3.97 (m, 3H), 4.88-4.91 (d, J=11.6 Hz, 1H), 5.03-5.06 (d, J=11.6 Hz, 1H), 5.11 (s, 2H), 5.83 (br.s., 1H), 7.27-7.43 (m, 10H), 9.36 (br.s., 1H); MS m/z 469 [M+H]$^+$.

Step 4 tert-Butyl {2-[({[(2S,5R)-6-hydroxy-7-oxo-1,6-diazabicyclo[3.2.1]oct-2-yl] carbonyl}amino)oxy]ethyl}carbamate (V-1)

Benzyl {2-[({[(2S,5R)-6-benzyloxy-7-oxo-1,6-diazabicyclo[3.2.1]oct-2-yl] carbonyl}amino)oxy]ethyl}carbamate (468 mg, 1.00 mmol) and di-tert-butoxycarbonyl dicarbonate (240 mg) were dissolved in tetrahydrofuran (6.6 mL), and 10% Pd/C (93 mg, 50% wet) was added, followed by vigorous stirring under an hydrogen atmosphere for 3 hours. TLC confirmed the end point, and the catalyst was filtered through a Celite pad. The filtrate was concentrated under reduced pressure to afford 403.7 mg of the title compound (quantitative). Instrumental data were consistent with those of Reference Example 3, Step 2.

Reference Example 6

(2S,5R)—N-[2-(Methylamino)ethoxy]-7-oxo-6-(sulfooxy)-1,6-diazabicyclo[3.2.1]octane-2-carboxamide (VI-2)

Step 1 tert-Butyl {2-[({[(2S,5R)-6-benzyloxy-7-oxo-1,6-diazabicyclo[3.2.1]oct-2-yl] carbonyl}amino)oxy]ethyl}(methyl)carbamate (IV-2)

In a similar manner to Reference Example 3, (2S,5R)-6-(benzyloxy)-7-oxo-1,6-diazabicyclo[3.2.1]octane-2-carboxylic acid (390 mg, 1.41 mmol) and tert-butyl (2-(aminooxy)ethyl)(methyl)carbamate (436 mg) gave 347.8 mg of the title compound (yield 55%).

$^1$H NMR (400 MHz, CDCl$_3$) δ 1.46 (s, 9H), 1.58-1.70 (m, 1H), 1.88-2.07 (m, 2H), 2.25-2.36 (m, 1H), 2.70-3.08 (m, 2H), 2.88 (s, 3H), 3.23-3.41 (m, 2H), 3.51-3.68 (m, 1H), 3.83-4.10 (m, 3H), 4.90 (d, J=11.4 Hz, 1H), 5.06 (d, J=11.4 Hz, 1H), 7.32-7.47 (m, 5H), 10.11 (br s, 1H); MS m/z 449 [M+H]$^+$.

Step 2 tert-Butyl {2-[({[(2S,5R)-6-hydroxy-7-oxo-1,6-diazabicyclo[3.2.1]oct-2-yl] carbonyl}amino)oxy]ethyl}(methyl)carbamate (V-2)

In a similar manner to Reference Example 3, the total amount of the compound in Step 1 above gave the title compound (quantitative).

$^1$H NMR (400 MHz, CD$_3$OD) δ 1.46 (s, 9H), 1.73-1.83 (m, 1H), 1.86-2.00 (m, 1H), 2.01-2.13 (m, 1H), 2.14-2.28 (m, 1H), 2.93 (s, 3H), 3.04 (d, J=10.8 Hz, 1H), 3.08-3.18 (m, 1H), 3.43-3.55 (m, 2H), 3.65-3.72 (m, 1H), 3.79-3.88 (m, 1H), 3.92-4.05 (m, 2H); MS m/z 359 [M+H]$^+$.

Step 3

(2S,5R)—N-[2-(Methylamino)ethoxy]-7-oxo-6-(sulfooxy)-1,6-diazabicyclo[3.2.1]octane-2-carboxamide (VI-2)

In a similar manner to Reference Example 3, the total amount of the compound in Step 2 above gave tetrabutylammonium tert-butyl {2-[({[(2S,5R)-7-oxo-6-(sulfooxy)-1,6-diazabicyclo[3.2.1]oct-2-yl]carbonyl}amino)oxy]ethyl} (methyl)carbamate (quantitative).

$^1$H NMR (400 MHz, CDCl$_3$) δ 1.01 (t, J=7.2 Hz, 12H), 1.36-1.53 (m, 8H), 1.47 (s, 9H), 1.57-1.77 (m, 9H), 1.83-1.98 (m, 1H), 2.13-2.25 (m, 1H), 2.28-2.40 (m, 1H), 2.82-2.96 (m, 4H), 3.22-3.42 (m, 11H), 3.60-4.08 (m, 3H), 4.34 (br.s., 1H), 10.15 (br.s., 1H); MS m/z 437 [M-Bu$_4$N]$^-$.

The total amount of the tetrabutylammonium salt above was deprotected with trifluoroacetic acid and purified by octadecyl silica gel column chromatography, and then 149.4 mg of the title compound was afforded (3 step yield 57%).

$^1$H NMR (500 MHz, D$_2$O) δ 1.73-1.97 (m, 2H), 1.98-2.07 (m, 1H), 2.08-2.18 (m, 1H), 2.74 (s, 3H), 3.09 (d, J=12.0 Hz, 1H), 3.21-3.32 (m, 3H), 4.04 (dd, J=7.5, 2.0 Hz, 1H), 4.10-4.23 (m, 3H); MS m/z 337 [M-H]$^-$.

Reference Example 7

(2S,5R)-7-Oxo-N-[2-(propan-2-ylamino)ethoxy]-6-(sulfooxy)-1,6-diazabicyclo [3.2.1]octane-2-carboxamide (VI-3)

Step 1 tert-Butyl {2-[({[(2S,5R)-6-benzyloxy-7-oxo-1,6-diazabicyclo[3.2.1]oct-2-yl] carbonyl}amino)oxy]ethyl}(propan-2-yl)carbamate (IV-3)

A solution of (2S,5R)-6-(benzyloxy)-7-oxo-1,6-diazabicyclo[3.2.1]octane-2-carboxylic acid (414 mg, 1.50 mmol) in dehydrated dichloromethane (14.1 mL) was cooled under an argon atmosphere to 0° C., isobutyl chloroformate (245.9 mg) was slowly added so as not to exceed 0° C. Triethylamine (197 mg) was then slowly added so as not to exceed 0° C., followed by stirring for 30 minutes, and thus mixed acid anhydride was prepared in the reaction system. To this reaction mixture was slowly added tert-butyl (2-(aminooxy)ethyl)(isopropyl) carbamate (596 mg). After the completion of the introduction, the temperature was elevated to room temperature, followed by stirring for 1 hour. This reaction mixture was washed sequentially with 0.5 M hydrochloric acid and saturated brine, the organic layer was dried over magnesium sulfate, and subsequently the residue resulted from distillation off under reduced pressure was subjected to silica gel column chromatography to afford 578.4 mg of the title compound (yield 81%).

$^1$H NMR (400 MHz, CDCl$_3$) δ 1.15 (d, J=6.8 Hz, 6H), 1.46 (s, 9H), 1.55-1.70 (m, 1H), 1.89-2.07 (m, 2H), 2.25-2.37 (m, 1H), 2.73-2.90 (m, 1H), 2.98-3.08 (m, 1H), 3.22-3.38 (m, 2H), 3.40-3.60 (m, 1H), 3.83-4.06 (m, 4H), 4.90 (d,

J=11.2 Hz, 1H), 5.06 (d, J=11.2 Hz, 1H), 7.35-7.46 (m, 5H), 10.29 (br.s., 1H); MS m/z 477 [M+H]⁺.

Step 2 tert-Butyl {2-[({[(2S,5R)-6-hydroxy-7-oxo-1,6-diazabicyclo[3.2.1]oct-2-yl] carbonyl}amino)oxy]ethyl} (propan-2-yl)carbamate (V-3)

In a similar manner to Reference Example 3, the total amount of the compound in Step 1 above gave the title compound (quantitative).
¹H NMR (400 MHz, CD₃OD) δ 1.09-1.23 (m, 6H), 1.46 (s, 9H), 1.73-2.27 (m, 4H), 3.06 (d, J=11.6 Hz, 1H), 3.08-3.50 (m, 4H), 3.64-3.73 (m, 1H), 3.79-3.98 (m, 3H); MS m/z 387 [M+H]⁺.

Step 3

(2S,5R)-7-Oxo-N-[2-(propan-2-ylamino)ethoxy]-6-(sulfooxy)-1,6-diazabicyclo [3.2.1]octane-2-carboxamide (VI-3)

In a similar manner to Reference Example 3, the total amount of the compound in Step 2 above gave tetrabutylammonium tert-butyl {2-[({[(2S,5R)-7-oxo-6-(sulfooxy)-1, 6-diazabicyclo[3.2.1]oct-2-yl]carbonyl}amino)oxy]ethyl} (propan-2-yl)carbamate (quantitative).
¹H NMR (400 MHz, CDCl₃) δ 1.01 (d, J=7.4 Hz, 12H), 1.10-1.20 (m, 6H), 1.33-1.77 (m, 17H), 1.46 (s, 9H), 1.84-1.97 (m, 1H), 2.12-2.25 (m, 1H), 2.28-2.40 (m, 1H), 2.79-2.95 (m, 1H), 3.17-3.45 (m, 9H), 3.50-3.67 (m, 1H), 3.80-4.07 (m, 5H), 4.34 (br.s., 1H), 10.36 (br.s., 1H); MS m/z 465 [M-Bu₄N]⁻.

The total amount of the tetrabutylammonium salt above was deprotected with trifluoroacetic acid and purified by octadecyl silica gel column chromatography, and then 252.1 mg of the title compound was afforded (3 step yield 57%).
¹H NMR (500 MHz, D₂O) δ 1.28 (d, J=6.5 Hz, 6H), 1.74-1.83 (m, 1H), 1.85-1.96 (m, 1H), 1.98-2.14 (m, 2H), 3.11 (d, J=12.5 Hz, 1H), 3.22-3.30 (m, 3H), 3.40 (quint, J=6.5 Hz, 1H), 4.01 (br d, J=5.5 Hz, 1H), 4.09-4.18 (m, 3H); MS m/z 367 [M+H]⁺.

Reference Example 8

(2S,5R)—N-[2-(Dimethylamino)ethoxy]-7-oxo-6-(sulfooxy)-1,6-diazabicyclo[3.2.1]octane-2-carboxamide (VI-4)

Step 1

(2S,5R)-6-Benzyloxy-N-[2-(dimethylamino)ethoxy]-7-oxo-1,6-diazabicyclo[3.2.1]octane-2-carboxamide (IV-4)

A solution of (2S,5R)-6-(benzyloxy)-7-oxo-1,6-diazabicyclo[3.2.1]octane-2-carboxylic acid (553 mg, 2.00 mmol) in dehydrated dichloromethane (10 mL) was cooled under an argon atmosphere to 0° C., and isobutyl chloroformate (289 μL, 2.20 mmol) was added dropwise. Triethylamine (293 μL) was then added, followed by stirring for 30 minutes, and thus mixed acid anhydride was prepared in the reaction system. To this reaction mixture were slowly added 2-(aminooxy)-N,N-dimethylethanamine dihydrochloride (591 mg) and triethylamine (930 μL) while washing with dehydrated dichloromethane (7.0 mL), followed by stirring at such temperature for 1 hour. After this reaction mixture was filtered, the residue was washed with methanol and the filtrate was concentrated under reduced pressure. The resulting residue was dissolved in dichloromethane and water, and the organic layer resulted from extraction with dichloromethane was dried over magnesium sulfate and then distilled off under reduced pressure. The resulting residue was subjected to silica gel column chromatography (amino silica, chloroform/methanol=10/1) to afford 291.1 mg of the title compound as a colorless oil. (yield 40%)
¹H NMR (400 MHz, CDCl₃) δ 1.45-1.85 (m, 4H), 2.29 (s, 6H), 2.60 (t, J=5.2 Hz, 2H), 2.81 (d, J=11.6 Hz, 1H), 2.97 (br.d., J=11.6 Hz, 1H), 3.28-3.34 (m, 1H), 3.92-4.07 (m, 3H), 4.90 (d, J=11.6 Hz, 1H), 5.05 (d, J=11.6 Hz, 1H), 7.35-7.48 (m, 5H); MS m/z 363 [M+H]⁺.

Step 2

(2S,5R)—N-[2-(Dimethylamino)ethoxy]-6-hydroxy-7-oxo-1,6-diazabicyclo[3.2.1]octane-2-carboxamide (V-4)

In a similar manner to Reference Example 3, the total amount of the compound in Step 1 above gave the title compound (quantitative).
¹H NMR (400 MHz, CDCl₃) δ 1.74-1.84 (m, 1H), 1.87-1.98 (m, 1H), 2.03-2.12 (m, 1H), 2.15-2.24 (m, 1H), 2.36 (s, 6H), 2.67-2.74 (m, 2H), 3.07 (br.d., J=11.6 Hz, 1H), 3.12 (br.d., J=11.6 Hz, 1H), 3.67-3.72 (m, 1H), 3.83 (br.d., J=6.4 Hz, 1H), 3.96-4.06 (m, 2H); MS m/z 273 [M+H]⁺.

Step 3

(2S,5R)—N-[2-(Dimethylamino)ethoxy]-7-oxo-6-(sulfooxy)-1,6-diazabicyclo[3.2.1]octane-2-carboxamide (VI-4)

The reaction mixture resulted from a similar manner to Reference Example 3 was diluted with chloroform and washed with water to afford pyridinium (2S,5R)—N-[2-(dimethylamino)ethoxy]-7-oxo-6-(sulfooxy)-1,6-diazabicyclo[3.2.1]octane-2-carboxamide. Neutralization with saturated sodium bicarbonate aqueous solution and subsequent purification by octadecyl silica gel column chromatography gave 130.7 mg of the title compound (2 step yield 43%).
¹H NMR (400 MHz, D₂O) δ 1.68-1.84 (m, 2H), 1.86-2.04 (m, 2H), 2.80 (s, 6H), 3.09-3.17 (m, 2H), 3.17-3.29 (m, 2H), 3.80-3.90 (m, 1H), 4.02-4.13 (m, 3H); MS m/z 353 [M+H]⁺.

Reference Example 9

(2S,5R)—N-{[(2S)-2-Aminopropyl]oxy}-7-oxo-6-(sulfooxy)-1,6-diazabicyclo[3.2.1]octane-2-carboxamide (VI-5)

Step 1 tert-Butyl {(2S)-1-[({[(2S,5R)-6-benzyloxy-7-oxo-1, 6-diazabicyclo[3.2.1]oct-2-yl]carbonyl}amino)oxy] propan-2-yl}carbamate (IV-5)

In a similar manner to Reference Example 7, (2S,5R)-6-(benzyloxy)-7-oxo-1,6-diazabicyclo[3.2.1]octane-2-carboxylic acid (414 mg, 1.50 mmol) and (S)-tert-butyl (1-(aminooxy)propan-2-yl)carbamate (550 mg) gave 585.6 mg of the title compound (yield 87%).

¹H NMR (400 MHz, CDCl₃) δ 1.17 (d, J=6.4 Hz, 3H), 1.44 (s, 9H), 1.55-1.70 (m, 1H), 1.90-2.10 (m, 2H), 2.26-2.34 (m, 1H), 2.80 (d, J=12.0 Hz, 1H), 3.06 (br.d., J=12.0 Hz, 1H), 3.27-3.34 (m, 1H), 3.64-3.74 (m, 1H), 3.86-3.98 (m, 3H), 4.81 (br.d., J=7.6 Hz, 1H), 4.90 (d, J=11.6 Hz, 1H), 5.05 (d, J=11.6 Hz, 1H), 7.34-7.45 (m, 5H), 9.68 (br.s., 1H); MS m/z 449 [M+H]⁺.

Step 2 tert-Butyl (2S)-1-[({[(2S,5R)-6-hydroxy-7-oxo-1,6-diazabicyclo[3.2.1]oct-2-yl]carbonyl}amino)oxy]propan-2-yl}carbamate (V-5)

In a similar manner to Reference Example 3, the total amount of the compound in Step 1 above gave the title compound (quantitative).

¹H NMR (400 MHz, CD₃OD) δ 1.16 (d, J=6.4 Hz, 3H), 1.44 (s, 9H), 1.74-1.84 (m, 1H), 1.86-1.98 (m, 1H), 2.03-2.12 (m, 1H), 2.21 (br.dd., J=15.2, 6.8 Hz, 1H), 3.06 (d, J=12.0 Hz, 1H), 3.14 (br.d., J=12.0 Hz, 1H), 3.68-3.72 (m, 1H), 3.74-3.87 (m, 4H); MS m/z 359 [M+H]⁺.

Step 3

(2S,5R)—N-{[(2S)-2-Aminopropyl]oxy}-7-oxo-6-(sulfooxy)-1,6-diazabicyclo[3.2.1]octane-2-carboxamide (VI-5)

In a similar manner to Reference Example 3, the total amount of the compound in Step 2 above gave tetrabutylammonium tert-butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate (quantitative). MS m/z 437[M-Bu₄N]⁻.

The total amount of the tetrabutylammonium salt above was deprotected with trifluoroacetic acid and purified by octadecyl silica gel column chromatography, and then 117.1 mg of the title compound was afforded (3 step yield 26%).

¹H NMR (400 MHz, D₂O) δ 1.17 (d, J=6.8 Hz, 3H), 1.66-1.89 (m, 2H), 1.91-2.08 (m, 2H), 3.02 (d, J=12.0 Hz, 1H), 3.18 (br.d., J=12.0 Hz, 1H), 3.47-3.58 (m, 1H), 3.82 (dd, J=11.8, 9.4 Hz, 1H), 3.92-4.02 (m, 2H), 4.05-4.10 (m, 1H); MS m/z 339 [M+H]⁺.

Reference Example 10

(2S,5R)—N-{[(2R)-2-Aminopropyl]oxy}-7-oxo-6-(sulfooxy)-1,6-diazabicyclo[3.2.1]octane-2-carboxamide (VI-6)

Step 1 tert-Butyl {(2R)-1-[({[(2S,5R)-6-benzyloxy-7-oxo-1,6-diazabicyclo[3.2.1] oct-2-yl]carbonyl}amino)oxy]propan-2-yl}carbamate (IV-6)

In a similar manner to Reference Example 7, (2S,5R)-6-(benzyloxy)-7-oxo-1,6-diazabicyclo[3.2.1]octane-2-carboxylic acid (414 mg, 1.50 mmol) and (R)-tert-butyl (1-(aminooxy)propan-2-yl)carbamate (569 mg) gave 625 mg of the title compound (yield 93%).

¹H NMR (400 MHz, CDCl₃) δ 1.14 (d, J=6.4 Hz, 3H), 1.43 (s, 9H), 1.53-1.70 (m, 1H), 1.90-2.06 (m, 2H), 2.28-2.36 (m, 1H), 2.79 (d, J=12.0 Hz, 1H), 3.02 (br.d., J=12.0 Hz, 1H), 3.28-3.33 (m, 1H), 3.56-3.68 (m, 1H), 3.84 (dd, J=11.2, 3.6 Hz, 1H), 3.92-4.04 (m, 2H), 4.66 (br d, J=8.0 Hz, 1H), 4.91 (d, J=11.2 Hz, 1H), 5.06 (d, J=11.2 Hz, 1H), 7.35-7.45 (m, 5H), 9.94 (br.s., 1H); MS m/z 449 [M+H]⁺.

Step 2 tert-Butyl {(2R)-1-[({[(2S,5R)-6-hydroxy-7-oxo-1,6-diazabicyclo[3.2.1]oct-2-yl]carbonyl}amino)oxy]propan-2-yl}carbamate (V-6)

In a similar manner to Reference Example 3, the total amount of the compound in Step 1 above gave the title compound (quantitative).

¹H NMR (400 MHz, CD₃OD) δ 1.15 (d, J=6.4 Hz, 3H), 1.44 (s, 9H), 1.73-1.84 (m, 1H), 1.86-2.00 (m, 1H), 2.01-2.12 (m, 1H), 2.19-2.29 (m, 1H), 3.06 (d, J=11.6 Hz, 1H), 3.10-3.20 (m, 1H), 3.67-3.72 (m, 1H), 3.73-3.92 (m, 4H); MS m/z 359 [M+H]⁺.

Step 3

(2S,5R)—N-{[(2R)-2-aminopropyl]oxy}-7-oxo-6-(sulfooxy)-1,6-diazabicyclo[3.2.1]octane-2-carboxamide (VI-6)

In a similar manner to Reference Example 3, the total amount of the compound in Step 2 above gave tetrabutylammonium tert-butyl {(2R)-1-[({[(2S,5R)-7-oxo-6-(sulfooxy)-1,6-diazabicyclo[3.2.1]oct-2-yl]carbonyl}amino)oxy]propan-2-yl}carbamate (quantitative). MS m/z 437[M-Bu₄N]⁻.

The total amount of the tetrabutylammonium salt above was deprotected with trifluoroacetic acid and purified by octadecyl silica gel column chromatography, and then 212.6 mg of the title compound was afforded (3 step yield 45%).

¹H NMR (400 MHz, D₂O) δ 1.17 (d, J=6.8 Hz, 3H), 1.66-1.78 (m, 1H), 1.78-1.88 (m, 1H), 1.90-2.06 (m, 2H), 3.02 (d, J=12.0 Hz, 1H), 3.18 (br.d., J=12.0 Hz, 1H), 3.48-3.58 (m, 1H), 3.83 (dd, J=11.8, 9.0 Hz, 1H), 3.94 (br.d., J=7.2 Hz, 1H), 3.98 (dd, J=11.8, 3.4 Hz, 1H), 4.06-4.10 (m, 1H); MS m/z 339 [M+H]⁺.

Reference Example 11

(2S,5R)—N-(3-aminopropoxy)-7-oxo-6-(sulfooxy)-1,6-diazabicyclo[3.2.1] octane-2-carboxamide (VI-7)

Step 1 tert-Butyl {3-[({[(2S,5R)-6-benzyloxy-7-oxo-1,6-diazabicyclo[3.2.1]oct-2-yl] carbonyl}amino)oxy]propyl}carbamate (IV-7)

In a similar manner to Reference Example 3, (2S,5R)-6-(benzyloxy)-7-oxo-1,6-diazabicyclo[3.2.1]octane-2-carboxylic acid (390 mg, 1.41 mmol) and tert-butyl (3-(aminooxy)propyl)carbamate (730 mg) gave 398.1 mg of the title compound (yield 63%).

¹H NMR (400 MHz, CDCl₃) δ 1.44 (s, 9H), 1.50-1.67 (m, 1H), 1.75-1.86 (m, 2H), 1.88-2.07 (m, 2H), 2.28-2.37 (m, 2H), 2.77 (d, J=11.0 Hz, 1H), 3.01 (br.d., J=11.0 Hz, 1H), 3.20-3.38 (m, 3H), 3.89-4.04 (m, 3H), 4.90 (d, J=11.4 Hz,

1H), 5.05 (d, J=11.4 Hz, 1H), 5.17 (br.s., 1H), 7.36-7.45 (m, 5H), 9.21 (br.s., 1H); MS m/z 449 [M+H]$^+$.

Step 2 tert-Butyl {3-[({[(2S,5R)-6-hydroxy-7-oxo-1,6-diazabicyclo[3.2.1]oct-2-yl] carbonyl}amino)oxy]propyl}carbamate (V-7)

In a similar manner to Reference Example 3, the compound in Step 1 above (392.8 mg, 876 μmol) gave the title compound (quantitative).
$^1$H NMR (400 MHz, CD$_3$OD) δ 1.43 (s, 9H), 1.73-1.99 (m, 4H), 2.01-2.12 (m, 1H), 2.13-2.24 (m, 1H), 3.07 (d, J=11.6 Hz, 1H), 3.09-3.21 (m, 3H), 3.69 (br.s., 1H), 3.80-3.96 (m, 3H); MS m/z 359 [M+H]$^+$.

Step 3

(2S,5R)—N-(3-aminopropoxy)-7-oxo-6-(sulfooxy)-1,6-diazabicyclo[3.2.1] octane-2-carboxamide (VI-7)

In a similar manner to Reference Example 3, the total amount of the compound in Step 2 above gave tetrabutylammonium tert-butyl {34({[(2S,5R)-7-oxo-6-(sulfooxy)-1,6-diazabicyclo[3.2.1]oct-2-yl]carbonyl}amino)oxy]propyl}carbamate (quantitative).
$^1$H NMR (400 MHz, CDCl$_3$) δ 1.01 (t, J=7.4 Hz, 12H), 1.33-1.53 (m, 8H), 1.47 (s, 9H), 1.55-1.96 (m, 12H), 2.14-2.23 (m, 1H), 2.31-2.41 (m, 1H), 2.85 (br.d., J=11.2 Hz, 1H), 3.15-3.42 (m, 11H), 3.88-4.07 (m, 3H), 4.35 (br.s., 1H), 5.27 (br s, 1H), 9.26 (br.s., 1H); MS m/z 437 [M-Bu$_4$N]$^-$.

The total amount of the tetrabutylammonium salt above was deprotected with trifluoroacetic acid and purified by octadecyl silica gel column chromatography, and then 138.4 mg of the title compound was afforded (3 step yield 47%).
$^1$H NMR (400 MHz, D$_2$O) δ 1.67-2.05 (m, 6H), 3.00-3.19 (m, 4H), 3.82-3.94 (m, 3H), 4.05-4.10 (m, 1H); MS m/z 337 [M-H]$^-$.

Reference Example 12

(2S,5R)—N-[(2S)-Azetidin-2-ylmethoxy]-7-oxo-6-(sulfooxy)-1,6-diazabicyclo[3.2.1]octane-2-carboxamide (VI-8)

Step 1 tert-Butyl (2S)-2-{[({[(2S,5R)-6-benzyloxy-7-oxo-1,6-diazabicyclo[3.2.1]oct-2-yl]carbonyl}amino)oxy]methyl}azetidine-1-carboxylate (IV-8)

In a similar manner to Reference Example 7, (2S,5R)-6-(benzyloxy)-7-oxo-1,6-diazabicyclo[3.2.1]octane-2-carboxylic acid (553 mg, 2.00 mmol) and (S)-tert-butyl 2-((aminooxy)methyl)azetidine-1-carboxylate (578 mg) gave 760.1 mg of the title compound (yield 83%).
$^1$H NMR (400 MHz, CDCl$_3$) δ 1.46 (s, 9H), 1.56-1.70 (m, 1H), 1.88-2.07 (m, 3H), 2.23-2.34 (m, 2H), 2.84 (d, J=11.6 Hz, 1H), 3.02 (d, J=11.6 Hz, 1H), 3.28 (br s, 1H), 3.77-4.03 (m, 4H), 4.06-4.15 (m, 1H), 4.37-4.48 (m, 1H), 4.89 (d, J=11.6 Hz, 1H), 5.04 (d, J=11.6 Hz, 1H), 7.34-7.44 (m, 5H), 10.63 (br.s., 1H); MS m/z 461 [M+H]$^+$.

Step 2 tert-Butyl (2S)-2-{[({[(2S,5R)-6-hydroxy-7-oxo-1,6-diazabicyclo[3.2.1]oct-2-yl]carbonyl}amino)oxy]methyl}azetidine-1-carboxylate (V-8)

In a similar manner to Reference Example 3, the compound in Step 1 above (699 mg, 1.52 mmol) gave the title compound (quantitative).
$^1$H NMR (400 MHz, CD$_3$OD) δ 1.44 (s, 9H), 1.74-1.85 (m, 1H), 1.86-1.99 (m, 1H), 2.02-2.14 (m, 1H), 2.16-2.40 (m, 3H), 3.06 (d, J=11.6 Hz, 1H), 3.10-3.17 (m, 1H), 3.67-3.74 (m, 1H), 3.75-3.93 (m, 3H), 4.01 (dd, J=10.6, 10.6 Hz, 1H), 4.14 (dd, J=10.6, 10.6 Hz, 1H), 4.37-4.47 (m, 1H); MS m/z 371 [M+H]$^+$.

Step 3

(2S,5R)—N-[(2S)-Azetidin-2-ylmethoxy]-7-oxo-6-(sulfooxy)-1,6-diazabicyclo[3.2.1]octane-2-carboxamide (VI-8)

In a similar manner to Reference Example 3, the total amount of the compound in Step 2 above gave tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}azetidine-1-carboxylate (quantitative).
$^1$H NMR (400 MHz, CDCl$_3$) δ 1.01 (t, J=7.2 Hz, 12H), 1.30-2.10 (m, 19H), 1.46 (s, 9H), 2.12-2.39 (m, 3H), 2.89 (br.d., J=12.0 Hz, 1H), 3.23-3.39 (m, 9H), 3.76-3.93 (m, 3H), 3.95-4.06 (m, 1H), 4.08-4.18 (m, 1H), 4.33 (br.s., 1H), 4.37-4.50 (m, 1H); MS m/z 449 [M-Bu$_4$N]$^-$.

The total amount of the tetrabutylammonium salt above was deprotected with trifluoroacetic acid and purified by octadecyl silica gel column chromatography, and then 172.3 mg of the title compound was afforded (3 step yield 32%).
$^1$H NMR (500 MHz, D$_2$O) δ 1.71-1.83 (m, 1H), 1.84-1.97 (m, 1H), 1.98-2.16 (m, 2H), 2.36-2.49 (m, 1H), 2.50-2.61 (m, 1H), 3.10 (d, J=12.0 Hz, 1H), 3.22-3.30 (m, 1H), 3.92-4.12 (m, 5H), 4.25-4.36 (m, 1H), 4.68-4.77 (m, 1H); MS m/z 351 [M+H]$^+$.

Reference Example 13

(2S,5R)-7-Oxo-N-[(2R)-pyrrolidine-2-ylmethoxy]-6-(sulfooxy)-1,6-diazabicyclo[3.2.1]octane-2-carboxamide (VI-9)

Step 1 tert-Butyl (2R)-2-{[({[(2S,5R)-6-benzyloxy-7-oxo-1,6-diazabicyclo[3.2.1]oct-2-yl]carbonyl}amino)oxy]methyl}pyrrolidine-1-carboxylate (IV-9)

In a similar manner to Reference Example 3, (2S,5R)-6-(benzyloxy)-7-oxo-1,6-diazabicyclo[3.2.1]octane-2-carboxylic acid (390 mg, 1.41 mmol) and (R)-tert-butyl 2-((aminooxy)methyl)pyrrolidine-1-carboxylate (796 mg) gave 336 mg of the title compound (yield 50%).
$^1$H NMR (400 MHz, CDCl$_3$) δ 1.45 (s, 9H), 1.52-1.72 (m, 1H), 1.80-2.09 (m, 6H), 2.27-2.39 (m, 1H), 2.84 (br.d., J=12.4 Hz, 1H), 2.96-3.08 (m, 1H), 3.28-3.44 (m, 3H), 3.60-3.86 (m, 2H), 3.89-4.06 (m, 1H), 4.14-4.29 (m, 1H), 4.90 (d, J=11.2 Hz, 1H), 5.06 (d, J=11.2 Hz, 1H), 7.32-7.47 (m, 5H), 10.56 (s, 1H); MS m/z 475 [M+H]⁺.

Step 2 tert-Butyl (2R)-2-{[({[(2S,5R)-6-hydroxy-7-oxo-1,6-diazabicyclo[3.2.1]oct-2-yl]carbonyl}amino)oxy]methyl}pyrrolidine-1-carboxylate (V-9)

In a similar manner to Reference Example 3, the total amount of the compound in Step 1 above gave the title compound (quantitative).
¹H NMR (400 MHz, CD₃OD) δ 1.46 (s, 9H), 1.73-2.27 (m, 8H), 3.06 (d, J=11.6 Hz, 1H), 3.09-3.18 (m, 1H), 3.24-3.40 (m, 2H), 3.67-3.71 (m, 1H), 3.73-4.12 (m, 4H); MS m/z 385 [M+H]⁺.

Step 3

(2S,5R)-7-Oxo-N-[(2R)-pyrrolidin-2-ylmethoxy]-6-(sulfooxy)-1,6-diazabicyclo[3.2.1]octane-2-carboxamide (VI-9)

In a similar manner to Reference Example 3, the total amount of the compound in Step 2 above gave tetrabutylammonium tert-butyl (2R)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate (quantitative).
¹H NMR (400 MHz, CDCl₃) δ 1.01 (t, J=7.4 Hz, 12H), 1.34-1.51 (m, 8H), 1.46 (s, 9H), 1.55-1.78 (m, 10H), 1.80-2.01 (m, 4H), 2.11-2.23 (m, 1H), 2.29-2.42 (m, 1H), 2.88 (br.d., J=11.2 Hz, 1H), 3.21-3.43 (m, 10H), 3.60-3.86 (m, 2H), 3.88-4.07 (m, 2H), 4.16-4.28 (m, 1H), 4.34 (br.s., 1H), 10.62 (br s, 1H); MS m/z 463 [M-Bu₄N+2H]⁺.
The total amount of the tetrabutylammonium salt above was deprotected with trifluoroacetic acid and purified by octadecyl silica gel column chromatography, and then 77.4 mg of the title compound was afforded (3 step yield 30%).
¹H NMR (500 MHz, D₂O) δ 1.66-2.18 (m, 8H), 3.14 (d, J=12.8 Hz, 1H), 3.23 (br.d., J=12.8 Hz, 1H), 3.30 (t, J=7.3 Hz, 2H), 3.89 (ddd, J=8.2, 8.2, 3.4 Hz, 1H), 3.92-4.01 (m, 2H), 4.09-4.18 (m, 2H); MS m/z 365 [M+H]⁺.

Reference Example 14

(2S,5R)-7-oxo-N-[(3R)-piperidin-3-ylmethoxy]-6-(sulfooxy)-1,6-diazabicyclo[3.2.1]octane-2-carboxamide (VI-10)

Step 1 tert-Butyl (3R)-3-{[({[(2S,5R)-6-benzyloxy-7-oxo-1,6-diazabicyclo[3.2.1]oct-2-yl]carbonyl}amino)oxy]methyl}piperidine-1-carboxylate (IV-10)

In a similar manner to Reference Example 7, (2S,5R)-6-(benzyloxy)-7-oxo-1,6-diazabicyclo[3.2.1]octane-2-carboxylic acid (390 mg, 1.41 mmol) and (R)-tert-butyl 3-((aminooxy)methyl)piperidine-1-carboxylate (527 mg) gave 333 mg of the title compound (yield 48%).
¹H NMR (400 MHz, CDCl₃) δ 1.15-2.10 (m, 8H), 1.45 (s, 9H), 2.25-2.40 (m, 1H), 2.70-3.08 (m, 4H), 3.27-3.37 (m, 1H), 3.65-4.00 (m, 5H), 4.90 (d, J=11.2 Hz, 1H), 5.05 (d, J=11.2 Hz, 1H), 7.34-7.46 (m, 5H), 9.22 (br.s., 1H); MS m/z 489 [M+H]⁺.

Step 2 tert-Butyl (3R)-3-{[({[(2S,5R)-6-hydroxy-7-oxo-1,6-diazabicyclo[3.2.1]oct-2-yl]carbonyl}amino)oxy]methyl}piperidine-1-carboxylate (V-10)

In a similar manner to Reference Example 3, the total amount of the compound in Step 1 above gave the title compound (quantitative).
¹H NMR (400 MHz, CD₃OD) δ 1.24-1.37 (m, 1H), 1.40-1.56 (m, 1H), 1.45 (s, 9H), 1.64-1.73 (m, 1H), 1.75-2.00 (m, 4H), 2.03-2.13 (m, 1H), 2.15-2.26 (m, 1H), 2.65-2.95 (m, 2H), 3.06 (d, J=12.0 Hz, 1H), 3.13 (br.d., J=12.0 Hz, 1H), 3.67-3.91 (m, 5H), 4.01-4.08 (m, 1H); MS m/z 399 [M+H]⁺.

Step 3

(2S,5R)-7-Oxo-N-[(3R)-piperidin-3-ylmethoxy]-6-(sulfooxy)-1,6-diazabicyclo [3.2.1]octane-2-carboxamide (VI-10)

In a similar manner to Reference Example 3, the total amount of the compound in Step 2 above gave tetrabutylammonium tert-butyl (3R)-2-{[({[(2S,5R)-7-oxo-6-(sulfooxy)-1,6-diazabicyclo[3.2.1]oct-2-yl]carbonyl}amino)oxy]methyl}piperidine-1-carboxylate (quantitative).
¹H NMR (400 MHz, CDCl₃) δ 1.01 (dd, J=7.6 & 6.8 Hz, 12H), 1.11-1.99 (m, 23H), 1.46 (s, 9H), 2.12-2.24 (m, 1H), 2.30-2.42 (m, 1H), 2.67-2.96 (m, 3H), 3.19-3.38 (m, 9H), 3.70-3.99 (m, 5H), 4.35 (br.s., 1H), 9.16 (br.s., 1H); MS m/z 477 [M-Bu₄N]⁻.
The total amount of the tetrabutylammonium salt above was deprotected with trifluoroacetic acid and purified by octadecyl silica gel column chromatography, and then 106 mg of the title compound was afforded (3 step yield 41%).
¹H NMR (400 MHz, D₂O) δ 1.16-1.28 (m, 1H), 1.54-1.88 (m, 5H), 1.92-2.16 (m, 3H), 2.72 (t, J=12.2 Hz, 1H), 2.81 (ddd, J=12.8 & 12.8 & 3.5 Hz, 1H), 3.02 (d, J=12.0 Hz, 1H), 3.15-3.28 (m, 2H), 3.37-3.44 (m, 1H), 3.70 (dd, J=10.3 & 7.6 Hz, 1H), 3.79 (dd, J=10.3 & 5.0 Hz, 1H), 3.88-3.94 (m, 1H), 4.06-4.10 (m, 1H); MS m/z 377 [M–H]⁻.

Reference Example 15

(2S,5R)-7-Oxo-N-[(3S)-pyrrolidin-3-yloxy]-6-(sulfooxy)-1,6-diazabicyclo[3.2.1]octane-2-carboxamide (VI-11)

Step 1 tert-Butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate (IV-11)

In a similar manner to Reference Example 3, (2S,5R)-6-(benzyloxy)-7-oxo-1,6-diazabicyclo[3.2.1]octane-2-carboxylic acid (553 mg, 2.00 mmol) and (S)-tert-butyl 3-(aminooxy)pyrrolidine-1-carboxylate (606 mg) gave 920.4 mg of the title compound (quantitative).
¹H NMR (400 MHz, CDCl₃) δ 1.46 (s, 9H), 1.61-1.68 (m, 1H), 1.89-2.09 (m, 3H), 2.15-2.19 (m, 1H), 2.28-2.34 (m, 1H), 2.75 (d, J=11.6 Hz, 1H), 2.95-3.06 (m, 1H), 3.31 (br s, 1H), 3.35-3.68 (m, 4H), 3.97 (d, J=7.6 Hz, 1H), 4.60 (br.d., J=23.2 Hz, 1H), 4.90 (d, J=11.6 Hz, 1H), 5.05 (d, J=11.6 Hz, 1H), 7.26-7.43 (m, 5H), 9.08 (br.d., J=23.2 Hz, 1H); MS m/z 461 [M+H]⁺.

Step 2 tert-Butyl (3S)-3-[({[(2S,5R)-6-hydroxy-7-oxo-1,6-diazabicyclo[3.2.1]oct-2-yl]carbonyl}amino)oxy]pyrrolidine-1-carboxylate (V-11)

In a similar manner to Reference Example 3, the compound in Step 1 above (869 mg, 1.89 mmol) gave the title compound (quantitative).

$^1$H NMR (400 MHz, CD$_3$OD) δ 1.47 (s, 9H), 1.75-2.12 (m, 4H), 2.13-2.25 (m, 2H), 3.05 (d, J=12.0 Hz, 1H), 3.13 (br.d., J=12.0 Hz, 1H), 3.25-3.50 (m, 2H), 3.61 (br.d., J=13.2 Hz, 1H), 3.70 (br.s., 1H), 3.86 (br d, J=7.2 Hz, 1H), 4.32-4.38 (m, 1H), 4.54-4.62 (m, 1H); MS m/z 371 [M+H]$^+$.

Step 3

(2S,5R)-7-Oxo-N-[(3S)-pyrrolidin-3-yloxy]-6-(sulfooxy)-1,6-diazabicyclo[3.2.1]octane-2-carboxamide (VI-11)

In a similar manner to Reference Example 3, the total amount of the compound in Step 2 above gave tetrabutylammonium tert-butyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate (quantitative). MS m/z 449 [M-Bu$_4$N]$^-$.

The total amount of the tetrabutylammonium salt above was deprotected with trifluoroacetic acid and purified by octadecyl silica gel column chromatography, and then 170.7 mg of the title compound was afforded (3 step yield 26%).

$^1$H NMR (400 MHz, D$_2$O) δ 1.71-1.92 (m, 2H), 1.95-2.18 (m, 3H), 2.21-2.30 (m, 1H), 3.07 (d, J=12.2 Hz, 1H), 3.24 (br.d., J=12.2 Hz, 1H), 3.31-3.45 (m, 3H), 3.51 (d, J=13.6 Hz, 1H), 3.99 (br.d., J=6.0 Hz, 1H), 4.10-4.14 (m, 1H), 4.72-4.77 (m, 1H); MS m/z 349 [M−H]$^-$.

Reference Example 16

(2S,5R)—N-(Azetidin-3-ylmethoxy)-7-oxo-6-(sulfooxy)-1,6-diazabicyclo[3.2.1] octane-2-carboxamide (VI-12)

Step 1 tert-Butyl 3-{[({[(2S,5R)-6-benzyloxy-7-oxo-1,6-diazabicyclo[3.2.1]oct-2-yl] carbonyl}amino)oxy]methyl}azetidine-1-carboxylate (IV-12)

In a similar manner to Reference Example 7, (2S,5R)-6-(benzyloxy)-7-oxo-1,6-diazabicyclo[3.2.1]octane-2-carboxylic acid (553 mg, 2.00 mmol) and tert-butyl 3-((aminooxy)methyl)azetidine-1-carboxylate (564 mg) gave 699.7 mg of the title compound (yield 76%).

$^1$H NMR (400 MHz, CDCl$_3$) δ 1.43 (s, 9H), 1.54-1.70 (m, 1H), 1.87-2.06 (m, 2H), 2.27-2.35 (m, 1H), 2.75 (d, J=11.6 Hz, 1H), 2.80-2.90 (m, 1H), 3.01 (br.d., J=11.6 Hz, 1H), 3.32 (br.s., 1H), 3.68-3.76 (m, 2H), 3.94 (br.d., J=7.6 Hz, 1H), 4.00-4.15 (m, 4H), 4.90 (d, J=11.8 Hz, 1H), 5.05 (d, J=11.8 Hz, 1H), 7.35-7.44 (m, 5H), 9.08 (br s, 1H); MS m/z 461 [M+H]$^+$.

Step 2 tert-Butyl 3-{[({[(2S,5R)-6-hydroxy-7-oxo-1,6-diazabicyclo[3.2.1]oct-2-yl] carbonyl}amino)oxy]methyl}azetidine-1-carboxylate (V-12)

In a similar manner to Reference Example 3, the compound in Step 1 above (642 mg, 1.39 mmol) gave the title compound (quantitative).

$^1$H NMR (400 MHz, CD$_3$OD) δ 1.43 (s, 9H), 1.74-1.85 (m, 1H), 1.86-1.97 (m, 1H), 2.04-2.13 (m, 1H), 2.16-2.24 (m, 1H), 2.84-2.94 (m, 1H), 3.05 (d, J=11.6 Hz, 1H), 3.13 (br.d., J=11.6 Hz, 1H), 3.68-3.82 (m, 3H), 3.83 (br.d., J=6.8 Hz, 1H), 3.97-4.06 (m, 4H); MS m/z 371 [M+H]$^+$.

Step 3

(2S,5R)—N-(azetidin-3-ylmethoxy)-7-oxo-6-(sulfooxy)-1,6-diazabicyclo[3.2.1] octane-2-carboxamide (VI-12)

In a similar manner to Reference Example 3, the total amount of the compound in Step 2 above gave tetrabutylammonium tert-butyl 3-{[({[(2S,5R)-7-oxo-6-(sulfooxy)-1,6-diazabicyclo[3.2.1]oct-2-yl]carbonyl}amino)oxy]methyl}azetidine-1-carboxylate (quantitative).

$^1$H NMR (400 MHz, CDCl$_3$) δ 1.01 (t, J=7.2 Hz, 12H), 1.37-1.51 (m, 8H), 1.46 (s, 9H), 1.54-1.75 (m, 9H), 1.82-1.97 (m, 1H), 2.13-2.25 (m, 1H), 2.29-2.40 (m, 1H), 2.77-2.95 (m, 2H), 3.24-3.40 (m, 9H), 3.64-4.16 (m, 7H), 4.36 (br.s., 1H), 9.16 (br.s., 1H); MS m/z 449 [M-Bu$_4$N]$^-$.

The total amount of the tetrabutylammonium salt above was deprotected with trifluoroacetic acid and purified by octadecyl silica gel column chromatography, and then 164.7 mg of the title compound was afforded (3 step yield 34%).

$^1$H NMR (400 MHz, D$_2$O) δ 1.65-1.89 (m, 2H), 1.92-2.06 (m, 2H), 3.06 (d, J=12.4 Hz, 1H), 3.10-3.22 (m, 2H), 3.90-4.00 (m, 5H), 4.07-4.14 (m, 3H); MS m/z 351 [M+H]$^+$.

Reference Example 17

(2S,5R)—N-Benzyl-6-(benzyloxy)-7-oxo-1,6-diazabicyclo[3.2.1]octane-2-carboxamide (10)

Step 1 tert-Butyl (2S,5R)-2-(benzylcarbamoyl)-5-((benzyloxy)amino)piperidine-1-carboxylate (8)

(2S,5R)—N-Benzyl-5-((benzyloxy)amino)piperidine-2-carboxamide (808 mg, 2.38 mmol) was dissolved in methanol (8 mL), and triethylamine (288 mg) and di-tert-butyl dicarbonate (571 mg) were added under ice cooling, followed by stirring at room temperature for 40 minutes. The reaction solution was distilled off under reduced pressure. The residue was subjected to silica gel column chromatography (hexane/ethyl acetate=3/1) to afford 1.04 g of the title compound (yield 99%).

$^1$H NMR (400 MHz, CDCl$_3$) δ 1.41 (s, 9H), 1.50-1.72 (m, 2H), 1.75-1.98 (m, 2H), 2.94 (br.d., J=14.0 Hz, 1H), 3.16 (br.s., 1H), 4.09-4.26 (m, 1H), 4.16-4.55 (m, 3H), 4.65-4.78 (m, 3H), 5.41 (br.s., 1H), 7.20-7.41 (m, 10H); MS m/z 440 [M+H]$^+$.

Step 2 tert-Butyl (2S,5R)-2-(benzylcarbamoyl)-5-((benzyloxy)((trichloromethoxy) carbonyl)amino)piperidine-1-carboxylate or tert-butyl (2S,5R)-2-(benzylcarbamoyl)-5-((benzyloxy)(chlorocarbonyl)amino) piperidine-1-carboxylate tert-Butyl (2S,5R)-2-(benzylcarbamoyl)-5-((benzyloxy) amino)piperidine-1-carboxylate (559 mg, 1.27 mmol) was dissolved in dehydrated dichloromethane (8 mL), and diisopropylethylamine (329 mg) was added, followed by ice cooling. To the above mixture was added triphosgene (226 mg) under ice cooling, followed by stirring for 0.5 hours, and the completion of the reaction for the title compounds was confirmed by TLC. The compounds were subjected to the next step without purification and isolation.

Step 3

Trichloromethyl (((3R,6S)-6-(benzylcarbamoyl)piperidin-3-yl)(benzyloxy) carbamate or ((3R,6S)-6-(benzylcarbamoyl)piperidin-3-yl)(benzyloxy)carbamoyl chloride Then, methanesulfonic acid (0.83 mL) was added, followed by stirring for 5 minutes, and the completion of the reaction for the title compounds was confirmed by TLC. The compounds were subjected to the next step without purification and isolation.

Step 4

(2S,5R)—N-Benzyl-6-(benzyloxy)-7-oxo-1,6-diazabicyclo[3.2.1]octane-2-carboxamide The mixture in Step 2 above was added dropwise to an ice-cold 1 M potassium bicarbonate (1.4 g/11.5 mL), followed by stirring for 0.5 hours. Ethyl acetate (65 mL) was added and layers were separated. The organic layer was washed with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with hexane/ethyl acetate=1/1 to afford 331 mg of the title compound (yield 71%).

$^1$H NMR (400 MHz, CDCl$_3$) δ 1.54-1.67 (m, 1H), 1.88-2.08 (m, 2H), 2.36-2.48 (m, 1H), 2.67 (d, J=11.4 Hz, 1H), 2.97 (br.d., J=11.4 Hz, 1H), 3.28 (m, 1H), 3.96 (d, J=7.3 Hz), 1H), 4.38-4.55 (m, 2H), 4.90 (d, J=11.4 Hz, 1H), 5.05 (d, J=11.4 Hz, 1H), 6.95 (br.s., 1H), 7.20-7.47 (m, 10H); MS m/z 366 [M+H]$^+$.

Reference Example 18

2,5-Dioxopyrrolidin-1-yl (2S,5R)-6-(benzyloxy)-7-oxo-1,6-diazabicyclo[3.2.1] octane-2-carboxylate (III-57)

[Chemical Formula 36]

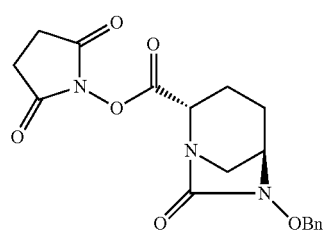

III-57

(2S,5R)-6-(Benzyloxy)-7-oxo-1,6-diazabicyclo[3.2.1]octane-2-carboxylic acid (201 mg, 0.758 mmol) was dissolved in dehydrated dichloromethane (3.6 mL), and N-methylmorpholine (162 mg) was added, followed by cooling to 0° C. To the mixture was added isobutyl chloroformate (198.8 mg), followed by stirring for 10 minutes. Subsequently, 1-hydroxypyrrolidine-2,5-dione (167 mg) was added, followed by stirring for another 0.5 hours. The reaction mixture was washed with water and dried over anhydrous magnesium sulfate, and the filtrate was concentrated under reduced pressure. The resulting residue was subjected to silica gel column chromatography (hexane/ethyl acetate=1/2) to afford 161 mg of the title compound as a colorless solid (yield 57%).

$^1$H NMR (400 MHz, CDCl$_3$) δ 1.70-1.77 (m, 1H), 2.04-2.27 (m, 3H), 2.80-2.90 (m, 4H), 3.09-3.19 (m, 2H), 3.35 (br.s., 1H), 4.48 (d, J=6.9 Hz, 1H), 4.92 (d, J=11.3 Hz, 1H), 5.07 (d, J=11.3 Hz, 1H), 7.35-7.45 (m, 5H); MS m/z 374 [M+H]$^+$.

Reference Example 19

(1R,2S,6R,7S)-3,5-Dioxo-4-azatricyclo[5.2.1.0$^{2,6}$] dec-8-en-4-yl (2S,5R)-6-(benzyloxy)-7-oxo-1,6-diazabicyclo[3.2.1]octane-2-carboxylate (III-58)

[Chemical Formula 37]

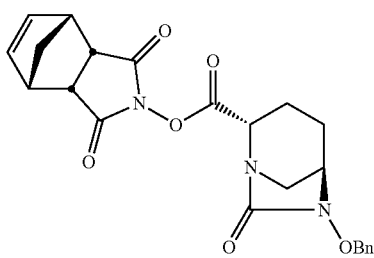

III-58

(2S,5R)-6-(Benzyloxy)-7-oxo-1,6-diazabicyclo[3.2.1]octane-2-carboxylic acid (529 mg, 1.918 mmol) was dissolved in dehydrated tetrahydrofuran (5.5 mL), followed by cooling to −20° C. To the mixture was added N-methylmorpholine (445 mg) and isobutyl chloroformate (300 mg), followed by stirring for 15 minutes. Subsequently, (1R,2S,6R,7S)-4-hydroxy-4-azatricyclo[5.2.1.0$^{2,6}$]dec-8-ene-3,5-dione (394 mg) was added, followed by stirring for 0.5 hours and then at room temperature for another 0.5 hours. The reaction mixture was diluted with chloroform (50 mL), washed sequentially with 1 M hydrochloric acid (20 mL), saturated sodium bicarbonate (20 mL) and saturated brine (20 mL) and dried over anhydrous magnesium sulfate, and the filtrate was concentrated under reduced pressure. The resulting residue was dissolved in chloroform (4 mL), and hexane (4 mL) was added, followed by stirring for 5 minutes. Further, hexane (4 mL) was added, followed by stirring and aging for 1.5 hours. The precipitated solid was filtered, washed with a mixed solution of chloroform/hexane (2/3) and dried under reduced pressure to afford 678 mg of the title compound as a colorless crystalline-powder (yield 81%).

HPLC: COSMOSIL 5C18 MS-II 4.6×150 mm, 35° C., 0.02M TFA/CH3CN=50/50, 1.0 ml/min, UV 210 nm, RT 7.1 min; enantiomeric excess 99.9% ee or more: CHIRALPAK AD-H, 4.6×150 mm, 40° C., Hexane/EtOH=1/1, UV 210 nm, 1 mL/min, RT 37.3 min (cf. enantiomer 16.5 min); Mp 196° C.; $[\alpha]^{26}_D$ +12.686° (c 0.885, CHCl$_3$); $^1$H NMR (400 MHz, CDCl$_3$) δ 1.52 (d, J=9.1 Hz, 1H), 1.70 (m, 1H), 1.78 (d, J=9.1 Hz, 1H), 2.01-2.26 (m, 3H), 3.04-3.17 (m, 2H), 3.32 (m, 3H), 3.45 (br.s., 2H), 4.41 (d, J=6.7 Hz, 1H), 4.91 (d, J=11.4 Hz, 1H), 5.06 (d, J=11.4 Hz, 1H), 6.19 (br.s., 2H), 7.33-7.46 (m, 5H); MS m/z 438 [M+H]$^+$.

Reference Example 20

(3aR,7aS)-2-Hydroxy-3a,4,7,7a-tetrahydro-1H-isoindol-1,3(2H)-dione

[Chemical Formula 38]

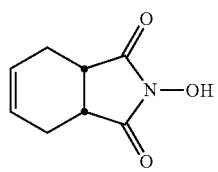

Hydroxylamine sulfate (24.975 g, 0.152 mol) was dissolved in water (100 mL), and (3aR,7aS)-3a,4,7,7a-tetrahydroisobenzofuran-1,3-dione (45.228 g) was added. To the mixture was added 25% sodium hydroxide aqueous solution (50 g) over 15 minutes in small portions, followed by stirring at 90° C. for 2 hours. The mixture was cooled to room temperature, and the precipitated crystalline-solid was suction-filtered, followed by deliquoring for 30 minutes. The wet crystals were dried in vacuo at 50° C. for 2 days to afford 42.87 g of the title compound (yield 87%).
$^1$H NMR (400 MHz, CDCl$_3$) δ 2.20-2.31 (m, 2H), 2.56-2.65 (m, 2H), 3.08-3.14 (m, 2H), 5.91 (dt, J=0.9, 2.7 Hz, 2H); MS m/z 166 [M-H]$^-$.

Reference Example 21

(3aR,7aS)-1,3-Dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate (III-59)

[Chemical Formula 39]

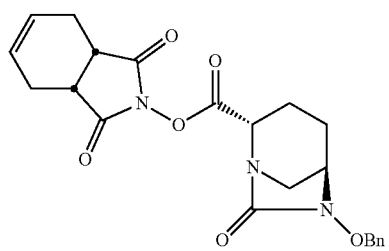

III-59

(2S,5R)-6-(Benzyloxy)-7-oxo-1,6-diazabicyclo[3.2.1]octane-2-carboxylic acid (1.831 g, 5 mmol) was dissolved in dehydrated tetrahydrofuran (15 mL), followed by cooling to −20° C. To the mixture were added isobutyl chloroformate (751 mg) and triethylamine (1.111 g), followed by stirring for 15 minutes. Subsequently, (3aR,7aS)-2-hydroxy-3a,4,7,7a-tetrahydro-1H-isoindol-1,3(2H)-dione (Reference Example 20, 919 mg) was added, followed by stirring for 0.5 hours and then at room temperature for another 0.5 hours. The reaction mixture was diluted with chloroform (150 mL), washed sequentially with 1 M hydrochloric acid (60 mL), saturated sodium bicarbonate (60 mL) and saturated brine (60 mL) and dried over anhydrous magnesium sulfate, and the filtrate was concentrated under reduced pressure. The resulting residue was dissolved in chloroform (4 mL), and hexane (4 mL) was added, followed by stirring for 30 minutes. Further, hexane (2 mL) was added, followed by stirring and aging for 30 minutes. The precipitated solid was filtered, washed with a mixed solution of chloroform/hexane (2/3) and dried under reduced pressure to afford 1.419 g of the title compound as a colorless crystalline-powder (yield 67%).
$^1$H NMR (400 MHz, CDCl$_3$) δ 1.67-1.77 (m, 1H), 2.08 (d, J=14.2 Hz, 1H), 2.14-2.26 (m, 2H), 2.30 (d, J=13.8 Hz, 2H), 2.55-2.66 (m, 2H), 3.10-3.24 (m, 4H), 3.34 (bs, 1H), 4.45 (d, J=6.4 Hz, 1H), 4.91 (d, J=11.2 Hz, 1H), 5.06 (d, J=11.4 Hz, 1H), 5.97 (bs, 2H), 7.34-7.45 (m, 5H); MS m/z 426 [M+H]$^+$.

Reference Example 22

(3aR,7aS)-2-Hydroxyhexahydro-1H-isoindol-1,3(2H)-dione

[Chemical Formula 40]

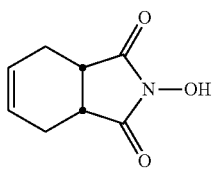

Hydroxylamine sulfate (24.975 g, 0.152 mol) was dissolved in water (75 mL) and (3aR,7aS)-hexahydroisobenzofuran-1,3-dione (48.000 g) was added. To the mixture was added 25% sodium hydroxide aqueous solution (50 g) over 15 minutes in small portions, followed by stirring at 90° C. for 1 hour. The mixture was cooled to room temperature, extracted twice with chloroform 50 mL, dried over anhydrous sodium sulfate, and filtered. The filtrate was concentrated under reduced pressure, the residue was dissolved in chloroform, insoluble was filtered, and the solvent was concentrated under reduced pressure. The residue was dissolved by adding ethyl acetate, the solvent was concentrated under reduced pressure and dried in vacuo for further 2 days to afford 49.35 g of the title compound as a colorless solid (yield 94%).
$^1$H NMR (400 MHz, CDCl$_3$) δ 1.45 (dt, J=3.0, 5.9 Hz, 4H), 1.71-1.90 (m, 4H), 2.84-2.92 (m, 2H), 6.01 (b rs, 1H); MS m/z 168 [M-H]$^-$.

Reference Example 23

(3aR,7aS)-1,3-Dioxohexahydro-1H-isoindol-2(3H)-yl (2S,5R)-6-(benzyloxy)-7-oxo-1,6-diazabicyclo[3.2.1]octane-2-carboxylate (III-60)

[Chemical Formula 41]

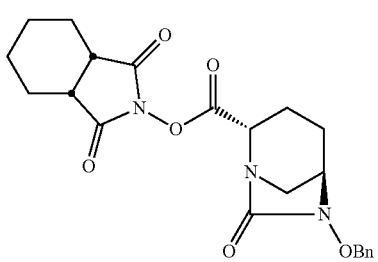

III-60

(2S,5R)-6-(Benzyloxy)-7-oxo-1,6-diazabicyclo[3.2.1]octane-2-carboxylic acid (1.831 g, 5 mmol) was dissolved in dehydrated tetrahydrofuran (15 mL), followed by cooling to -20° C. To the mixture were added isobutyl chloroformate (751 mg) and triethylamine (1.111 g), followed by stirring for 15 minutes. Subsequently, (3aR,7aS)-2-hydroxyhexahydro-1H-isoindol-1,3(2H)-dione (Reference Example 22, 919 mg) was added, followed by stirring for 0.5 hours and then at room temperature for another 0.5 hours. The reaction mixture was diluted with chloroform (150 mL), washed sequentially with 1M hydrochloric acid (60 mL), saturated sodium bicarbonate (60 mL), and saturated brine (60 mL), and dried over anhydrous magnesium sulfate, and the filtrate was concentrated under reduced pressure. The resulting residue was subjected to silica gel column chromatography (chloroform/ethyl acetate=6/1) to afford 1.294 g of the title compound as a colorless solid (yield 61%).

$^1$H NMR (400 MHz, CDCl$_3$) δ 1.50 (bs, 4H), 1.62 (bs, 1H), 1.68-1.84 (m, 1H), 1.91 (bs, 4H), 2.04-2.27 (m, 2H), 3.02 (bs, 2H), 3.15 (s, 2H), 3.35 (bs, 1H), 4.47 (d, J=6.6 Hz, 1H), 4.92 (d, J=11.2 Hz, 1H), 5.07 (d, J=11.4 Hz, 1H), 7.34-7.45 (m, 5H); MS m/z 428 [M+H]$^+$.

Example 1

1-tert-Butyl 2-methyl (2S,5R)-5-((benzyloxy)amino)piperidine-1,2-dicarboxylate

[Chemical Formula 42]

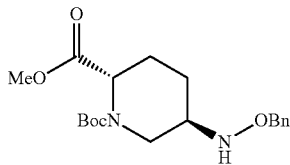

II-1

A mixture of methyl (2S,5R)-5-(benzyloxyamino)piperidine-2-carboxylate dihydrochloride (Reference Example 1, 6.64 g, 19.7 mmol) and methanol (66.4 mL) was ice cooled and triethylamine (5.57 mL) was added and dissolved. To the mixture was added di-tert-butyl dicarbonate (4.80 g), followed by stirring at room temperature for 2.5 hours. The residue resulted from concentration of the reaction solution under reduced pressure was diluted with ethyl acetate, washed sequentially with saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 7.68 g of the title compound (quantitative).

$^1$H NMR (400 MHz, CDCl$_3$) δ 1.46 (s, 9H), 1.48-1.73 (m, 2H), 1.89-2.01 (m, 2H), 3.00-3.24 (m, 2H), 3.73 (s, 3H), 4.14-4.23 (m, 1H), 4.65-4.79 (m, 2H), 4.90 (br.s., 0.5H), 5.46 (br.s., 1H), 7.27-7.38 (m, 5H); MS m/z 365 [M+H]$^+$.

Example 2

1-tert-Butyl 2-ethyl(2S,5R)-5-((benzyloxy)amino)piperidine-1,2-dicarboxylate

[Chemical Formula 43]

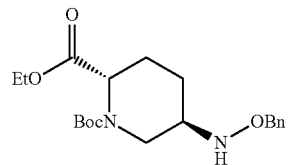

II-2

(2S,5R)-5-((Benzyloxy)amino)-1-(tert-butoxycarbonyl)piperidine-2-carboxylic acid (Reference Example 4, 383 mg, 1.09 mmol) was dissolved in dehydrated acetonitrile (7.0 mL), and ethyl iodide (1.7 g) and diisopropylethylamine (212 mg) were added, followed by stirring at room temperature overnight. The reaction solution was diluted with ethyl acetate, washed sequentially with 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=3/1) to afford 339 mg of the title compound (yield 82%).

$^1$H NMR (400 MHz, CDCl$_3$) δ 1.27 (m, 3H), 1.46 (m, 9H), 1.49-1.75 (m, 2H), 1.84-2.03 (m, 2H), 2.97-3.30 (m, 3H), 4.11-4.27 (m, 2H), 4.61-4.82 (m, 2H), 4.86 (br.s., 0.5H), 5.47 (br.s., 1H), 7.24-7.40 (m, 5H); MS m/z 379 [M+H]$^+$.

Example 3

2-Allyl 1-tert-butyl(2S,5R)-5-((benzyloxy)amino)piperidine-1,2-dicarboxylate

[Chemical Formula 44]

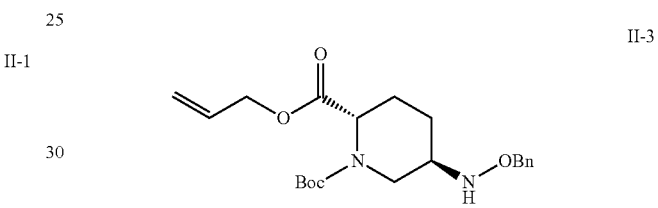

II-3

(2S,5R)-5-((Benzyloxy)amino)-1-(tert-butoxycarbonyl)piperidine-2-carboxylic acid (Reference Example 4, 1.2 g, 3.42 mmol) was dissolved in dehydrated acetonitrile (18 mL), and allyl bromide (496.5 mg) was added, followed by ice cooling. To the mixture was added diisopropylethylamine (0.586 g), followed by stirring at room temperature overnight. The reaction solution was diluted with ethyl acetate (100 mL), washed sequentially with 8% citric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 1.14 g of the title compound (yield 85%).

1H NMR (400 MHz, CDCl$_3$) δ 1.47 (s, 9H), 1.55-1.76 (m, 2H), 1.90-2.03 (m, 2H), 3.04-3.28 (m, 2H), 4.14 (m, 1H), 4.61-4.69 (br.s., 2H), 4.74 (m, 2H), 5.26 (d, J=10.5 Hz, 1H), 5.35 (dd, J=17.2, 1.4 Hz, 1H), 5.49 (br.s., 1H), 5.92 (m, 1H), 7.29-7.41 (m, 5H); MS m/z 391 [M+H]$^+$.

Example 4

2-Benzyl 1-tert-butyl (2S,5R)-5-((benzyloxy)amino)piperidine-1,2-dicarboxylate

[Chemical Formula 45]

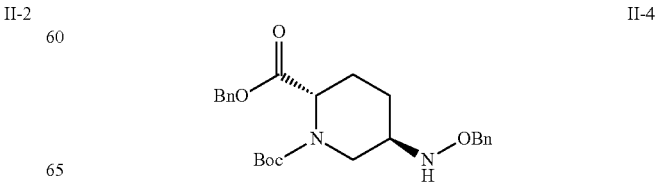

II-4

(2S,5R)-5-((Benzyloxy)amino)-1-(tert-butoxycarbonyl) piperidine-2-carboxylic acid (Reference Example 4, 578 mg, 1.65 mmol) was dissolved in dehydrated acetonitrile (8 mL), and benzyl bromide (423 mg) and diisopropylethylamine (256 mg) were added, followed by stirring at room temperature overnight. The reaction solution was diluted with ethyl acetate, washed sequentially with 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=8/1) to afford 572 mg of the title compound (yield 79%).

1H NMR (400 MHz, CDCl$_3$) δ 1.37-1.55 (m, 10H), 1.64-1.73 (m, 1H), 1.91-2.03 (m, 2H), 3.04-3.26 (m, 2H), 4.17-4.25 (br.s., 1H), 4.68-4.80 (m, 2H), 4.97 (br.s., 1H), 5.14-5.26 (m, 2H), 5.48 (br.s., 1H), 7.28-7.40 (m, 10H); MS m/z 441 [M+H]$^+$.

Example 5

1-tert-Butyl 2-cyanomethyl (2S,5R)-5-((benzyloxy)amino)piperidine-1,2-dicarboxylate

[Chemical Formula 46]

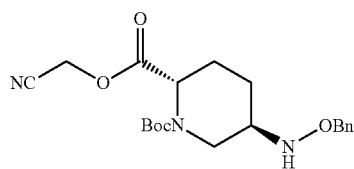

II-5

(2S,5R)-5-((Benzyloxy)amino)-1-(tert-butoxycarbonyl) piperidine-2-carboxylic acid (Reference Example 4, 350 mg, 1 mmol) was dissolved in dehydrated acetonitrile (7.0 mL), and chloroacetonitrile (755 mg) and diisopropylethylamine (193 mg) were added, followed by stirring at room temperature overnight. The reaction solution was diluted with ethyl acetate, washed sequentially with 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=1/1) to afford 384 mg of the title compound (yield 99%).

$^1$H NMR (400 MHz, CDCl$_3$) δ 1.46 (s, 9H), 1.50-1.75 (m, 2H), 1.87-2.06 (m, 2H), 3.08-3.28 (m, 2H), 4.15 (m, 1H), 4.63-4.85 (m, 4H), 4.95 (br.s., 0.5H), 5.43 (br.s., 1H), 7.26-7.38 (m, 5H); MS m/z 390 [M+H]$^+$.

Example 6

1-tert-Butyl 2-(4-chlorophenyl) (2S,5R)-5-((benzyloxy)amino)piperidine-1,2-dicarboxylate

[Chemical Formula 47]

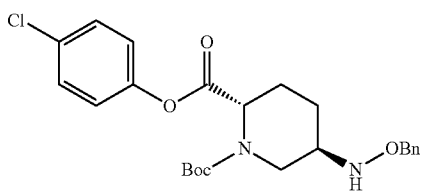

II-6

(2S,5R)-5-((Benzyloxy)amino)-1-(tert-butoxycarbonyl) piperidine-2-carboxylic acid (Reference Example 4, 700 mg, 2.0 mmol) was dissolved in dehydrated dichloromethane (7 mL), and 4-chlorophenol (308 mg) was added, followed by ice cooling. To the mixture were sequentially added 1-ethyl-3-(3-dimethylaminopropyl) carbodiimide hydrochloride (459 mg) and 4-dimethylaminopyridine (122 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=4/1) to afford 727 mg of the title compound (yield 79%).

$^1$H NMR (400 MHz, CDCl$_3$) δ 1.47 (s, 9H), 1.53-1.82 (m, 3H), 2.09 (m, 1H), 3.12-3.32 (m, 2H), 4.20 (m, 1H), 4.68-4.81 (m, 2H), 5.09 (br.s., 0.5H), 5.49 (br.s., 1H), 7.03 (d, J=7.8 Hz, 2H), 7.28-7.41 (m, 7H); MS m/z 461 [M+H]$^+$.

Example 7

1-tert-Butyl 2-(2,4,6-trichlorophenyl) (2S,5R)-5-((benzyloxy)amino)piperidine-1,2-dicarboxylate

[Chemical Formula 48]

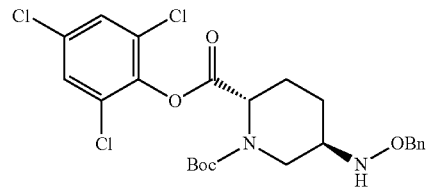

II-7

(2S,5R)-5-((Benzyloxy)amino)-1-(tert-butoxycarbonyl) piperidine-2-carboxylic acid (Reference Example 4, 700 mg, 2.0 mmol) was dissolved in dehydrated dichloromethane (7 mL) and 2,4,6-trichlorophenol (473 mg) was added, followed by ice cooling. To the mixture were sequentially added 1-ethyl-3-(3-dimethylaminopropyl) carbodiimide hydrochloride (459 mg) and 4-dimethylamino pyridine (122 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=4/1) to afford 926 mg of the title compound (yield 88%).

$^1$H NMR (400 MHz, CDCl$_3$) δ 1.47 (br.s., 9H), 1.65-1.91 (m, 2H), 2.08-2.28 (m, 2H), 3.13-3.37 (m, 2H), 4.17-4.41 (m, 1H), 4.65-4.82 (m, 2H), 5.14 (br.s., 1H), 5.31 (br.s., 0.5H), 5.50 (br.s., 0.5H), 7.22-7.45 (m, 7H); MS m/z 529 [M+H]$^+$.

Example 8

1-tert-Butyl 2-(2,3,4,5,6-pentafluorophenyl) (2S,5R)-5-((benzyloxy)amino) piperidine-1,2-dicarboxylate

[Chemical Formula 49]

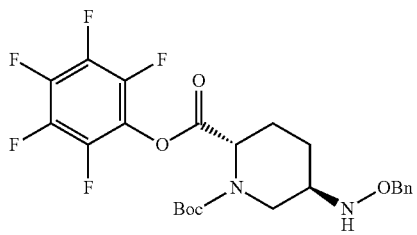

II-8

(2S,5R)-5-((Benzyloxy)amino)-1-(tert-butoxycarbonyl)piperidine-2-carboxylic acid (Reference Example 4, 435 mg, 1.24 mmol) was dissolved in dehydrated dichloromethane (8 mL) and 2,3,4,5,6-pentafluorophenol (274 mg) was added, followed by ice cooling. To the mixture were sequentially added 1-ethyl-3-(3-dimethylaminopropyl)carbodiimide hydrochloride (285 mg) and 4-dimethylaminopyridine (76 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=8/1) to afford 461 mg of the title compound (yield 71%).

$^1$H NMR (400 MHz, CDCl$_3$) δ 1.47 (br.s., 9H), 1.57-1.72 (m, 1H), 1.77-1.88 (m, 1H), 2.01-2.26 (m, 2H), 3.06-3.39 (m, 2H), 4.17-4.34 (m, 1H), 4.66-4.82 (m, 2H), 5.06 (br.s., 1H), 5.27 (br.s., 0.5H), 7.25-7.39 (m, 5H); MS m/z 517 [M+H]$^+$.

Example 9

1-tert-Butyl 2-(4-nitrophenyl) (2S,5R)-5-((benzyloxy)amino)piperidine-1,2-dicarboxylate

[Chemical Formula 50]

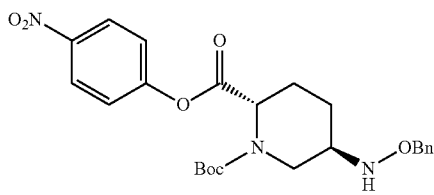

II-9

(2S,5R)-5-((Benzyloxy)amino)-1-(tert-butoxycarbonyl)piperidine-2-carboxylic acid (Reference Example 4, 1.40 g, 4.0 mmol) was dissolved in dehydrated dichloromethane (15 mL) and 4-nitrophenol (667 mg) was added, followed by ice cooling. To the mixture were sequentially added 1-ethyl-3-(3-dimethylaminopropyl) carbodiimide hydrochloride (920 mg) and 4-dimethylaminopyridine (244 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 1.52 g of the title compound (yield 80%).

$^1$H NMR (400 MHz, CDCl$_3$) δ 1.49 (s, 9H), 1.58-1.82 (m, 2H), 2.04-2.21 (m, 2H), 3.20-3.35 (m, 2H), 4.18 (m, 1H), 4.67-4.82 (m, 2H), 5.07 (br.s., 1H), 6.90 (d, J=7.9 Hz, 2H), 7.29-7.39 (m, 5H), 8.15 (d, J=7.9 Hz, 2H); MS m/z 416 [M+H]$^+$.

Example 10

1-tert-Butyl 2-(4-cyanophenyl) (2S,5R)-5-((benzyloxy)amino)piperidine-1,2-dicarboxylate

[Chemical Formula 51]

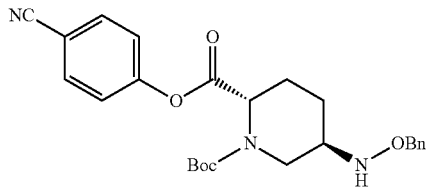

II-10

(2S,5R)-5-((benzyloxy)amino)-1-(tert-butoxycarbonyl)piperidine-2-carboxylic acid (Reference Example 4, 565 mg, 1.61 mmol) was dissolved in dehydrated dichloromethane (6 mL), and 4-cyanophenol (230 mg) was added, followed by ice cooling. To the mixture were sequentially added 1-ethyl-3-(3-dimethylaminopropyl) carbodiimide hydrochloride (370 mg) and 4-dimethylaminopyridine (98 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=3/1) to afford 464 mg of the title compound (yield 64%).

$^1$H NMR (400 MHz, CDCl$_3$) δ 1.47 (br s, 9H), 1.58-1.86 (m, 2H), 2.00-2.22 (m, 2H), 3.11-3.35 (m, 2H), 3.92 (s, 3H), 4.12-4.33 (m, 1H), 4.67-4.83 (m, 2H), 5.11 (br.s., 1H), 7.16 (d, J=8.1 Hz, 2H), 7.26-7.41 (m, 5H), 8.07 (br.d., J=8.1 Hz, 2H); MS m/z 452 [M+H]$^+$.

Example 11

1-tert-Butyl 2-(4-carbamoylphenyl) (2S,5R)-5-((benzyloxy)amino)piperidine-1,2-dicarboxylate

[Chemical Formula 52]

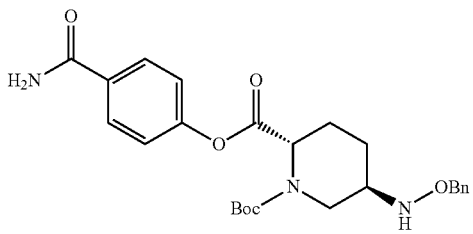

II-11

(2S,5R)-5-((Benzyloxy)amino)-1-(tert-butoxycarbonyl) piperidine-2-carboxylic acid (Reference Example 4, 1.54 g, 4.40 mmol) was dissolved in dehydrated dichloromethane (20 mL), followed by ice cooling. 4-Hydroxybenzamide (742 mg), 1-ethyl-3-(3-dimethylaminopropyl)carbodiimide hydrochloride (1.01 g) and 4-dimethylaminopyridine (273 mg) were added sequentially, followed by stirring at room temperature for 45 minutes. The reaction solution was diluted with ethyl acetate and washed sequentially with ice-cold 10% citric acid, saturated sodium bicarbonate and saturated brine. The organic layer was dried over anhydrous sodium sulfate and filtered, and subsequently the solvent was distilled off under reduced pressure. The residue was subjected to silica gel column chromatography (hexane/ethyl acetate=4/1 to 0/10) to afford 1.45 g of the title compound (yield 70%).

$^1$H NMR (400 MHz, CDCl$_3$) δ 1.48 (s, 9H), 1.60-1.83 (m, 2H), 2.05-2.20 (m, 2H), 3.10-3.35 (m, 1H), 4.10-4.35 (m, 1H), 4.72 (d, J=11.6 Hz, 1H), 4.77 (d, J=11.6 Hz, 1H), 4.93 (br.s., 0.5H), 5.10 (br.s., 0.5H), 5.50 (br.s., 1H), 5.55-6.25 (m, 2H), 7.18 (m, 2H), 7.29-7.39 (m, 5H), 7.85 (m, 2H); MS m/z 470 [M+H]$^+$.

Example 12

1-tert-Butyl 2-(4-methoxycarbonylphenyl) (2S,5R)-5-((benzyloxy)amino) piperidine-1,2-dicarboxylate

[Chemical Formula 53]

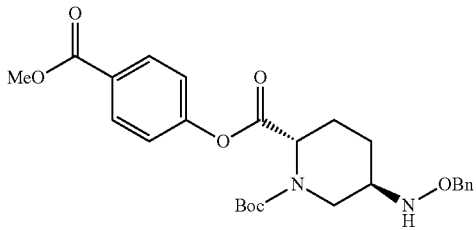

II-12

(2S,5R)-5-((Benzyloxy)amino)-1-(tert-butoxycarbonyl) piperidine-2-carboxylic acid (Reference Example 4, 720 mg, 2.05 mmol) was dissolved in dehydrated dichloromethane (8 mL), and 4-methoxycarbonylphenol (375 mg) was added, followed by ice cooling. To the mixture were sequentially added 1-ethyl-3-(3-dimethylaminopropyl)carbodiimide hydrochloride (473 mg) and 4-dimethylaminopyridine (125 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=3/1) to afford 834 mg of the title compound (yield 84%).

$^1$H NMR (400 MHz, CDCl$_3$) δ 1.47 (br.s., 9H), 1.58-1.86 (m, 2H), 2.00-2.22 (m, 2H), 3.11-3.35 (m, 2H), 3.92 (s, 3H), 4.12-4.33 (m, 1H), 4.67-4.83 (m, 2H), 5.11 (br.s., 1H), 7.16 (d, J=8.1 Hz, 2H), 7.26-7.41 (m, 5H), 8.07 (br.d., J=8.1 Hz, 2H); MS m/z 485 [M+H]$^+$.

Example 13

1-tert-Butyl 2-(4-methylsulfonylphenyl) (2S,5R)-5-((benzyloxy)amino) piperidine-1,2-dicarboxylate

[Chemical Formula 54]

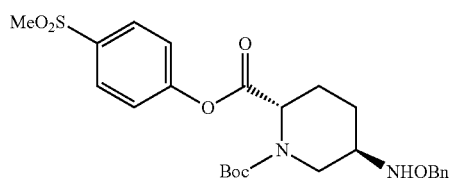

II-13

(2S,5R)-5-((Benzyloxy)amino)-1-(tert-butoxycarbonyl) piperidine-2-carboxylic acid (Reference Example 4, 898 mg, 2.56 mmol) was dissolved in dehydrated dichloromethane (16 mL), and 4-methylsulfonylphenol (530 mg) was added, followed by ice cooling. To the mixture were sequentially added 1-ethyl-3-(3-dimethylaminopropyl)carbodiimide hydrochloride (590 mg) and 4-dimethylaminopyridine (157 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 839 mg of the title compound (yield 65%).

$^1$H NMR (400 MHz, CDCl$_3$) δ 1.48 (br.s., 9H), 1.60-1.84 (m, 2H), 2.02-2.24 (m, 2H), 3.06 (s, 3H), 3.18-3.38 (m, 2H), 4.07-4.24 (m, 1H), 4.66-4.84 (m, 2H), 5.08 (br.s., 1H), 7.25-7.42 (m, 7H), 7.99 (m, 2H); MS m/z 505 [M+H]$^+$.

Example 14

1-tert-Butyl 2-(4-sulfamoylphenyl) (2S,5R)-5-((benzyloxy)amino)piperidine-1,2-dicarboxylate

[Chemical Formula 55]

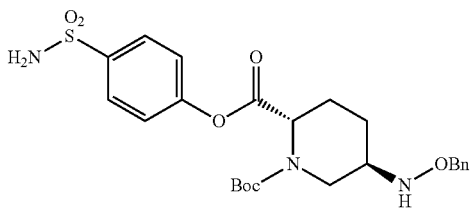

II-14

(2S,5R)-5-((Benzyloxy)amino)-1-(tert-butoxycarbonyl) piperidine-2-carboxylic acid (Reference Example 4, 746 mg, 2.13 mmol) was dissolved in dehydrated dichloromethane (8 mL), and 4-hydroxybenzenesulfonamide (442 mg) was added, followed by ice cooling. To the mixture were sequentially added 1-ethyl-3-(3-dimethylaminopropyl)carbodiimide hydrochloride (490 mg) and 4-dimethylaminopyridine (130 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 375 mg of the title compound (yield 35%).

$^1$H NMR (400 MHz, CDCl$_3$) δ 1.47 (s, 9H), 1.54-1.84 (m, 2H), 1.97-2.22 (m, 2H), 3.08-3.36 (m, 2H), 4.11-4.23 (m, 1H), 4.66-4.81 (m, 2H), 4.94 (m, 1H), 5.47 (br.s., 1H), 7.19-7.45 (m, 7H), 7.95 (br.d., J=8.1 Hz, 2H); MS m/z 506 [M+H]$^+$.

Example 15

1-tert-Butyl 2-(quinolin-8-yl) (2S,5R)-5-((benzyloxy)amino)piperidine-1,2-dicarboxylate

[Chemical Formula 56]

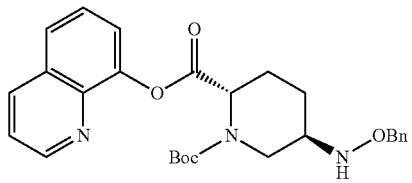

II-15

(2S,5R)-5-((benzyloxyBenzyloxy)amino)-1-(tert-butoxycarbonyl)piperidine-2-carboxylic acid (Reference Example 4, 700 mg, 2.0 mmol) was dissolved in dehydrated dichloromethane (7 mL), and 8-quinolinol (348 mg) was added, followed by ice cooling. To the mixture were sequentially added 1-ethyl-3-(3-dimethylaminopropyl)carbodiimide hydrochloride (459 mg) and 4-dimethylaminopyridine (122 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=3/1) to afford 655 mg of the title compound (yield 69%).

$^1$H NMR (400 MHz, CDCl$_3$) δ 1.36-1.57 (m, 9H), 1.79-1.93 (m, 1H), 2.04-2.48 (m, 3H), 3.25-3.66 (m, 2H), 4.17-4.35 (m, 1H), 4.71-4.85 (m, 2H), 5.20 (br.s., 0.5H), 5.35 (br.s., 0.5H), 5.58 (br.s., 1H), 7.26-7.57 (m, 8H), 7.72 (br.d., J=8.2 Hz, 1H), 8.16 (d, J=8.2 Hz, 1H), 8.34 (m, 1H); MS m/z 478 [M+H]$^+$.

Example 16

1-tert-Butyl 2-(5-chloroquinolin-8-yl) (2S,5R)-5-((benzyloxy)amino) piperidine-1,2-dicarboxylate

[Chemical Formula 57]

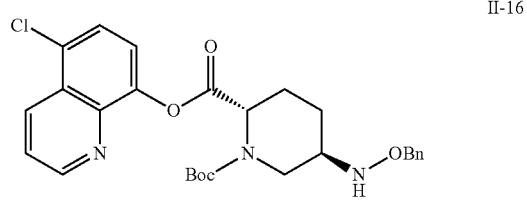

II-16

(2S,5R)-5-((Benzyloxy)amino)-1-(tert-butoxycarbonyl)piperidine-2-carboxylic acid (Reference Example 4, 824 mg, 2.35 mmol) was dissolved in dehydrated dichloromethane (7 mL), and 5-chloroquinolin-8-ol (507 mg) was added, followed by ice cooling. To the mixture were sequentially added 1-ethyl-3-(3-dimethylaminopropyl)carbodiimide hydrochloride (541 mg) and 4-dimethylaminopyridine (144 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, drired over anhydrous magnesium sulfate and filtered, and the solvent was distilled off under reduced pressure. The residue was subjected to silica gel column chromatography (hexane/ethyl acetate=4/1) to afford 841 mg of the title compound (yield 70%).

$^1$H NMR (400 MHz, CDCl$_3$) δ 1.39-1.61 (m, 9H), 1.80-1.92 (m, 1H), 2.01-2.43 (m, 3H), 3.24-3.64 (m, 2H), 4.16-4.35 (m, 1H), 4.69-4.84 (m, 2H), 5.18 (br.s., 0.5H), 5.34 (br.s., 0.5H), 5.57 (br.s., 1H), 7.24-7.45 (m, 6H), 7.52 (br.s., 1H), 7.60 (d, J=7.9 Hz, 1H), 8.54 (br.d., J=7.6 Hz, 1H), 8.87 (br.d., J=3.7 Hz, 1H); MS m/z 512 [M+H]$^+$.

Example 17

1-tert-Butyl 2-(pyridine-2-yl) (2S,5R)-5-((benzyloxy)amino)piperidine-1,2-dicarboxylate

[Chemical Formula 58]

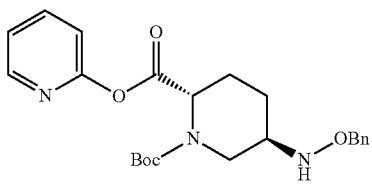

II-17

(2S,5R)-5-((benzyloxy)amino)-1-(tert-butoxycarbonyl)piperidine-2-carboxylic acid (Reference Example 4, 813 mg, 2.32 mmol) was dissolved in dehydrated dichloromethane (16 mL), followed by ice cooling. 1-Ethyl-3-(3-dimethylaminopropyl)carbodiimide hydrochloride (494 mg), 2-hydroxypyridine (239 mg) and 4-dimethylaminopyridine (142 mg) were added sequentially, followed by stirring at room temperature for 1 hour. The reaction solution was diluted with ethyl acetate and washed with ice-cold 10% citric acid, saturated sodium bicarbonate and saturated brine. The organic layer were dried over anhydrous sodium sulfate and filtered, and subsequently the solvent was distilled off under reduced pressure. The residue was subjected to silica gel column chromatography (hexane/ethyl acetate=4/1 to 1/1) to afford 586 mg of the title compound (yield 59%).

$^1$H NMR (400 MHz, CDCl$_3$) δ 1.48 (s, 9H), 1.70-1.85 (m, 2H), 2.08-2.21 (m, 2H), 3.16-3.38 (m, 2H), 4.09-4.34 (m, 1H), 4.72 (d, J=11.6 Hz, 1H), 4.77 (d, J=11.6 Hz, 1H), 4.98 (br.s., 0.5H), 5.16 (br.s., 0.5H), 5.50 (br.s., 1H), 7.20-7.40 (m, 7H), 7.80 (m, 1H), 8.41 (m, 1H); MS m/z 428 [M+H]$^+$.

Example 18 tert-Butyl (2S,5R)-5-((benzyloxy)amino)-2-(((diethylamino)oxy)carbonyl) piperidine-1-carboxylate

[Chemical Formula 59]

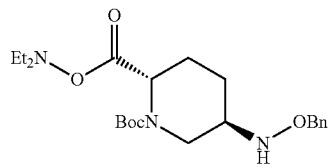

II-18

(2S,5R)-5-((Benzyloxy)amino)-1-(tert-butoxycarbonyl)piperidine-2-carboxylic acid (Reference Example 4, 848 mg, 2.42 mmol) was dissolved in dehydrated dichloromethane (8 mL), and an 85% N-hydroxydiethylamine aqueous solution (0.84 mL) was added, followed by ice cooling. To the mixture were sequentially added 1-ethyl-3-(3-dimethylaminopropyl)carbodiimide hydrochloride (557 mg) and 4-dimethylaminopyridine (148 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 350 mg of the title compound (yield 33%).

$^1$H NMR (400 MHz, CDCl$_3$) δ 1.27 (m, 3H), 1.46 (m, 9H), 1.49-1.75 (m, 2H), 1.84-2.03 (m, 2H), 2.97-3.30 (m, 3H), 4.11-4.27 (m, 2H), 4.61-4.82 (m, 2H), 4.86 (br.s., 0.5H), 5.47 (br.s., 1H), 7.24-7.40 (m, 5H); MS m/z 422 [M+H]$^+$.

Example 19 tert-Butyl (2S,5R)-5-((benzyloxy)amino)-2-((((1-phenylethylidene)amino)oxy) carbonyl)piperidine-1-carboxylate

[Chemical Formula 60]

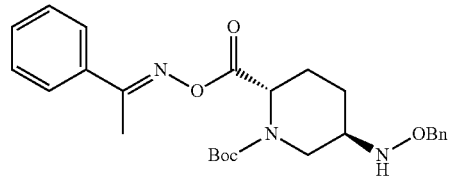

II-19

(2S,5R)-5-((Benzyloxy)amino)-1-(tert-butoxycarbonyl)piperidine-2-carboxylic acid (Reference Example 4, 2.54 g, 7.26 mmol) was dissolved in dehydrated dichloromethane (25 mL), and 1-ethyl-3-(3-dimethylaminopropyl)carbodiimide hydrochloride (1.67 g) and diisopropylethylamine (1.22 g) were added sequentially. To the mixture was added acetophenone oxime (1.47 g), followed by stirring at room temperature for 2.5 hours. The residue resulted from concentration of the reaction solution under reduced pressure was subjected to silica gel column chromatography (hexane/ethyl acetate=1/1) to afford 1.434 g of the title compound (yield 42%).

$^1$H NMR (400 MHz, CDCl$_3$) δ 1.42-1.53 (s, 9H), 1.61-1.81 (m, 2H), 2.05 (m, 2H), 2.37 (s, 3H), 3.11-3.38 (m, 2H), 4.19-4.37 (m, 1H), 4.64-4.83 (m, 2H), 5.51 (br.s., 1H), 7.25-7.51 (m, 10H); MS m/z 468 [M+H]$^+$.

Example 20

1-tert-Butyl 2-(1,3-dioxo-1,3-dihydro-2H-isoindol-2-yl) (2S,5R)-5-((benzyloxy)amino)piperidine-1,2-dicarboxylate

[Chemical Formula 61]

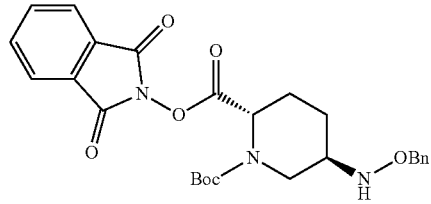

II-20

(2S,5R)-5-((Benzyloxy)amino)-1-(tert-butoxycarbonyl)piperidine-2-carboxylic acid (Reference Example 4, 1.40 g, 4.0 mmol) was dissolved in dehydrated dichloromethane (15 mL), and 2-hydroxy-1H-isoindol-1,3(2H)-dione (782 mg) was added, followed by ice cooling. To the mixture were sequentially added 1-ethyl-3-(3-dimethylaminopropyl)carbodiimide hydrochloride (920 mg) and 4-dimethylaminopyridine (244 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 1.71 g of the title compound (yield 86%).

¹H NMR (400 MHz, CDCl₃) δ 1.39-1.57 (m, 9H), 1.72-1.88 (m, 2H), 2.09-2.25 (m, 2H), 3.13-3.26 (m, 1H), 3.34 (br.s., 1H), 4.18-4.30 (m, 1H), 4.69-4.80 (m, 2H), 5.11 (br.s., 0.5H), 5.41 (br.s., 0.5H), 5.49 (br.s., 1H), 7.24-7.40 (m, 5H), 7.76-7.83 (m, 2H), 7.85-7.93 (m, 2H); MS m/z 496 [M+H]⁺.

Example 21

2-(1H-Benzotriazol-1-yl) 1-tert-butyl (2S,5R)-5-((benzyloxy)amino)piperidine-1,2-dicarboxylate or tert-butyl (2S,5R)-5-((benzyloxy)amino)-2-[(3-oxide-1H-Benzotriazolbenzotriazol-1-yl)carbonyl]piperidine-1-carboxylate

[Chemical Formula 62]

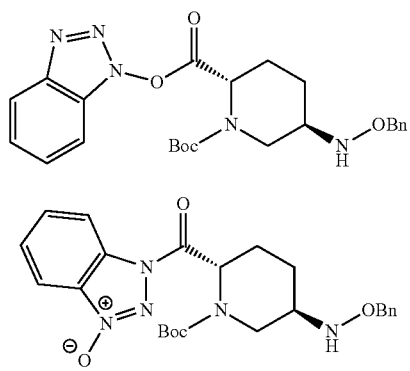

II-21-1

II-21-2

(2S,5R)-5-((Benzyloxy)amino)-1-(tert-butoxycarbonyl) piperidine-2-carboxylic acid (Reference Example 4, 401 mg, 1.14 mmol) was dissolved in dehydrated dichloromethane (4 mL), and 1-hydroxybenzotriazole (210 mg) was added, followed by ice cooling. To the mixture was added 1-ethyl-3-(3-dimethylaminopropyl) carbodiimide hydrochloride (263 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=3/1) to afford 333 mg of the title compounds as a mixture (yield 62%).

¹H NMR (400 MHz, CDCl₃) δ 1.35-1.64 (m, 9H), 1.69-1.92 (m, 2H), 2.08-2.38 (m, 2H), 3.18-3.48 (m, 2H), 4.05-4.16 (m, 1H), 4.67-4.83 (m, 2H), 5.25 (dd, J=5.7 & 3.9 Hz, 1H), 7.25-7.47 (m, 7H), 7.55 (m, 1H), 8.08 (m, 1H); MS m/z 468 [M+H]⁺.

Example 22

1-tert-Butyl 2-(4-oxo-1,2,3-benzotriazin-3(4H)-yl) (2S,5R)-5-((benzyloxy) amino)piperidine-1,2-dicarboxylate or tert-butyl (2S,5R)-5-((benzyloxy) amino)-2-[(3-oxido-4-oxo-1,2,3-benzotriazine-1(4H)-yl)carbonyl]piperidine-1-carboxylate

[Chemical Formula 63]

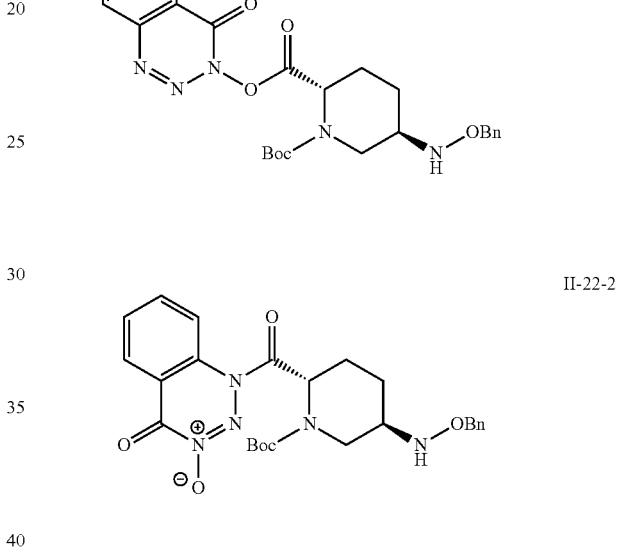

II-22-1

II-22-2

(2S,5R)-5-((Benzyloxy)amino)-1-(tert-butoxycarbonyl) piperidine-2-carboxylic acid (Reference Example 4, 402 mg, 1.15 mmol) was dissolved in dehydrated dichloromethane (8 mL), and 3-hydroxy-1,2,3-benzotriazine-4(3H)-one (224 mg) was added, followed by ice cooling. To the mixture were sequentially added 1-ethyl-3-(3-dimethylaminopropyl) carbodiimide hydrochloride (264 mg) and 4-dimethylaminopyridine (70 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 482 mg of the title compounds as a mixture (yield 85%).

¹H NMR (400 MHz, CDCl₃) δ 1.37-1.60 (m, 9H), 1.75-1.94 (m, 2H), 2.11-2.33 (m, 2H), 3.20-3.43 (m, 2H), 4.20-4.34 (m, 1H), 4.66-4.82 (m, 2H), 5.19 (br.s., 1H), 5.48 (br.s, 1H), 7.25-7.44 (m, 5H), 7.85 (m, 1H), 8.02 (m, 1H), 8.24 (d, J=7.9 Hz, 1H), 8.36 (d, J=8.1 Hz, 1H); MS m/z 496 [M+H]⁺.

Example 23 tert-Butyl (2S,5R)-5-((benzyloxy)amino)-2-((dodecylthio)carbonyl) piperidine-1-carboxylate

[Chemical Formula 64]

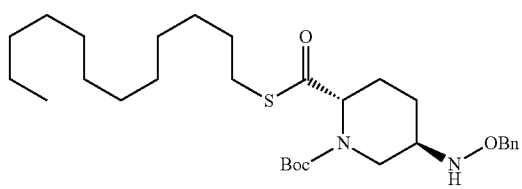

II-23

(2S,5R)-5-((Benzyloxy)amino)-1-(tert-butoxycarbonyl) piperidine-2-carboxylic acid (Reference Example 4, 1.2 g, 3.42 mmol) was dissolved in dehydrated dichloromethane (12 mL) under an Ar atmosphere, isobutyl chloroformate (490 mg) was added dropwise at −78° C., and subsequently diisopropylethylamine (464 mg) was added at the same temperature. After stirring for 30 minutes, 1-dodecanethiol (830 mg) was added dropwise slowly over 1 minute, followed by stirring at room temperature for 2 hours. The reaction solution was diluted with ethyl acetate (100 mL), washed sequentially with 8% citric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=2/1) to afford 104 mg of the title compound as an oil (yield 6%).

$^1$H NMR (400 MHz, CDCl$_3$) δ 0.82-0.97 (m, 5H), 1.14-1.40 (m, 12H), 1.41-1.67 (m, 17H), 1.79-2.15 (m, 2H), 2.88 (m, 2H), 3.13 (m, 2H), 3.88 (m, 1H), 4.27 (m, 1H), 4.61-4.81 (m, 2H), 5.41 (br.s., 1H), 7.28-7.41 (m, 5H), MS m/z 535 [M+H]$^+$.

Example 24 tert-Butyl (2S,5R)-5-((benzyloxy)amino)-2-(((4-(tert-butyl)phenyl)thio) carbonyl)piperidine-1-carboxylate

[Chemical Formula 65]

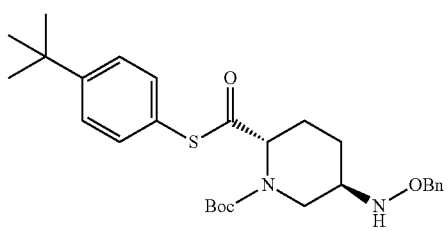

II-24

(2S,5R)-5-((Benzyloxy)amino)-1-(tert-butoxycarbonyl) piperidine-2-carboxylic acid (Reference Example 4, 1.2 g, 3.42 mmol) was dissolved in dehydrated dichloromethane (18 mL), and 1-ethyl-3-(3-dimethylaminopropyl)carbodiimide hydrochloride (690 mg) was added. To the mixture was added 4-tert-butylbenzenethiol (0.522 g), followed by stirring at room temperature for 2.5 hours. The reaction solution was diluted with ethyl acetate (100 mL), washed sequentially with 8% citric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 108.8 mg of the title compound (yield 6%).

1H NMR (400 MHz, CDCl$_3$) δ 1.27-1.36 (m, 18H), 1.67-1.77 (m, 2H), 1.87-2.18 (m, 2H), 3.11-3.32 (m, 2H), 4.26-4.46 (m, 1H), 4.67-4.83 (m, 2H), 5.45 (br.s., 1H), 7.25-7.51 (m, 9H); MS m/z 499 [M+H]$^+$.

Example 25 tert-Butyl (2S,5R)-5-((benzyloxy)amino)-2-(((4-nitrophenyl)thio)carbonyl) piperidine-1-carboxylate

[Chemical Formula 66]

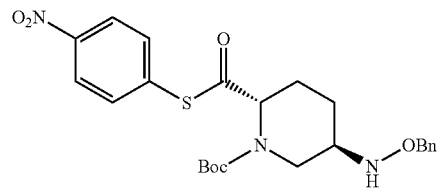

II-25

(2S,5R)-5-((Benzyloxy)amino)-1-(tert-butoxycarbonyl) piperidine-2-carboxylic acid (Reference Example 4, 1.2 g, 3.42 mmol) was dissolved in dehydrated dichloromethane (18 mL), and 1-ethyl-3-(3-dimethylaminopropyl)carbodiimide hydrochloride (983 mg) was added. To the mixture was added 4-nitrobenzenethiol (0.707 g), followed by stirring at room temperature for 2.5 hours. The reaction solution was diluted with ethyl acetate (100 mL), washed sequentially with 8% citric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 371 mg of the title compound (yield 22%).

$^1$H NMR (400 MHz, CDCl$_3$) δ 1.55 (s, 9H), 1.58 (m, 2H), 2.07 (m, 2H), 3.05-3.34 (m, 2H), 4.27-4.52 (m, 1H), 4.68-4.77 (m, 1H), 4.77-4.85 (m, 1H), 5.43 (br.s., 1H), 7.31-7.42 (m, 5H), 7.62 (d, J=8.8 Hz, 2H), 8.28 (d, J=8.8 Hz, 2H); MS m/z 488 [M+H]$^+$.

Example 26 tert-Butyl (2S,5R)-5-((benzyloxy)amino)-2-(((pyridine-2-yl)thio)carbonyl) piperidine-1-carboxylate

[Chemical Formula 67]

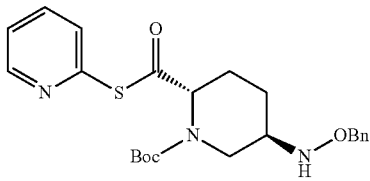

II-26

(2S,5R)-5-((Benzyloxy)amino)-1-(tert-butoxycarbonyl)piperidine-2-carboxylic acid (Reference Example 4, 1.75 g, 5.0 mmol) was dissolved in dehydrated dichloromethane (18 mL), and 2,2'-disulfanediyldipyridine (1.348 g, 6.0 mmol) and triphenylphosphine (1.622 g, 6.0 mmol) were added sequentially under ice cooling. Subsequently, stirring was carried out at room temperature for 0.6 hours. The residue resulted from concentration of the reaction solution under reduced pressure was subjected to silica gel column chromatography (hexane/ethyl acetate=1/2) to afford 2.03 g of the title compound (yield 91%).

1H NMR (400 MHz, CDCl$_3$) δ 1.61-1.71 (m, 2H), 1.91-2.13 (m, 2H), 3.08-3.33 (m, 2H), 4.27-4.45 (m, 1H), 4.68-4.79 (m, 2H), 5.41 (br.s., 1H), 7.26-7.39 (m, 6H), 7.61 (m, 1H), 7.74 (td, J=7.7 & 0.8 Hz, 1H), 8.64 (br.s., 1H); MS m/z 444 [M+H]$^+$.

Example 27 tert-Butyl (2S,5R)-5-((benzyloxy)amino)-2-(((5-nitropyridine-2-yl)thio) carbonyl)piperidine-1-carboxylate

[Chemical Formula 68]

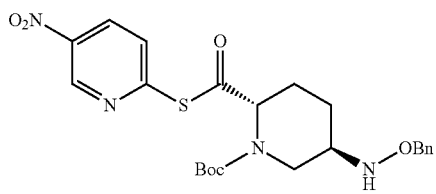

II-27

(2S,5R)-5-((Benzyloxy)amino)-1-(tert-butoxycarbonyl)piperidine-2-carboxylic acid (Reference Example 4, 1.75 g, 5.0 mmol) was dissolved in dehydrated dichloromethane (18 mL), and 2,2'-disulfanediylbis(5-nitropyridine) (1.94 g) and triphenylphosphine (1.622 g) were added sequentially under ice cooling. Subsequenty, stirring was carried out at room temperature for 1 hour. The residue resulted from concentration of the reaction solution under reduced pressure was subjected to silica gel column chromatography (hexane/ethyl acetate=1/1) to afford 2.306 g of the title compound (yield 94%).

$^1$H NMR (400 MHz, CDCl$_3$) δ 1.65 (m, 2H), 2.02 (m, 2H), 3.07-3.28 (m, 2H), 4.272-4.51 (m, 1H), 4.67-4.80 (m, 2H), 5.17 (br.s., 1H), 7.26-7.41 (m, 5H), 7.93 (m, 1H), 8.50 (dd, J=8.7 & 2.7 Hz, 1H), 9.40 (br.s., 1H); MS m/z 489 [M+H]$^+$.

Example 28 tert-Butyl (2S,5R)-5-((benzyloxy)amino)-2-((2-thioxo-1,3-thiazolidin-3-yl)carbonyl)piperidine-1-carboxylate

[Chemical Formula 69]

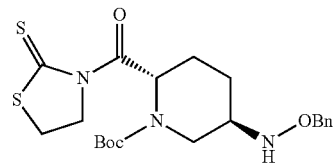

II-28

(2S,5R)-5-((Benzyloxy)amino)-1-(tert-butoxycarbonyl)piperidine-2-carboxylic acid (Reference Example 4, 379 mg, 1.08 mmol) was dissolved in dehydrated dichloromethane (7 mL), and 1,3-thiazolidine-2-thione (184 mg) was added, followed by ice cooling. To the mixture were sequentially added 1-ethyl-3-(3-dimethylaminopropyl)carbodiimide hydrochloride (295 mg) and 4-dimethylaminopyridine (63 mg), followed by stirring at room temperature for 4 hours. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 288 mg of the title compound (yield 59%).

$^1$H NMR (400 MHz, CDCl$_3$) δ 1.44 (br s, 9H), 1.49-1.90 (m, 3H), 2.09-2.21 (m, 1H), 3.13-4.22 (m, 5H), 4.45-4.63 (m, 2H), 4.66-4.78 (m, 2H), 4.74 (d, J=11.5 Hz, 1H), 5.44 (br.s., 1H), 6.19 (br.s., 0.5H), 6.51 (br.s., 0.5H), 7.24-7.39 (m, 5H); MS m/z 452 [M+H]$^+$.

Example 29 tert-Butyl (2S,5R)-5-((benzyloxy)amino)-2-((2-thioxo-1,3-oxazolidin-3-yl) carbonyl)piperidine-1-carboxylate

[Chemical Formula 70]

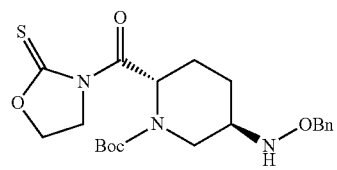

II-29

(2S,5R)-5-((Benzyloxy)amino)-1-(tert-butoxycarbonyl)piperidine-2-carboxylic acid (Reference Example 4, 755 mg, 2.15 mmol) was dissolved in dehydrated dichloromethane (8 mL), and 1,3-oxazolidine-2-thione (267 mg) was added, followed by ice cooling. To the mixture were sequentially added 1-ethyl-3-(3-dimethylaminopropyl)carbodiimide hydrochloride (496 mg) and 4-dimethylaminopyridine (55 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 334 mg of the title compound (yield 36%).

$^1$H NMR (400 MHz, CDCl$_3$) δ 1.44 (br.s., 9H), 1.49-1.90 (m, 3H), 2.09-2.21 (m, 1H), 3.13-4.22 (m, 5H), 4.45-4.63 (m, 2H), 4.66-4.78 (m, 2H), 4.74 (d, J=11.5 Hz, 1H) 5.44 (br.s., 1H), 6.19 (br.s., 0.5H), 6.51 (br.s., 0.5H), 7.24-7.39 (m, 5H); MS m/z 436 [M+H]$^+$.

Example 30 tert-Butyl 2-(2,5-dioxopyrrolidin-1-yl) (2S,5R)-5-((benzyloxy)amino) piperidine-1,2-dicarboxylate (II-30)

[Chemical Formula 71]

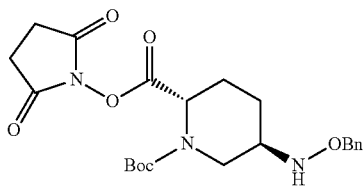

II-30

(2S,5R)-5-((Benzyloxy)amino)-1-(tert-butoxycarbonyl) piperidine-2-carboxylic acid (Reference Example 4, 6.75 g, 19.26 mmol) was dissolved in dehydrated dichloromethane (80 mL), and 1-hydroxypyrrolidine-2,5-dione (6.65 g) was added, followed by ice cooling. To the mixture were sequentially added 1-ethyl-3-(3-dimethylaminopropyl)carbodiimide hydrochloride (4.62 g) and 4-dimethylaminopyridine (1.2 g), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=1/1) to afford 5.61 g of the title compound (yield 71%).

$^1$H NMR (400 MHz, CDCl$_3$) δ 1.42-1.54 (m, 9H), 1.70-1.77 (m, 2H), 2.09-2.21 (m, 2H), 2.84 (br.s., 4H), 3.13-3.26 (m, 1H), 3.29 (br.s., 1H), 4.18-4.27 (m, 1H), 4.67-4.78 (m, 2H), 5.06 (br.s., 0.5H), 5.35 (br.s., 0.5H), 5.46 (br.s., 1H), 7.28-7.39 (m, 5H); MS m/z 448 [M+H]$^+$.

Example 31

1-tert-Butyl 2-(1R,2S,6R,7S)-3,5-dioxo-4-azatricyclo[5.2.1.0$^{2,6}$]dec-8-en-4-yl) (2S,5R)-5-((benzyloxy)amino)piperidine-1,2-dicarboxylate (II-31)

[Chemical Formula 72]

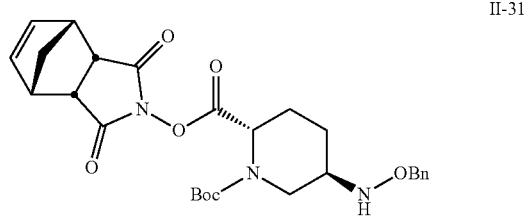

II-31

(2S,5R)-5-((Benzyloxy)amino)-1-(tert-butoxycarbonyl) piperidine-2-carboxylic acid (Reference Example 4, 1.40 g, 4.0 mmol) was dissolved in dehydrated dichloromethane (15 mL), and (1R,2S,6R,7S)-4-hydroxy-4-azatricyclo[5.2.1.0$^{2,6}$] dec-8-ene-3,5-dione (859 mg) was added, followed by ice cooling. To the mixture were sequentially added 1-ethyl-3-(3-dimethylaminopropyl)carbodiimide hydrochloride (920 mg) and 4-dimethylaminopyridine (244 mg), followed by stirring at room temperature overnight. The residue resulted from concentration of the reaction solution under reduced pressure was diluted with ethyl acetate, washed sequentially with ice-cold 10% citric acid, saturated sodium bicarbonate and saturated brine, dried over anhydrous magnesium sulfate and filtered, and the solvent was distilled off under reduced pressure. The residue was subjected to silica gel column chromatography (hexane/ethyl acetate=2/1) to afford 1.87 g of the title compound as a colorless crystalline powder (yield 92%).

$^1$H NMR (400 MHz, CDCl$_3$) δ 1.46 (s, 9H), 1.52 (m, 1H), 1.65-1.83 (m, 3H), 1.93-2.19 (m, 2H), 3.09-3.23 (m, 2H), 3.26 (m, 1H), 3.32 (br.s., 2H), 3.44 (br.s., 2H), 4.12-4.24 (m, 1H), 4.68 (d, J=11.5 Hz, 1H), 4.74 (d, J=11.5 Hz, 1H), 4.99 (br.s., 0.5H), 5.28 (br.s., 0.5H), 5.44 (br.s., 1H), 6.20 (br.s., 2H), 7.24-7.40 (m, 5H); MS m/z 512 [M+H]$^+$.

Example 32

Methyl (2S,5R)-6-(benzyloxy)-7-oxo-1,6-diazabicyclo[3.2.1]octane-2-carboxylate

[Chemical Formula 73]

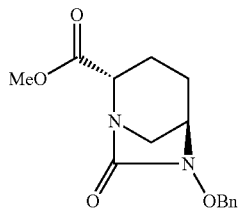

III-32

Step 1

1-tert-Butyl 2-methyl (2S,5R)-5-((benzyloxy) ((trichloromethoxy)carbonyl) amino)piperidine-1,2-dicarboxylate or 1-tert-butyl 2-methyl (2S,5R)-5-((benzyloxy) (chlorocarbonyl)amino)piperidine-1,2-dicarboxylate 1-tert-Butyl 2-methyl (2S,5R)-5-((benzyloxy)amino)piperidine-1,2-dicarboxylate (Example 1, 364 mg, 1 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

Methyl (2S,5R)-5-((benzyloxy)((trichloromethoxy) carbonyl)amino) piperidine-2-carboxylate or methyl (2S,5R)-5-((benzyloxy)(chlorocarbonyl) amino) piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compound was subjected to the next step without purification and isolation.

Step 3

Methyl (2S,5R)-6-(benzyloxy)-7-oxo-1,6-diazabicyclo[3.2.1]octane-2-carboxylate

The mixture in Step 2 above was added dropwise to ice-cold 1 M potassium bicarbonate (1.1 g/9 mL), followed by stirring for 0.5 hours. To the mixture was added ethyl acetate (65 mL), layers are separated, the organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/1) to afford 215 mg of the title compound as a colorless crystalline powder (total yield over three steps: 74%).

$^1$H NMR (400 MHz, CDCl$_3$) δ 1.26 (m, 1H), 1.63-1.73 (m, 1H), 1.99-2.15 (m, 2H), 2.90 (d, J=12.0 Hz, 1H), 3.07 (br.d., J=12.0 Hz, 1H), 3.32 (m, 1H), 3.78 (s, 3H), 4.08-4.17 (m, 1H), 4.90 (d, J=11.4 Hz, 1H), 5.06 (d, J=11.4 Hz, 1H), 7.33-7.46 (m, 5H); MS m/z 291 [M+H]$^+$.

Example 33

Ethyl (2S,5R)-6-(benzyloxy)-7-oxo-1,6-diazabicyclo[3.2.1]octane-2-carboxylate

[Chemical Formula 74]

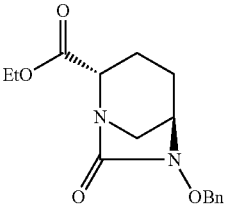

III-33

Step 1

1-tert-Butyl 2-ethyl (2S,5R)-5-((benzyloxy)((trichloromethoxy)carbonyl)amino) piperidine-1,2-dicarboxylate or 1-tert-butyl 2-ethyl (2S,5R)-5-((benzyloxy) (chlorocarbonyl)amino)piperidine-1,2-dicarboxylate 1-tert-Butyl 2-ethyl (2S,5R)-5-((benzyloxy)amino)piperidine-1,2-dicarboxylate (Example 2, 398 mg, 1.05 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

Ethyl (2S,5R)-5-((benzyloxy)((trichloromethoxy) carbonyl)amino) piperidine-2-carboxylate or ethyl (2S,5R)-5-((benzyloxy)(chlorocarbonyl)amino) piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

Ethyl (2S,5R)-6-(benzyloxy)-7-oxo-1,6-diazabicyclo[3.2.1]octane-2-carboxylate

The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/3) to afford 271 mg of the title compound (total yield over three steps: 85%).

$^1$H NMR (400 MHz, CDCl$_3$) δ 1.30 (m, 3H), 1.55-1.76 (m, 1H), 1.97-2.17 (m, 3H), 2.93 (d, J=12.0 Hz, 1H), 3.06 (br.d., J=12.0 Hz, 1H), 3.32 (m, 1H), 4.10 (m, 1H), 4.17-4.31 (m, 2H), 4.90 (d, J=11.4 Hz, 1H), 5.06 (d, J=11.4 Hz, 1H), 7.31-7.47 (m, 5H); MS m/z 305 [M+H]$^+$.

Example 34

Allyl (2S,5R)-6-(benzyloxy)-7-oxo-1,6-diazabicyclo[3.2.1]octane-2-carboxylate

[Chemical Formula 75]

III-34

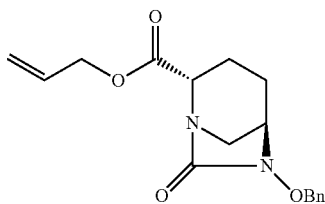

Step 1

2-Allyl 1-tert-butyl (2S,5R)-5-((benzyloxy)((trichloromethoxy)carbonyl) amino)piperidine-1,2-dicarboxylate or 2-allyl 1-tert-butyl (2S,5R)-5-((benzyloxy) (chlorocarbonyl)amino)piperidine-1,2-dicarboxylate 2-Allyl 1-tert-butyl (2S,5R)-5-((benzyloxy)amino)piperidine-1,2-dicarboxylate (Example 3, 390 mg, 1.0 mmol) was dissolved in dehydrated dichloromethane (8 mL), and diisopropylethylamine (258 mg) was added, followed by ice cooling. To the mixture was added triphosgene (169 mg), followed by stirring for 20 minutes, and the completion of the reaction for the title compounds was confirmed by TLC. The compounds were subjected to the next step without purification and isolation.

Step 2

Allyl (2S,5R)-5-((benzyloxy)((trichloromethoxy)carbonyl)amino) piperidine-2-carboxylate or allyl (2S,5R)-5-((benzyloxy)(chlorocarbonyl)amino) piperidine-2-carboxylate, methanesulfonate To the mixture in Step 1 above was added methanesulfonic acid (947 mg) under ice cooling, followed by stirring for 40 minutes, and the completion of the reaction for the title compounds was confirmed by TLC. The compounds were subjected to the next step without purification and isolation.

Step 3

Allyl (2S,5R)-6-(benzyloxy)-7-oxo-1,6-diazabicyclo[3.2.1]octane-2-carboxylate

The mixture in Step 2 above was added dropwise to 1 M potassium bicarbonate (9 mL), followed by stirring overnight. The reaction solvent was diluted with ethyl acetate (100 mL), washed sequentially with 0.1 M hydrochloric acid (100 mL), saturated sodium bicarbonate (100 mL) and saturated brine (100 mL) sequentially, dried over anhydrous magnesium sulfate, filtered, and concentrated under reduced pressure. The residue was subjected to silica gel column chromatography (hexane/ethyl acetate=1/1) to afford 38.4 mg of the title compound as oil (total yield over three steps: 12%).

$^1$H NMR (400 MHz, CDCl$_3$) δ 1.69 (m, 1H), 2.02-2.15 (m, 3H), 2.93 (d, J=12.0 Hz, 1H), 3.07 (m, 1H), 3.31 (m, 1H), 4.14 (dd, J=6.5, 2.6 Hz, 1H), 4.67 (ddd, J=5.9, 1.5, 1.2 Hz, 1H), 4.91 (d, J=11.5 Hz, 1H), 5.06 (d, J=11.5 Hz, 1H), 5.26 (m, 1H), 5.34 (m, 1H), 5.92 (m, 1H), 7.36-7.42 (m, 5H); MS m/z 317 [M+H]$^+$.

Example 35

Benzyl (2S,5R)-6-(benzyloxy)-7-oxo-1,6-diazabicyclo[3.2.1]octane-2-carboxylate

[Chemical Formula 76]

III-35

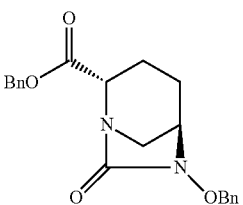

Step 1

2-Benzyl 1-tert-butyl (2S,5R)-5-((benzyloxy)((trichloromethoxy)carbonyl) amino)piperidine-1,2-dicarboxylate or 2-benzyl 1-tert-butyl (2S,5R)-5-((benzyloxy) (chlorocarbonyl)amino)piperidine-1,2-dicarboxylate 2-Benzyl 1-tert-butyl (2S,5R)-5-((benzyloxy)amino)piperidine-1,2-dicarboxylate (Example 4, 451 mg, 1.02 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

Benzyl (2S,5R)-5-((benzyloxy)((trichloromethoxy) carbonyl)amino)piperidine-2-carboxylate or benzyl (2S,5R)-5-((benzyloxy)(chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

Benzyl (2S,5R)-6-(benzyloxy)-7-oxo-1,6-diazabicyclo[3.2.1]octane-2-carboxylate

The mixture in Step 2 above was added dropwise to 1 M potassium bicarbonate (1.1 g/9 mL), followed by stirring for 0.5 hours. The reaction solvent was diluted with ethyl acetate (65 mL), washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/2) to afford 301 mg of the title compound (total yield over three steps: 80%).

$^1$H NMR (400 MHz, CDCl$_3$) δ 1.59-1.68 (m, 1H), 2.01-2.20 (m, 3H), 2.89 (d, J=11.9 Hz, 2H), 3.05 (d, J=11.9 Hz, 2H), 3.30 (br.s., 1H), 4.16 (m, 1H), 4.92 (d, J=11.4 Hz, 1H), 5.07 (d, J=11.4 Hz, 1H), 5.24 (s, 2H), 7.32-7.46 (m, 10H); MS m/z 367 [M+H]$^+$.

Example 36

Cyanomethyl (2S,5R)-6-(benzyloxy)-7-oxo-1,6-diazabicyclo[3.2.1]octane-2-carboxylate

[Chemical Formula 77]

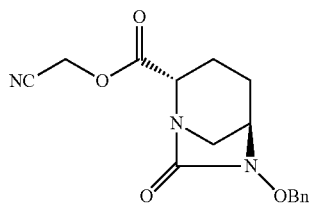

III-36

Step 1

1-tert-Butyl 2-(cyanomethyl) (2S,5R)-5-((benzyloxy)((trichloromethoxy)carbonyl) amino)piperidine-1,2-dicarboxylate or 1-tert-butyl 2-(cyanomethyl) (2S,5R)-5-((benzyloxy)(chlorocarbonyl) amino)piperidine-1,2-dicarboxylate 1-tert-Butyl 2-cyanomethyl (2S,5R)-5-((benzyloxy) amino)piperidine-1,2-dicarboxylate (Example 5, 403 mg, 1.03 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

Cyanomethyl (2S,5R)-5-((benzyloxy)((trichloromethoxy)carbonyl)amino) piperidine-2-carboxylate or cyanomethyl (2S,5R)-5-((benzyloxy)(chlorocarbonyl) amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

Cyanomethyl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/2) to afford 228 mg of the title compound (total yield over three steps: 70%).

$^1$H NMR (400 MHz, CDCl$_3$) δ 1.53 (m, 1H), 1.63-1.75 (m, 1H), 2.03-2.23 (m, 2H), 2.86 (d, J=12.0 Hz, 1H), 3.07-3.14 (m, 1H), 3.34 (m, 1H), 4.21 (d, J=6.7 Hz, 1H), 4.80 (m, 2H), 4.91 (d, J=11.4 Hz, 1H), 5.06 (d, J=11.4 Hz, 1H), 7.33-7.47 (m, 5H); MS m/z 316 [M+H]$^+$.

Example 37

4-Chlorophenyl (2S,5R)-6-(benzyloxy)-7-oxo-1,6-diazabicyclo[3.2.1]octane-2-carboxylate

[Chemical Formula 78]

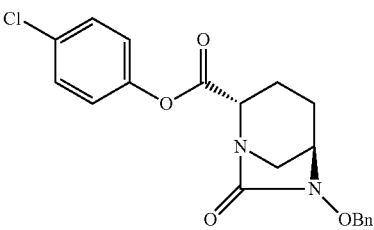

III-37

Step 1

1-tert-Butyl 2-(4-chlorophenyl) (2S,5R)-5-((benzyloxy)((trichloromethoxy) carbonyl)amino)piperidine-1,2-dicarboxylate or 1-tert-butyl 2-(4-chlorophenyl) (2S,5R)-5-((benzyloxy)(chlorocarbonyl) amino)piperidine-1,2-dicarboxylate 1-tert-Butyl 2-(4-chlorophenyl) (2S,5R)-5-((benzyloxy) amino)piperidine-1,2-dicarboxylate (Example 6, 504 mg, 1.09 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

4-Chlorophenyl (2S,5R)-5-((benzyloxy)((trichloromethoxy)carbonyl)amino) piperidine-2-carboxylate or 4-chlorophenyl (2S,5R)-5-((benzyloxy)(chlorocarbonyl) amino)piperidine-2-carboxylate, methanesulfonate To the mixture in Step 1 above was added methanesulfonic acid (0.65 mL) under ice cooling, followed by stirring for 5 minutes, and the completion of the reaction for the title compound was confirmed by TLC. This compound was subjected to the next step without purification and isolation.

Step 3

4-Chlorophenyl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours, ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=3/1) to afford 207 mg of the title compound (total yield over three steps: 49%).

$^1$H NMR (400 MHz, CDCl$_3$) δ 1.67-1.80 (m, 1H), 2.06-2.28 (m, 3H), 3.05 (d, J=11.9 Hz, 1H), 3.16 (dt, J=11.9 & 3.1 Hz, 1H), 3.37 (m, 1H), 4.36 (dd, J=7.2 & 1.9 Hz, 1H), 4.93 (d, J=11.4 Hz, 1H), 5.08 (d, J=11.4 Hz, 1H), 7.05 (m, 2H), 7.31-7.49 (m, 7H); MS m/z 387 [M+H]$^+$.

Example 38

2,4,6-Trichlorophenyl (2S,5R)-6-(benzyloxy)-7-oxo-1,6-diazabicyclo[3.2.1]octane-2-carboxylate

[Chemical Formula 79]

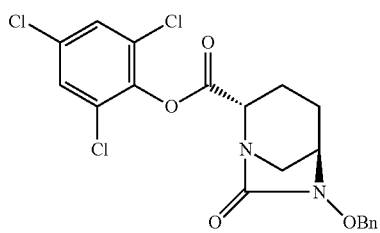

III-38

Step 1

1-tert-Butyl 2-(2,4,6-trichlorophenyl) (2S,5R)-5-((benzyloxy) ((trichloromethoxy)carbonyl)amino) piperidine-1,2-dicarboxylate or 1-tert-butyl 2-(2,4,6-trichlorophenyl) (2S,5R)-5-((benzyloxy) (chlorocarbonyl)amino) piperidine-1,2-dicarboxylate 1-tert-Butyl 2-(2,4,6-trichlorophenyl) (2S,5R)-5-((benzyloxy)amino) piperidine-1,2-dicarboxylate (Example 7, 530 mg, 1.00 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

2,4,6-Trichlorophenyl (2S,5R)-5-((benzyloxy) ((trichloromethoxy)carbonyl) amino)piperidine-2-carboxylate or 2,4,6-trichlorophenyl (2S,5R)-5-((benzyloxy) (chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

2,4,6-Trichlorophenyl (2S,5R)-6-(benzyloxy)-7-oxo-1,6-diazabicyclo [3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=5/1) to afford 207 mg of the title compound (total yield over three steps: 45%).

$^1$H NMR (400 MHz, CDCl$_3$) δ 1.67-1.81 (m, 1H), 2.07-2.19 (m, 1H), 2.25-2.35 (m, 2H), 3.19 (m, 1H), 3.34 (m, 1H), 4.50 (t, J=4.7 Hz, 1H), 4.93 (d, J=11.4 Hz, 1H), 5.09 (d, J=11.4 Hz, 1H), 7.32-7.52 (m, 7H); MS m/z 455 [M+H]$^+$

Example 39

2,3,4,5,6-Pentafluorophenyl (2S,5R)-6-(benzyloxy)-7-oxo-1,6-diazabicyclo [3.2.1]octane-2-carboxylate

[Chemical Formula 80]

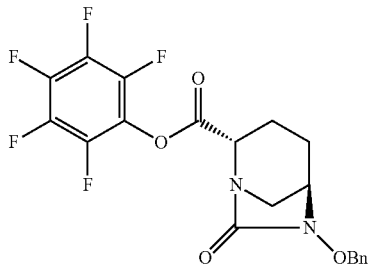

III-39

Step 1

1-tert-Butyl 2-(2,3,4,5,6-pentafluorophenyl) (2S, 5R)-5-((benzyloxy)((trichloromethoxy) carbonyl) amino)piperidine-1,2-dicarboxylate or 1-tert-butyl 2-(2,3,4,5,6-pentafluorophenyl) (2S,5R)-5-((benzyloxy)(chlorocarbonyl)amino)piperidine-1,2-dicarboxylate 1-tert-Butyl 2-(2,3,4,5,6-pentafluorophenyl) (2S,5R)-5-((benzyloxy)amino) piperidine-1,2-dicarboxylate (Example 8, 524 mg, 1.00 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

2,3,4,5,6-Pentafluorophenyl (2S,5R)-5-((benzyloxy)((trichloromethoxy)carbonyl)amino) piperidine-2-carboxylate or 2,3,4,5,6-pentafluorophenyl (2S,5R)-5-((benzyloxy) (chlorocarbonyl)amino)piperidine-2-carboxylate, methanesulfonate To the mixture in Step 1 above was added methanesulfonic acid (0.65 mL) under ice cooling, followed by stirring for 5 minutes, the completion of the reaction for the title compounds was confirmed by TLC. The compounds were subjected to the next step without purification and isolation.

Step 3

2,3,4,5,6-Pentafluorophenyl (2S,5R)-6-(benzyloxy)-7-oxo-1,6-diazabicyclo [3.2.1]octane-2-carboxylate The mixture in Step 2 above was added dropwise to ice-cold 1 M potassium bicarbonate (1.1 g/9 mL), followed by stirring for 0.5 hours. To the mixture was added ethyl acetate (65 mL) and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=6/1) to afford 295 mg of the title compound (total yield over three steps: 66%).

$^1$H NMR (400 MHz, CDCl$_3$) δ 1.65-1.80 (m, 1H), 2.07-2.36 (m, 3H), 2.98 (d, J=12.0 Hz, 1H), 3.19 (m, 1H), 3.37 (m, 1H), 4.50 (d, J=7.2 Hz, 1H), 4.93 (d, J=11.4 Hz, 1H), 5.09 (d, J=11.4 Hz, 1H), 7.32-7.49 (m, 5H); MS m/z 443 [M+H]$^+$

Example 40

4-Nitrophenyl (2S,5R)-6-(benzyloxy)-7-oxo-1,6-diazabicyclo[3.2.1]octane-2-carboxylate

[Chemical Formula 81]

III-40

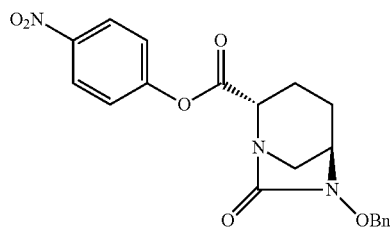

Step 1

1-tert-Butyl 2-(4-nitrophenyl) (2S,5R)-5-((benzyloxy)((trichloromethoxy) carbonyl)amino)piperidine-1,2-dicarboxylate or 1-tert-butyl 2-(4-nitrophenyl) (2S,5R)-5-((benzyloxy)(chlorocarbonyl)amino) piperidine-1,2-dicarboxylate 1-tert-Butyl 2-(4-nitrophenyl) (2S,5R)-5-((benzyloxy)amino)piperidine-1,2-dicarboxylate (Example 9, 470 mg, 1 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

4-Nitrophenyl (2S,5R)-5-((benzyloxy)((trichloromethoxy)carbonyl)amino) piperidine-2-carboxylate or 4-nitrophenyl (2S,5R)-5-((benzyloxy)(chlorocarbonyl) amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

4-Nitrophenyl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with ethyl acetate/hexane (1/1) and dried to afford 211 mg of the title compound (total yield over three steps: 53%).

$^1$H NMR (400 MHz, CDCl$_3$) δ 1.69-1.81 (m, 1H), 2.09-2.32 (m, 3H), 3.04 (d, J=11.9 Hz, 1H), 3.18 (m, 1H), 3.39 (m, 1H), 4.41 (dd, J=7.5 & 1.9 Hz, 1H), 4.94 (d, J=11.4 Hz, 1H), 5.09 (d, J=11.4 Hz, 1H), 7.28-7.34 (m, 2H), 7.35-7.53 (m, 5H), 8.25-8.38 (m, 2H); MS m/z 398 [M+H]$^+$.

Example 41

4-Cyanophenyl (2S,5R)-6-(benzyloxy)-7-oxo-1,6-diazabicyclo[3.2.1]octane-2-carboxylate

[Chemical Formula 82]

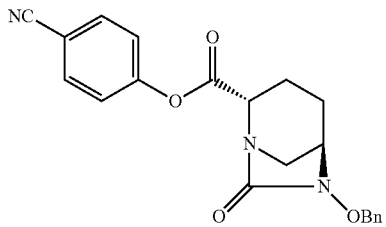

III-41

Step 1

1-tert-Butyl 2-(4-cyanophenyl) (2S,5R)-5-((benzyloxy)((trichloromethoxy) carbonyl)amino)piperidine-1,2-dicarboxylate or 1-tert-butyl 2-(4-cyanophenyl) (2S,5R)-5-((benzyloxy)(chlorocarbonyl)amino)piperidine-1,2-dicarboxylate 1-tert-Butyl 2-(4-cyanophenyl) (2S,5R)-5-((benzyloxy)amino)piperidine-1,2-dicarboxylate (Example 10, 460 mg, 1.02 mmol) was dissolved in dehydrated dichloromethane (6 mL), and diisopropylethylamine (260 mg) was added, followed by ice cooling. To the mixture was added triphosgene (170 mg), followed by stirring for 0.5 hours, and the completion of the reaction for the title compounds was confirmed by TLC. The compounds were subjected to the next step without purification and isolation.

Step 2

4-Cyanophenyl (2S,5R)-5-((benzyloxy)((trichloromethoxy)carbonyl) amino)piperidine-2-carboxylate or 4-cyanophenyl (2S,5R)-5-((benzyloxy)(chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

4-Cyanophenyl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=2/1) to afford 73 mg of the title compound (total yield over three steps: 19%).

$^1$H NMR (400 MHz, CDCl$_3$) δ 1.67-1.82 (m, 1H), 2.06-2.30 (m, 3H), 3.06 (m, 1H), 3.17 (m, 1H), 3.38 (m, 1H), 3.92 (m, 3H), 4.39 (dd, J=7.2 & 2.0 Hz, 1H), 4.93 (d, J=11.4 Hz, 1H), 5.09 (d, J=11.4 Hz, 1H), 7.13-7.50 (m, 7H), 8.04-8.17 (m, 2H); MS m/z 378 [M+H]$^+$.

Example 42

4-Carbamoylphenyl (2S,5R)-6-(benzyloxy)-7-oxo-1,6-diazabicyclo[3.2.1] octane-2-carboxylate

[Chemical Formula 83]

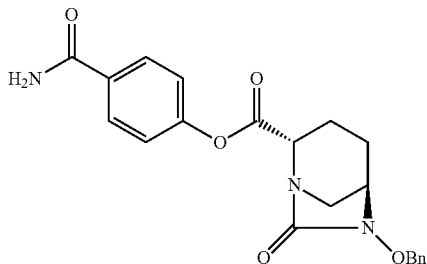

III-42

Step 1

1-tert-Butyl 2-(4-carbamoylphenyl) (2S,5R)-5-((benzyloxy) ((trichloromethoxy)carbonyl)amino) piperidine-1,2-dicarboxylate or 1-tert-butyl 2-(4-carbamoylphenyl) (2S,5R)-5-((benzyloxy) (chlorocarbonyl)amino)piperidine-1,2-dicarboxylate 1-tert-Butyl 2-(4-carbamoylphenyl) (2S,5R)-5-((benzyloxy)amino)piperidine-1,2-dicarboxylate (Example 11, 739 mg, 1.57 mmol) was dissolved in dehydrated dichloromethane (14 mL), followed by ice cooling. Diisopropylethylamine (407 mg) and triphosgene (275 mg) were added, followed by stirring for 0.5 hours, and the completion of the reaction for the title compounds was confirmed by TLC. The compounds were subjected to the next step without purification and isolation.

Step 2

4-Carbamoylphenyl (2S,5R)-5-((benzyloxy) ((trichloromethoxy)carbonyl) amino)piperidine-2-carboxylate or 4-carbamoylphenyl (2S,5R)-5-((benzyloxy) (chlorocarbonyl)amino)piperidine-2-carboxylate, methanesulfonate To the mixture in Step 1 above was added methanesulfonic acid (1.04 mL) under ice cooling, followed by stirring for 15 minutes, and the completion of the reaction for the title compounds was confirmed by TLC. The compounds were subjected to the next step without purification and isolation.

Step 3

4-Carbamoylphenyl (2S,5R)-6-(benzyloxy)-7-oxo-1,6-diazabicyclo[3.2.1] octane-2-carboxylate The mixture in Step 2 above was added dropwise to ice-cold 1 M potassium bicarbonate (1.76 g/18 mL), followed by stirring for 0.5 hours. Ethyl acetate (70 mL) was added and the layers were separated. The organic layer was then washed with 10% citric acid (20 mL), saturated sodium bicarbonate (20 mL) and saturated brine (20 mL). The organic layer was dried over anhydrous sodium sulfate, filtered and then concentrated under reduced pressure. The residue was subjected to silica gel column chromatography (hexane/ethyl acetate=1/2 to 0/10) to afford 382 mg of the title compound (total yield over three steps: 61%).

$^1$H NMR (400 MHz, CDCl$_3$) δ 1.70-1.80 (m, 1H), 2.08-2.30 (m, 3H), 3.07 (d, J=12.0 Hz, 1H), 3.18-3.20 (m, 1H), 3.39 (m, 1H), 4.39 (dd, J=7.1 & 2.2 Hz, 1H), 4.93 (d, J=11.4 Hz, 1H), 5.08 (d, J=11.4 Hz, 1H), 5.50-6.30 (m, 2H), 7.20 (m, 2H), 7.35-7.53 (m, 5H), 7.86 (m, 2H); MS m/z 396 [M+H]$^+$.

Example 43

4-Methoxycarbonylphenyl (2S,5R)-6-(benzyloxy)-7-oxo-1,6-diazabicyclo[3.2.1] octane-2-carboxylate

[Chemical Formula 84]

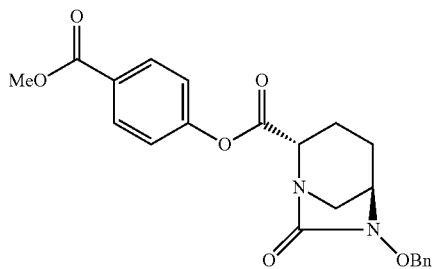

III-43

Step 1

1-tert-Butyl 2-(4-methoxycarbonylphenyl) (2S,5R)-5-((benzyloxy) ((trichloromethoxy)carbonyl)amino) piperidine-1,2-dicarboxylate or 1-tert-butyl 2-(4-methoxycarbonylphenyl) (2S,5R)-5-((benzyloxy) (chlorocarbonyl)amino) piperidine-1,2-dicarboxylate 1-tert-Butyl 2-(4-methoxycarbonylphenyl) (2S,5R)-5-((benzyloxy)amino) piperidine-1,2-dicarboxylate (Example 12, 628 mg, 1.30 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

4-Methoxycarbonylphenyl (2S,5R)-5-((benzyloxy) ((trichloromethoxy) carbonyl)amino)piperidine-2-carboxylate or 4-methoxycarbonylphenyl (2S,5R)-5-((benzyloxy)(chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

4-Methoxycarbonylphenyl (2S,5R)-6-(benzyloxy)-7-oxo-1,6-diazabicyclo [3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with ethyl acetate/hexane (1/1) and dried to afford 180 mg of the title compound (total yield over three steps: 34%).

$^1$H NMR (400 MHz, CDCl$_3$) δ 1.67-1.82 (m, 1H), 2.06-2.30 (m, 3H), 3.06 (m, 1H), 3.17 (m, 1H), 3.38 (m, 1H), 3.92 (m, 3H), 4.39 (dd, J=7.2 & 2.0 Hz, 1H), 4.93 (d, J=11.4 Hz, 1H), 5.09 (d, J=11.4 Hz, 1H), 7.13-7.50 (m, 7H), 8.04-8.17 (m, 2H); MS m/z 411 [M+H]$^+$.

Example 44

4-Methylsulfonylphenyl (2S,5R)-6-(benzyloxy)-7-oxo-1,6-diazabicyclo[3.2.1] octane-2-carboxylate

[Chemical Formula 85]

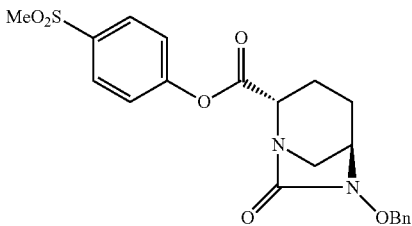

III-44

Step 1

1-tert-Butyl 2-(4-methylsulfonylphenyl) (2S,5R)-5-((benzyloxy) ((trichloromethoxy)carbonyl)amino) piperidine-1,2-dicarboxylate or 1-tert-butyl 2-(4-methylsulfonylphenyl) (2S,5R)-5-((benzyloxy) (chlorocarbonyl)amino)piperidine-1,2-dicarboxylate 1-tert-Butyl 2-(4-methylsulfonylphenyl) (2S,5R)-5-((benzyloxy)amino) piperidine-1,2-dicarboxylate (Example 13, 493 mg, 0.98 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

4-Methylsulfonylphenyl (2S,5R)-5-((benzyloxy)((trichloromethoxy)carbonyl) amino)piperidine-2-carboxylate or 4-methylsulfonylphenyl (2S,5R)-5-((benzyloxy)(chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

4-Methylsulfonylphenyl (2S,5R)-6-(benzyloxy)-7-oxo-1,6-diazabicyclo[3.2.1] octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with hexane/ethyl acetate (1/1), filtered and dried to afford 239 mg of the title compound (total yield over three steps: 57%).
$^1$H NMR (400 MHz, CDCl$_3$) δ 1.69-1.81 (m, 1H), 2.07-2.34 (m, 3H), 2.99-3.11 (m, 4H), 3.13-3.23 (m, 1H), 3.39 (m, 1H), 4.41 (d, J=5.5 Hz, 1H), 4.94 (d, J=11.4 Hz, 1H), 5.09 (d, J=11.4 Hz, 1H), 7.29-7.58 (m, 7H), 7.94-8.11 (m, 2H); MS m/z 431 [M+H]$^+$.

Example 45

Quinolin-8-yl (2S,5R)-6-(benzyloxy)-7-oxo-1,6-diazabicyclo[3.2.1] octane-2-carboxylate

[Chemical Formula 86]

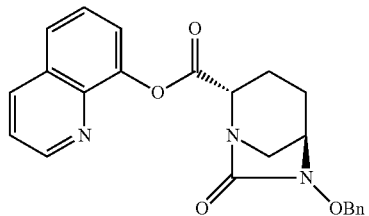

III-45

Step 1

1-tert-Butyl 2-(quinolin-8-yl) (2S,5R)-5-((benzyloxy)((trichloromethoxy) carbonyl)amino)piperidine-1,2-dicarboxylate or 1-tert-butyl 2-(quinolin-8-yl) (2S,5R)-5-((benzyloxy)(chlorocarbonyl)amino)piperidine-1,2-dicarboxylate 1-tert-Butyl 2-(quinolin-8-yl) (2S,5R)-5-((benzyloxy)amino)piperidine-1,2-dicarboxylate (Example 15, 488 mg, 1.02 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

Quinolin-8-yl (2S,5R)-5-((benzyloxy)((trichloromethoxy)carbonyl) amino)piperidine-2-carboxylate or quinolin-8-yl (2S,5R)-5-((benzyloxy) (chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

Quinolin-8-yl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/1) to afford 265 mg of the title compound (total yield over three steps: 64%).
$^1$H NMR (400 MHz, CDCl$_3$) δ 1.87-2.02 (m, 1H), 2.07-2.21 (m, 1H), 2.24-2.39 (m, 1H), 2.45 (dd, J=15.3 & 6.8 Hz, 1H), 3.20 (br d, J=12.0 Hz, 1H), 3.44 (br.s., 1H), 3.83 (d, J=12.0 Hz, 1H), 4.58 (d, J=7.7 Hz, 1H), 4.96 (d, J=11.3 Hz, 1H), 5.11 (d, J=11.3 Hz, 1H), 7.29-7.57 (m, 8H), 7.72 (d, J=7.2 Hz, 1H), 8.16 (m, 1H), 8.80 (m, 1H); MS m/z 404 [M+H]$^+$

Example 46

5-Chloroquinolin-8-yl (2S,5R)-6-(benzyloxy)-7-oxo-1,6-diazabicyclo[3.2.1] octane-2-carboxylate

[Chemical Formula 87]

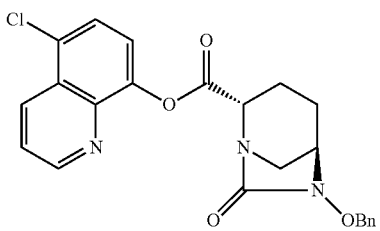

III-46

Step 1

1-tert-Butyl 2-(5-chloroquinolin-8-yl) (2S,5R)-5-((benzyloxy) ((trichloromethoxy)carbonyl)amino) piperidine-1,2-dicarboxylate or 1-tert-butyl 2-(5-chloroquinolin-8-yl) (2S,5R)-5-((benzyloxy) (chlorocarbonyl)amino) piperidine-1,2-dicarboxylate 1-tert-Butyl 2-(5-chloroquinolin-8-yl) (2S,5R)-5-((benzyloxy)amino) piperidine-1,2-dicarboxylate (Example 16, 586 mg, 1.14 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

5-Chloroquinolin-8-yl (2S,5R)-5-((benzyloxy) ((trichloromethoxy)carbonyl) amino)piperidine-2-carboxylate or 5-chloroquinolin-8-yl (2S,5R)-5-((benzyloxy) (chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

5-Chloroquinolin-8-yl (2S,5R)-6-(benzyloxy)-7-oxo-1,6-diazabicyclo[3.2.1] octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with a small portion of ethyl acetate to afford 178 mg of the title compound (total yield over three steps: 36%).

$^1$H NMR (400 MHz, CDCl$_3$) δ 1.84-1.99 (m, 1H), 2.09-2.21 (m, 1H), 2.24-2.48 (m, 2H), 3.20 (m, 1H), 3.42 (br.s., 1H), 3.75 (d, J=12.0 Hz, 1H), 4.57 (d, J=7.7 Hz, 1H), 4.96 (d, J=11.4 Hz, 1H), 5.12 (d, J=11.4 Hz, 1H), 7.33-7.58 (m, 7H), 7.62 (d, J=8.2 Hz, 1H), 8.57 (dd, J=8.6 & 1.6 Hz, 1H) 8.86 (dd, J=4.2 & 1.6 Hz, 1H); MS m/z 438 [M+H]$^+$

Example 47

Diethylamino (2S,5R)-6-(benzyloxy)-7-oxo-1,6-diazabicyclo[3.2.1]octane-2-carboxylate

[Chemical Formula 88]

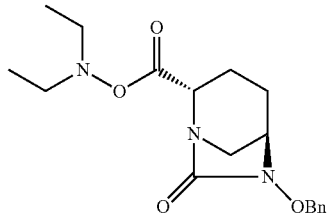

III-47

Step 1 tert-Butyl (2S,5R)-5-((benzyloxy)((trichloromethoxy)carbonyl)amino)-2-(((diethylamino)oxy)carbonyl)piperidine-1-carboxylate or tert-butyl (2S,5R)-5-((benzyloxy)(chlorocarbonyl)amino)-2-(((diethylamino)oxy)carbonyl)piperidine-1-carboxylate tert-Butyl (2S,5R)-5-((benzyloxy)amino)-2-(((diethylamino)oxy)carbonyl) piperidine-1-carboxylate (Example 18, 424 mg, 1.00 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-(((diethylamino) oxy)carbonyl)piperidine or (2S,5R)-5-((benzyloxy)(chlorocarbonyl) amino)-2-(((diethylamino)oxy)carbonyl)piperidine, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

Diethylamino (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=2/1) to afford 203 mg of the title compound (total yield over three steps: 58%).

$^1$H NMR (400 MHz, CDCl$_3$) δ 1.05-1.18 (m, 6H), 1.64-1.80 (m, 1H), 1.97-2.19 (m, 3H), 2.88-2.99 (m, 4H), 3.04 (s, 2H), 3.30 (br.s., 1H), 4.13 (m, 1H), 4.90 (d, J=11.4 Hz, 1H), 5.05 (d, J=11.4 Hz, 1H), 7.29-7.48 (m, 5H); MS m/z 348 [M+H]$^+$.

Example 48

(2S,5R)-6-(Benzyloxy)-2-((((1-phenylethylidene)amino)oxy)carbonyl)-1,6-diazabicyclo[3.2.1]octane-7-one

[Chemical Formula 89]

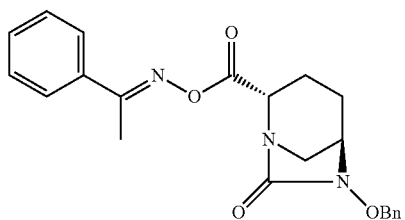

III-48

Step 1 tert-Butyl (2S,5R)-5-((benzyloxy)((trichloromethoxy)carbonyl)amino)-2-((((1-phenylethylidene)amino)oxy)carbonyl)piperidine-1-carboxylate or tert-butyl (2S,5R)-5-((benzyloxy)(chlorocarbonyl)amino)-2-((((1-phenylethylidene)amino)oxy)carbonyl)piperidine-1-carboxylate tert-Butyl (2S,5R)-5-((benzyloxy)amino)-2-((((1-phenylethylidene)amino)oxy) carbonyl)piperidine-1-carboxylate (Example 19, 1.434 g, 3.067 mmol) was dissolved in dehydrated dichloromethane (32 mL), and diisopropylethylamine (792 mg) was added, followed by ice cooling. To the mixture was added triphosgene (518 mg), followed by stirring for 15 minutes, and the completion of the reaction for the title compounds was confirmed by TLC. The compounds were subjected to the next step without purification and isolation.

Step 2

Trichloromethyl benzyloxy ((3R,6S)-6-((((1-phenylethylidene)amino)oxy) carbonyl)piperidin-3-yl)carbamate or (benzyloxy)((3R,6S)-6-((((1-phenylethylidene) amino)oxy)carbonyl)piperidin-3-yl) carbamoyl chloride, methanesulfonate To the mixture in Step 1 above was added methanesulfonic acid (2.95 g) under ice cooling, followed by stirring for 30 minutes, and the completion of the reaction for the title compounds was confirmed by TLC. The compounds were subjected to the next step without purification and isolation.

Step 3

(2S,5R)-6-(Benzyloxy)-2-((((1-phenylethylidene)amino)oxy)carbonyl)-1,6-diazabicyclo[3.2.1]octane-7-one The mixture in Step 2 above was added dropwise to ice-cold 1 M potassium bicarbonate (33 mL), followed by stirring for 1 hour. The reaction solvent was diluted with ethyl acetate (100 mL), washed sequentially with 0.1 M hydrochloric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 66 mg of the title compound (total yield over three steps: 6%).

$^1$H NMR (400 MHz, CDCl$_3$) δ 1.81 (m, 1H), 2.03-2.22 (m, 2H), 2.38 (m, 1H), 2.41 (s, 3H),3.09 (m, 1H), 3.16 (m, 1H), 3.25 (br.s., 1H), 4.33 (m, 1H), 4.93 (d, J=11.4 Hz, 1H), 5.08 (d, J=11.5 Hz, 1H), 7.32-7.49 (m, 8H), 7.75 (m, 2H); MS m/z 394 [M+H]$^+$.

Example 49

1,3-Dioxo-1,3-dihydro-2H-isoindol-2-yl (2S,5R)-6-(benzyloxy)-7-oxo-1,6-diazabicyclo[3.2.1]octane-2-carboxylate

[Chemical Formula 90]

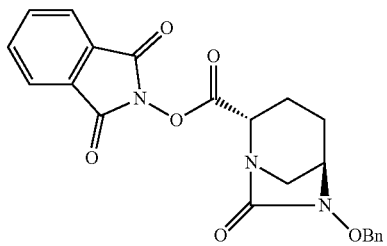

III-49

Step 1

1-tert-Butyl 2-(1,3-dioxo-1,3-dihydro-2H-isoindol-2-yl) (2S,5R)-5-((benzyloxy)((trichloromethoxy)carbonyl)amino)piperidine-1,2-dicarboxylate or 1-tert-butyl 2-(1,3-dioxo-1,3-dihydro-2H-isoindol-2-yl) (2S,5R)-5-((benzyloxy) (chlorocarbonyl)amino) piperidine-1,2-dicarboxylate 1-tert-Butyl 2-(1,3-dioxo-1,3-dihydro-2H-isoindol-2-yl) (2S,5R)-5-((benzyloxy)amino)piperidine-1,2-dicarboxylate (Example 20, 495 mg, 1 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

1,3-Dioxo-1,3-dihydro-2H-isoindol-2-yl (2S,5R)-5-((benzyloxy) ((trichloromethoxy)carbonyl)amino) piperidine-2-carboxylate or 1,3-dioxo-1,3-dihydro-2H-isoindol-2-yl (2S,5R)-5-((benzyloxy) (chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

1,3-Dioxo-1,3-dihydro-2H-isoindol-2-yl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/1) to afford 374 mg of the title compound (total yield over three steps: 89%).

$^1$H NMR (400 MHz, CDCl$_3$) δ 1.75-1.79 (m, 1H), 2.09-2.29 (m, 3H), 3.20 (m, 2H), 3.38 (br. s., 1H), 4.54 (d, J=6.9 Hz, 1H), 5.00 (d, J=11.4 Hz, 1H), 5.08 (d, J=11.4 Hz, 1H), 7.34-7.46 (m, 5H), 7.77-7.85 (m, 2H), 7.85-7.93 (m, 2H); MS m/z 422 [M+H]$^+$.

Example 50

S-Dodecyl (2S,5R)-6-(benzyloxy)-7-oxo-1,6-diazabicyclo[3.2.1]octane-2-carbothioate

[Chemical Formula 91]

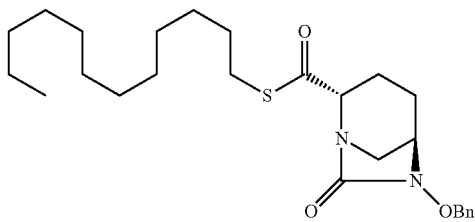

III-50

Step 1 tert-Butyl (2S,5R)-5-((benzyloxy)((trichloromethoxy)carbonyl)amino)-2-((dodecylthio)carbonyl)piperidine-1-carboxylate or tert-butyl (2S,5R)-5-((benzyloxy)(chlorocarbonyl)amino)-2-((dodecylthio)carbonyl)piperidine-1-carboxylate tert-Butyl (2S,5R)-5-((benzyloxy)amino)-2-((dodecylthio)carbonyl) piperidine-1-carboxylate (Example 23, 104 mg, 0.194 mmol) was dissolved in dehydrated dichloromethane (8 mL), and diisopropylethylamine (50.2 mg) was added, followed by ice cooling. To the mixture was added triphosgene (33 mg), followed by stirring for 40 minutes, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-((dodecylthio) carbonyl)piperidine or (2S,5R)-5-((benzyloxy)(chlorocarbonyl)amino)-2-((dodecylthio)carbonyl)piperidine, methanesulfonate To the mixture in Step 1 above was added methanesulfonic acid (186 mg) under ice cooling, followed by stirring for 20 minutes, and the completion of the reaction for the title compounds was confirmed by TLC. The compounds were subjected to the next step without purification and isolation.

Step 3

S-Dodecyl (2S,5R)-6-(benzyloxy)-7-oxo-1,6-diazabicyclo[3.2.1]octane-2-carbothioate The mixture in Step 2 above was added dropwise to ice-cold 1 M potassium bicarbonate (2 mL), followed by stirring for 0.7 hours. The reaction solvent was diluted with ethyl acetate (100 mL), washed sequentially with 0.1 M hydrochloric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 33.4 mg of the title compound as an oil (total yield over three steps: 37%).

$^1$H NMR (400 MHz, CDCl$_3$) δ 0.82-0.97 (m, 5H), 1.21-1.33 (m, 15H), 1.50-1.62 (m, 4H), 2.00 (m, 2H), 2.21 (m, 1H), 2.79 (d, J=11.9 Hz, 1H), 2.88 (m, 2H), 3.07 (d, J=11.9 Hz, 1H), 3.29 (br.s., 1H), 4.06 (m, 1H), 4.91 (d, J=11.5 Hz, 1H), 5.05 (d, J=11.4 Hz, 1H), 7.33-7.44 (m, 5H); MS m/z 461 [M+H]$^+$.

Example 51

S-(4-tert-Butylphenyl) (2S,5R)-6-(benzyloxy)-7-oxo-1,6-diazabicyclo[3.2.1] octane-2-carbothioate

[Chemical Formula 92]

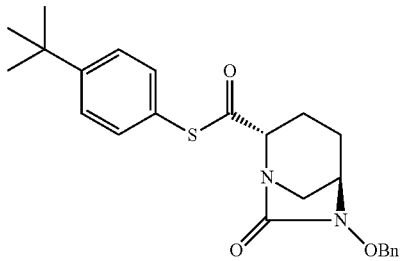

III-51

Step 1 tert-Butyl (2S,5R)-5-((benzyloxy)((trichloromethoxy)carbonyl)amino)-2-(((4-tert-butylphenyl)thio)carbonyl)piperidine-1-carboxylate or tert-butyl (2S,5R)-5-((benzyloxy)(chlorocarbonyl)amino)-2-(((4-tert-butylphenylthio)carbonyl)piperidine-1-carboxylate tert-Butyl (2S,5R)-5-((benzyloxy)amino)-2-4(4-(tert-butylphenyl)thio) carbonyl)piperidine-1-carboxylate (Example 24, 194 mg, 0.389 mmol) was dissolved in dehydrated dichloromethane (8 mL), and diisopropylethylamine (100 mg) was added, followed by ice cooling. To the mixture was added triphosgene (65.8 mg), followed by stirring for 45 minutes, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-4(4-tert-butylphenyl)thio)carbonyl) piperidine or (2S,5R)-5-((benzyloxy)(chlorocarbonyl) amino)-2-(((4-(tert-butyl)phenyl)thio)carbonyl) piperidine, methanesulfonate To the mixture in Step 1 above was added methanesulfonic acid (373 mg) under ice cooling, followed by stirring for 30 minutes, and the completion of the reaction for the title compounds was confirmed by TLC. The compounds were subjected to the next step without purification and isolation.

Step 3

S-(4-tert-Butylphenyl) (2S,5R)-6-(benzyloxy)-7-oxo-1,6-diazabicyclo[3.2.1] octane-2-carbothioate The mixture in Step 2 above was added dropwise to 1 M potassium bicarbonate (4.2 mL), followed by stirring for 1 hour. The reaction solvent was diluted with ethyl acetate (100 mL), washed sequentially with 0.1 M hydrochloric acid (100 mL), saturated sodium bicarbonate (100 mL) and saturated brine (100 mL), dried over anhydrous magnesium sulfate, filtered, and concentrated under reduced pressure. The solid in the residue was washed with hexane/ethyl acetate (3/1, 8 mL) and hexane (2×8 mL) and dried in vacuo to afford 68 mg of the title compound (total yield over three steps: 41%).
$^1$H NMR (400 MHz, CDCl$_3$) δ 1.32 (s, 9H), 1.54 (m, 1H), 2.01 (m, 2H), 2.18-2.28 (m, 1H), 2.90 (d, J=12.0 Hz, 1H), 3.17 (d, J=11.7 Hz, 1H), 3.32 (br.s., 1H), 4.21 (d, J=6.9 Hz, 1H), 4.93 (d, J=11.5 Hz, 1H), 5.07 (d, J=11.5 Hz, 1H), 7.31-7.46 (m, 9H); MS m/z 425 [M+H]$^+$.

Example 52

S-(4-Nitrophenyl) (2S,5R)-6-(benzyloxy)-7-oxo-1,6-diazabicyclo[3.2.1]octane-2-carbothioate

[Chemical Formula 93]

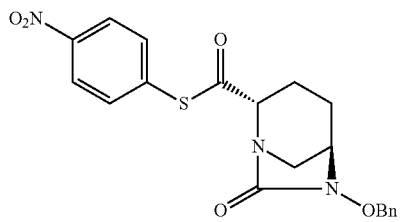

III-52

Step 1 tert-Butyl (2S,5R)-5-((benzyloxy)((trichloromethoxy)carbonyl)amino)-2-(((4-nitrophenyl)thio)carbonyl)piperidine-1-carboxylate or tert-butyl (2S,5R)-5-((benzyloxy)(chlorocarbonyl)amino)-2-(((4-nitrophenyl)thio)carbonyl)piperidine-1-carboxylate tert-Butyl (2S,5R)-5-((benzyloxy)amino)-2-(((4-nitrophenyl)thio)carbonyl) piperidine-1-carboxylate (Example 25, 371 mg, 0.76 mmol) was dissolved in dehydrated dichloromethane (8 mL), and diisopropylethylamine (196 mg) was added, followed by ice cooling. To the mixture was added triphosgene (128 mg), followed by stirring for 20 minutes, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-(((4-nitrophenyl) thio)carbonyl)piperidine or (2S,5R)-5-((benzyloxy)(chlorocarbonyl) amino)-2-(((4-nitrophenyl)thio)carbonyl)piperidine, methanesulfonate To the mixture in Step 1 above was added methanesulfonic acid (730 mg) under ice cooling, followed by stirring for 25 minutes, and the completion of the reaction for the title compounds was confirmed by TLC. The compounds were subjected to the next step without purification and isolation.

Step 3

S-(4-Nitrophenyl) (2S,5R)-6-(benzyloxy)-7-oxo-1,6-diazabicyclo[3.2.1] octane-2-carbothioate The mixture in Step 2 above was added dropwise to 1 M potassium bicarbonate (8 mL), followed by stirring for 2 hours. The reaction solvent was diluted with ethyl acetate (100 mL), washed sequentially with 0.1 M hydrochloric acid (100 mL), saturated sodium bicarbonate (100 mL) and saturated brine (100 mL), dried over anhydrous magnesium sulfate, filtered, and concentrated under reduced pressure. The residue was subjected to silica gel column chromatography (hexane/ethyl acetate=1/1). The solid in the residue was washed with hexane/ethyl acetate (5/1, 2×6 mL) and dried in vacuo to afford 87.3 mg of the title compound as a yellow crystalline powder (total yield over three steps: 28%).
$^1$H NMR (400 MHz, CDCl$_3$) δ 1.58 (m, 1H), 2.07 (m, 2H), 2.19-2.34 (m, 1H), 2.87 (d, J=11.9 Hz, 1H), 3.23 (d, J=11.9 Hz, 1H), 3.36-3.48 (br.s., 1H), 4.25 (d, J=6.4 Hz, 1H), 4.95 (d, J=11.4 Hz, 1H), 5.09 (d, J=11.5 Hz, 1H), 7.37-7.49 (m, 5H), 7.65 (d, J=8.8 Hz, 2H), 8.24 (d, J=8.8 Hz, 2H); MS m/z 414 [M+H]$^+$.

Example 53

S-(Pyridine-2-yl) (2S,5R)-6-(benzyloxy)-7-oxo-1,6-diazabicyclo[3.2.1]octane-2-carbothioate

[Chemical Formula 94]

III-53

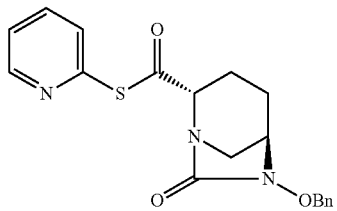

Step 1 tert-Butyl (2S,5R)-5-((benzyloxy)((trichloromethoxy)carbonyl)amino)-2-(((pyridine-2-yl)thio)carbonyl)piperidine-1-carboxylate or tert-butyl (2S,5R)-5-((benzyloxy)(chlorocarbonyl)amino)-2-(((pyridine-2-yl)thio)carbonyl)piperidine-1-carboxylate tert-Butyl (2S,5R)-5-((benzyloxy)amino)-2-(((pyridine-2-yl)thio)carbonyl) piperidine-1-carboxylate (Example 26, 886 mg, 2.0 mmol) was dissolved in dehydrated dichloromethane (16 mL), and diisopropylethylamine (516 mg) was added, followed by ice cooling. To the mixture was added triphosgene (338 mg), followed by stirring for 15 minutes, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-(((pyridine-2-yl) thio)carbonyl)piperidine or (2S,5R)-5-((benzyloxy)(chlorocarbonyl)amino)-2-(((pyridine-2-yl)thio)carbonyl)piperidine, methanesulfonate To the mixture in Step 1 above was added methanesulfonic acid (1922 mg) under ice cooling, followed by stirring for 30 minutes, and the completion of the reaction for the title compounds was confirmed by TLC. The compounds were subjected to the next step without purification and isolation.

Step 3

S-(Pyridine-2-yl) (2S,5R)-6-(benzyloxy)-7-oxo-1,6-diazabicyclo[3.2.1]octane-2-carbothioate The mixture in Step 2 above was added dropwise to ice-cold 1 M potassium bicarbonate (16 mL), followed by stirring for 1 hour. The reaction solvent was diluted with ethyl acetate (100 mL), washed sequentially with 0.1 M hydrochloric acid (100 mL), saturated sodium bicarbonate (100 mL) and saturated brine (100 mL), dried over anhydrous magnesium sulfate and filtered, and the solvent was distilled off under reduced pressure. The residue was subjected to silica gel column chromatography (hexane/ethyl acetate=1/1) to afford 84 mg of the title compound (total yield over three steps: 11%).

$^1$H NMR (400 MHz, CDCl$_3$) δ 1.56 (m, 1H), 2.02 (m, 2H), 2.18-2.28 (m, 1H), 2.94 (d, J=12.0 Hz, 1H), 3.20 (m, 1H), 3.34 (br.s., 1H), 4.21 (m, 1H), 4.92 (d, J=11.5 Hz, 1H), 5.07 (d, J=11.5 Hz, 1H), 7.30-7.46 (m, 6H), 7.50 (m, 1H), 7.56 (td, J=7.9 & 0.9 Hz, 1H), 8.66 (m, 1H); MS m/z 370 [M+H]$^+$.

Example 54

S-(5-Nitropyridine-2-yl) (2S,5R)-6-(benzyloxy)-7-oxo-1,6-diazabicyclo[3.2.1] octane-2-carbothioate

[Chemical Formula 95]

III-54

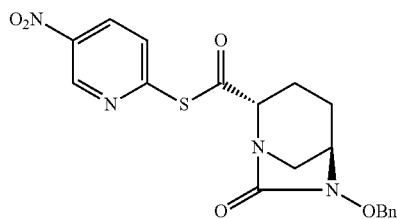

Step 1 tert-Butyl (2S,5R)-5-((benzyloxy)((trichloromethoxy)carbonyl)amino)-2-(((5-nitropyridine-2-yl)thio)carbonyl)piperidine-1-carboxylate or tert-butyl (2S,5R)-5-((benzyloxy)(chlorocarbonyl)amino)-2-(((5-nitropyridine-2-yl)thio)carbonyl)piperidine-1-carboxylate tert-Butyl (2S,5R)-5-((benzyloxy)amino)-2-(((5-nitropyridine-2-yl)thio) carbonyl)piperidine-1-carboxylate (Example 27, 2.31 g, 4.72 mmol) was dissolved in dehydrated dichloromethane (32 mL), and diisopropylethylamine (1.22 g) was added, followed by ice cooling. To the mixture was added triphosgene (803 mg), followed by stirring for 15 minutes, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-(((5-nitropyridine-2-yl)thio)carbonyl) piperidine or (2S,5R)-5-((benzyloxy)(chlorocarbonyl) amino)-2-(((5-nitropyridine-2-yl)thio)carbonyl) piperidine, methanesulfonate To the mixture in Step 1 above was added methanesulfonic acid (4.53 g) under ice cooling, followed by stirring for 30 minutes, and the completion of the reaction for the title compounds was confirmed by TLC. The compounds were subjected to the next step without purification and isolation.

Step 3

S-(5-Nitropyridine-2-yl) (2S,5R)-6-(benzyloxy)-7-oxo-1,6-diazabicyclo[3.2.1] octane-2-carbothioate The mixture in Step 2 above was added dropwise to ice-cold 1 M potassium bicarbonate (52 mL), followed by stirring for 1 hour. The reaction solvent was diluted with ethyl acetate (300 mL), washed sequentially with 0.1 M hydrochloric acid (300 mL), saturated sodium bicarbonate (300 mL) and saturated brine (300 mL), dried over anhydrous magnesium sulfate and filtered, and the solvent was distilled off under reduced pressure. The residue was subjected to silica gel column chromatography (hexane/ethyl acetate=1/1) to afford 34.8 mg of the title compound (total yield over three steps: 2%).

$^1$H NMR (400 MHz, CDCl$_3$) δ 1.50-1.69 (m, 1H), 2.00-2.12 (m, 2H), 2.19-2.31 (m, 1H), 2.87 (d, J=11.9 Hz, 1H), 3.22 (d, J=11.9 Hz, 1H), 3.36-3.40 (m, 1H), 4.27 (d, J=5.9 Hz, 1H), 4.93 (d, J=11.5 Hz, 1H), 5.07 (d, J=11.4 Hz, 1H), 7.36-7.47 (m, 5H), 7.86 (dd, J=8.7, 0.6 Hz, 1H), 8.50 (dd, J=8.6 & 2.8 Hz, 1H), 9.41 (dd, J=2.7 & 0.6 Hz, 1H); MS m/z 415 [M+H]$^+$.

Example 55

(2S,5R)-6-(Benzyloxy)-2-[(2-thioxo-1,3-thiazolidine-3-yl)carbonyl]-1,6-diazabicyclo[3.2.1]octane-7-one

[Chemical Formula 96]

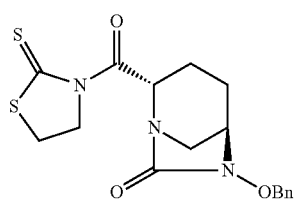

III-55

Step 1 tert-Butyl (2S,5R)-5-((benzyloxy)((trichloromethoxy)carbonyl)amino)-2-((2-thioxo-1,3-thiazolidine-3-yl)carbonyl)piperidine-1-carboxylate or tert-butyl (2S,5R)-5-((benzyloxy)(chlorocarbonyl)amino)-2-((2-thioxo-1,3-thiazolidine-3-yl)carbonyl) piperidine-1-carboxylate tert-Butyl (2S,5R)-5-((benzyloxy)amino)-2-((2-thioxo-1,3-thiazolidine-3-yl) carbonyl)piperidine-1-carboxylate (Example 28, 444 mg, 0.98 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC. The compounds were subjected to the next step without purification and isolation.

Step 2

(2S,5R)-5-((Benzyloxy)(trichloromethoxy)carbonyl)amino)-2-((2-thioxo-1,3-thiazolidine-3-yl)carbonyl)piperidine or (2S,5R)-5-((benzyloxy)(chlorocarbonyl) amino)-2-((2-thioxo-1,3-thiazolidine-3-yl) carbonyl)piperidine, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

(2S,5R)-6-(Benzyloxy)-2-[(2-thioxo-1,3-thiazolidine-3-yl)carbonyl]-1,6-diazabicyclo[3.2.1]octane-7-one The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/1) to afford 167 mg of the title compound (total yield over three steps: 45%).

$^1$H NMR (400 MHz, CDCl$_3$) δ 1.72-1.88 (m, 1H), 2.00-2.18 (m, 3H), 3.19-3.41 (m, 5H), 4.56 (ddd, J=11.7 & 7.4 & 5.4 Hz, 1H), 4.70 (ddd, J=11.7 & 9.1 & 7.4 Hz, 1H), 4.90 (d, J=11.4 Hz, 1H), 5.03 (d, J=11.4 Hz, 1H), 5.30 (m, 1H), 7.31-7.49 (m, 5H); MS m/z 378 [M+H]$^+$.

Example 56

(2S,5R)-6-(Benzyloxy)-2-[(2-thioxo-1,3-oxazolidine-3-yl)carbonyl]-1,6-diazabicyclo[3.2.1]octane-7-one

[Chemical Formula 97]

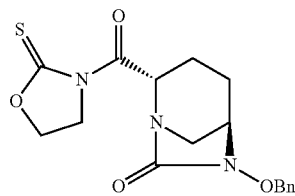

III-56

Step 1 tert-Butyl (2S,5R)-5-((benzyloxy)((trichloromethoxy)carbonyl)amino)-2-((2-thioxo-1,3-oxazolidine-3-yl)carbonyl)piperidine-1-carboxylate or tert-butyl (2S,5R)-5-((benzyloxy)(chlorocarbonyl) amino)-2-((2-thioxo-1,3-oxazolidine-3-yl)carbonyl) piperidine-1-carboxylate tert-Butyl (2S,5R)-5-((benzyloxy)amino)-2-((2-thioxo-1,3-oxazolidine-3-yl) carbonyl)piperidine-1-carboxylate (Example 29, 330 mg, 0.76 mmol) was dissolved in dehydrated dichloromethane (6 mL), and diisopropylethylamine (196 mg) was added, followed by ice cooling. To the mixture was added triphosgene (135 mg), followed by stirring for 0.5 hours, and the completion of the reaction for the title compounds was confirmed by TLC. The compounds were subjected to the next step without purification and isolation.

Step 2

(2S,5R)-5-((Benzyloxy)((trichloromethoxy)carbonyl)amino)-2-((2-thioxo-1,3-oxazolidine-3-yl)carbonyl)piperidine or (2S,5R)-5-((benzyloxy)(chlorocarbonyl) amino)-2-((2-thioxo-1,3-oxazolidine-3-yl)carbonyl)piperidine, methanesulfonate To the mixture in Step 1 above was added methanesulfonic acid (0.50 mL) under ice cooling, followed by stirring for 5 minutes, and the completion of the reaction for the title compounds was confirmed by TLC. The compounds were subjected to the next step without purification and isolation.

Step 3

(2S,5R)-6-(Benzyloxy)-2-[(2-thioxo-1,3-oxazolidine-3-yl)carbonyl]-1,6-diazabicyclo[3.2.1]octane-7-one The mixture in Step 2 above was added dropwise to ice-cold 1 M potassium bicarbonate (0.83 g/7 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The residue was subjected to silica gel column chromatography (hexane/ethyl acetate=1/1) to afford 116 mg of the title compound (total yield over three steps: 42%).
$^1$H NMR (400 MHz, CDCl$_3$) δ 1.72-1.88 (m, 1H), 2.00-2.18 (m, 3H), 3.19-3.41 (m, 5H), 4.56 (ddd, J=11.7 & 7.4 & 5.4 Hz, 1H), 4.70 (ddd, J=11.7 & 9.1 & 7.4 Hz, 1H), 4.90 (d, J=11.4 Hz, 1H), 5.03 (d, J=11.4 Hz, 1H), 5.30 (m, 1H), 7.31-7.49 (m, 5H); MS m/z 362 [M+H]$^+$.

Example 57a 2,5-Dioxopyrrolidin-1-yl (2S,5R)-6-(benzyloxy)-7-oxo-1,6-diazabicyclo[3.2.1] octane-2-carboxylate (III-57)

[Chemical Formula 98]

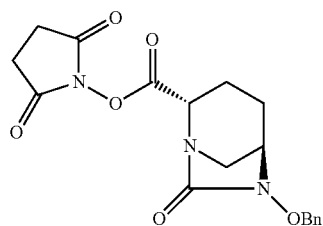

III-57

Step 1

1-tert-Butyl 2-(2,5-dioxopyrrolidin-1-yl) (2S,5R)-5-((benzyloxy) ((trichloromethoxy)carbonyl)amino) piperidine-1,2-dicarboxylate or 1-tert-butyl 2-(2,5-dioxopyrrolidin-1-yl) (2S,5R)-5-((benzyloxy) (chlorocarbonyl)amino) piperidine-1,2-dicarboxylate tert-Butyl 2-(2,5-dioxopyrrolidin-1-yl) (2S,5R)-5-((benzyloxy)amino) piperidine-1,2-dicarboxylate (Example 30, 447 mg, 1 mmol) was dissolved in dehydrated dichloromethane (8 mL), and diisopropylethylamine (259 mg) was added, followed by ice cooling. To the mixture was added triphosgene (169 mg), followed by stirring for 1.5 hours, and the completion of the reaction for the title compounds was confirmed by TLC. The compounds were subjected to the next step without purification and isolation.

Step 2

2,5-Dioxopyrrolidine-1-yl (2S,5R)-5-((benzyloxy) ((trichloromethoxy) carbonyl)amino)piperidine-2-carboxylate or 2,5-dioxopyrrolidine-1-yl (2S,5R)-5-((benzyloxy)(chlorocarbonyl)amino)piperidine-2-carboxylate, methanesulfonate To the mixture in Step 1 above was added methanesulfonic acid (961 mg) under ice cooling, followed by stirring for 5 minutes, and the completion of the reaction for the title compounds was confirmed by TLC. The compounds were subjected to the next step without purification and isolation.

Step 3

2,5-Dioxopyrrolidine-1-yl (2S,5R)-6-(benzyloxy)-7-oxo-1,6-diazabicyclo [3.2.1]octane-2-carboxylate To the mixture in Step 2 above was added dropwise diisopropylethylamine (1.43 g), followed by stirring for 0.5 hours. The reaction solvent was concentrated under reduced pressure. The residue was diluted with ethyl acetate (65 mL), washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed sequentially with hexane/ethyl acetate (1/1, 2 mL), hexane/ethyl acetate (2/1, 2 mL) and hexane (2 mL) and dried in vacuo to afford 274 mg of the title compound as a colorless crystalline powder (total yield over three steps: 73%). Instrumental data were consistent with those of Reference Example 18.

Example 57b 2,5-Dioxopyrrolidine-1-yl (2S,5R)-6-(benzyloxy)-7-oxo-1,6-diazabicyclo [3.2.1]octane-2-carboxylate (III-57) Sequential synthesis 1

(2S,5R)-5-((Benzyloxy)amino)-1-(tert-butoxycarbonyl) piperidine-2-carboxylic acid (Reference Example 4, 354 mg, 1 mmol) was dissolved in dehydrated acetonitrile (8 mL), and diisopropylethylamine (194 mg) and 4-dimethylaminopyridine (12 mg) were added, followed by ice cooling. To the mixture was added bis (2,5-dioxopyrrolidine-1-yl) carbonate (384 mg), followed by stirring at room temperature for 3 hours. The residue resulted from concentration of the reaction solution under reduced pressure was diluted with ethyl acetate (65 mL), washed with 10% citric acid (20 mL), and subsequently stirred with saturated sodium bicarbonate (20 mL) for 15 minutes. The organic layer was separated, washed with saturated brine (20 mL), dried over anhydrous magnesium sulfate and filtered. The solvent was distilled off under reduced pressure to give 436 mg of the residue (step yield 98%). The total amount of the residue was dissolved in dehydrated dichloromethane (8 mL), and diisopropylethylamine (259 mg) was added, followed by ice cooling. To the mixture was added triphosgene (169 mg), followed by stirring for 1 hour. Methanesulfonic acid (961 mg) was then added, followed by stirring for 5 minutes. The mixture was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed sequentially with hexane/ethyl acetate (1/1, 2 mL), hexane/ethyl acetate (2/1, 2 mL) and hexane (2 mL) to afford 260 mg of the title compound as crystalline solid (total yield 58%). Instrumental data were consistent with those of Reference Example 18.

Example 57c 2,5-Dioxopyrrolidine-1-yl (2S,5R)-6-(benzyloxy)-7-oxo-1,6-diazabicyclo [3.2.1]octane-2-carboxylate (III-57) Sequential synthesis 2

(2S,5R)-5-((Benzyloxy)amino)-1-(tert-butoxycarbonyl) piperidine-2-carboxylic acid (Reference Example 4, 700 mg, 2 mmol) was dissolved in dehydrated tetrahydrofuran (10 mL), followed by cooling to −20° C. To the mixture were sequentially added dropwise isobutyl chloroformate (300 mg) and triethylamine (444 mg), followed by stirring for 15 minutes. To the reaction solution was added 1-hydroxypyrrolidine-2,5-dione (253 mg), followed by stirring for 30 minutes and stirring for another 30 minutes at room temperature. The reaction solution was diluted with ethyl acetate (35 mL), washed sequentially with 10% citric acid (10 mL), saturated sodium bicarbonate (10 mL) and saturated brine (10 mL), dried over anhydrous magnesium sulfate and filtered, and the solvent was distilled off under reduced pressure to give 985 mg of the residue. The total amount of the residue was dissolved in dehydrated chloroform (10 mL), and triethylamine (303 mg) was added, followed by ice cooling. To the mixture was added triphosgene (237 mg), followed by stirring for 30 minutes. Methanol (0.1 mL) was added, followed by stirring for 30 minutes. A solution of methanesulfonic acid (1.3 mL) in dichloromethane (4.0 mL) was then added dropwise, followed by further stirring for 30 minutes. The mixture was added dropwise to ice-cold 1 M potassium bicarbonate (2.4 g/20 mL), followed by stirring for 30 minutes. Chloroform (10 mL) was added and the layers were separated. The organic layer was washed sequentially with 1 M hydrochloric acid (10 mL), saturated sodium bicarbonate (10 mL) and saturated brine (10 mL). The organic layer was dried over anhydrous magnesium sulfate, filtered and concentrated under reduced pressure. Seeding was carried out to the residue, and to the solid was added hexane/ethyl acetate (1/2, 3 mL), stirred, filtered, washed sequentially with hexane/ethyl acetate (1/1, 3 mL) and hexane (3 mL) to afford 556 mg of the title compound as crystals (total yield 75%). Instrumental data were consistent with those of Reference Example 18.

Example 58a (1R,2S,6R,7S)-3,5-Dioxo-4-azatricyclo[5.2.1.0$^{2,6}$] dec-8-en-4-yl (2S,5R)-6-(benzyloxy)-7-oxo-1,6-diazabicyclo[3.2.1]octane-2-carboxylate (III-58)

[Chemical Formula 99]

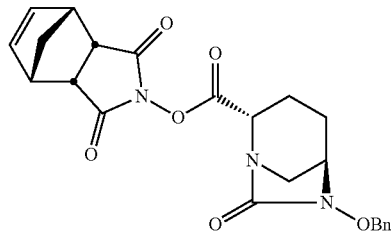

III-58

Step 1

1-tert-Butyl 2-((1R,2S,6R,7S)-3,5-dioxo-4-azatricyclo[5.2.1.0$^{2,6}$]dec-8-en-4-yl) (2S,5R)-5-((benzyloxy) ((trichloromethoxy)carbonyl)amino)piperidine-1,2-dicarboxylate or 1-tert-butyl 2-((1R,2S,6R,7S)-3,5-dioxo-4-azatricyclo[5.2.1.0$^{2,6}$]dec-8-en-4-yl) (2S,5R)-5-((benzyloxy)(chlorocarbonyl)amino) piperidine-1,2-dicarboxylate 1-tert-Butyl 2-((1R,2S,6R,7S)-3,5-dioxo-4-azatricyclo [5.2.1.0$^{2,6}$]dec-8-en-4-yl) (2S,5R)-5-((benzyloxy)amino)piperidine-1,2-dicarboxylate (Example 31, 512 mg, 1 mmol) was dissolved in dehydrated dichloromethane (8 mL), and diisopropylethylamine (260 mg) was added, followed by ice cooling. To the mixture was added triphosgene (169 mg), followed by stirring for 0.5 hours, and the completion of the reaction for the title compounds was confirmed by TLC (MS m/z 575 [M+H]$^+$). The compounds were subjected to the next step without purification and isolation.

Step 2

(1R,2S,6R,7S)-3,5-Dioxo-4-azatricyclo[5.2.1.0$^{2,6}$] dec-8-en-4-yl (2S,5R)-5-((benzyloxy)((trichloromethoxy)carbonyl)amino)piperidine-2-carboxylate or (1R,2S,6R,7S)-3,5-dioxo-4-azatricyclo[5.2.1.0$^{2,6}$] dec-8-en-4-yl (2S,5R)-5-((benzyloxy)(chlorocarbonyl)amino)piperidine-2-carboxylate, methanesulfonate To the mixture in Step 1 above was added methanesulfonic acid (0.65 mL) under ice cooling, followed by stirring for 5 minutes, and the completion of the reaction for the title compounds was confirmed by TLC. The compounds were subjected to the next step without purification and isolation.

Step 3

(1R,2S,6R,7S)-3,5-Dioxo-4-azatricyclo[5.2.1.0$^{2,6}$] dec-8-en-4-yl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (1.1 g/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, filtered, and concentrated under reduced pressure. The solid in the residue was washed with ethyl acetate/hexane (1:2) and dried to afford 346 mg of the title compound as a colorless crystalline powder (total yield over three steps: 79%). Instrumental data were consistent with those of Reference Example 19.

Example 58b (1R,2S,6R,7S)-3,5-Dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate (III-58) Sequential synthesis 1

(2S,5R)-5-((Benzyloxy)amino)-1-(tert-butoxycarbonyl)piperidine-2-carboxylic acid (Reference Example 4, 368 mg, 1.05 mmol) was dissolved in dehydrated dichloromethane (4 mL), and (1R,2S,6R,7S)-4-hydroxy-4-azatricyclo[5.2.1.0$^{2,6}$] dec-8-ene-3,5-dione (207 mg) was added, followed by ice cooling. To the mixture were sequentially added 1-ethyl-3-(3-dimethylaminopropyl)carbodiimide hydrochloride (221 mg) and 4-dimethylaminopyridine (13 mg), followed by stirring at room temperature overnight. The residue resulted from concentration of the reaction solution under reduced pressure was diluted with ethyl acetate (30 mL), washed sequentially with ice-cold 10% citric acid (10 mL), saturated sodium bicarbonate (10 mL) and saturated brine (10 mL), dried over anhydrous magnesium sulfate, and filtered. The total amount of the residue 541 mg obtained by distilling off the solvent under reduced pressure was dissolved in dehydrated dichloromethane (8 mL), and diisopropylethylamine (155 mg) was added, followed by ice cooling. To the mixture was added triphosgene (119 mg), followed by stirring for 0.5 hours. Methanesulfonic acid (0.52 mL) was then added, followed by stirring for 5 minutes. The mixture was added dropwise to ice-cold 1 M potassium bicarbonate (801 mg/9 mL), followed by stirring for 0.5 hours. Ethyl acetate (65 mL) was added and the layers were separated. The organic layer was washed sequentially with 1 M hydrochloric acid (20 mL), saturated sodium bicarbonate (20 mL) and saturated brine (20 mL), dried over anhydrous magnesium sulfate, and filtered. The solid in the residue resulted from concentration of the solvent under reduced pressure was washed with hexane/ethyl acetate (1/3), filtered and dried to afford 346 mg of the title compound (total yield 75%). Instrumental data were consistent with those of Reference Example 19.

Example 58c (1R,2S,6R,7S)-3,5-Dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate (III-58) Sequential synthesis 2

(2S,5R)-5-((Benzyloxy)amino)-1-(tert-butoxycarbonyl)piperidine-2-carboxylic acid (Reference Example 4, 14.0 g, 41.09 mmol) was dissolved in dehydrated tetrahydrofuran (200 mL), followed by cooling to around −20° C. To the mixture were added dropwise isobutyl chloroformate (6.11 g) and then triethylamine (8.86 g), followed by stirring at the same temperature for 15 minutes. Then, to the reaction solution was added (1R,2S,6R,7S)-4-hydroxy-4-azatricyclo[5.2.1.0$^{2,6}$]dec-8-ene-3,5-dione (7.87 g), followed by stirring at the same temperature for 30 minutes and then at room temperature for 30 minutes. The reaction solution was diluted with ethyl acetate (700 mL), washed sequentially with ice-cold 10% citric acid (200 mL), saturated sodium bicarbonate (200 mL) and saturated brine (200 mL), dried over anhydrous magnesium sulfate, and filtered. The solvent was distilled off under reduced presssure, substitution-concentration was again carreid out with ethyl acetate, the total amount of the resulting residue 25.1 g (net yield 92%) was dissolved in dehydrated chloroform (180 mL), and triethylamine (5.5 g) was added, followed by ice cooling. To the mixture was added triphosgene (4.29 g), followed by stirring for 30 minutes. Methanol (1 mL) was then added, followed by stirring for 30 minutes. To the reaction solution was added dropwise a solution of methanesulfonic acid (23.5 mL) in dichloromethane (30 mL), followed by stirring for another 30 minutes. The mixture was added dropwise to ice-cold 1 M potassium bicarbonate (43.5 g/200 ml), followed by stirring for 30 minutes. Chloroform (100 ml) was added and the layers were separated. The organic layer was washed sequentially with 1 M hydrochloric acid (200 mL), saturated sodium bicarbonate (200 mL) and saturated brine (200 mL). Each aqueous layer was back-extracted with chloroform (100 mL) sequentially. The organic layers was combined, dried over anhydrous magnesium sulfate, and filtered. The residue obtained by concentration of the solvent under reduced pressure was dissolved in chloroform (70 mL), hexane (100 mL) was added, followed by stirring for 30 minutes for crystallization. Further, hexane (100 mL) was added for stirring and aging for 1 hour. The crystalline solid was filtered and dried to afford 15.4 g of the title compound (content 100%, total yield 88%). Instrumental data were consistent with those of Reference Example 19. As a result of evaluation of the stability of this product, it remained stable in a refrigerator for one month.

Example 59

1-tert-Butyl 2-43aR,7aS)-1,3-dioxo-3a,4,7,7a-tetrahydro-1H-isoindol-2(3H)-yl) (2S,5R)-5-((benzyloxy)amino)piperidine-1,2-dicarboxylate (II-32)

[Chemical Formula 100]

II-32

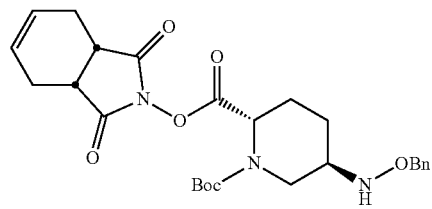

(2S,5R)-5-((Benzyloxy)amino)-1-(tert-butoxycarbonyl)piperidine-2-carboxylic acid (Reference Example 4, 3.504 g, 10 mmol) was dissolved in dehydrated tetrahydrofuran (50 mL), followed by cooling to around −20° C. To the mixture were added dropwise isobutyl chloroformate (1.51 g) and then triethylamine (2.17 g), followed by stirring at the same temperature for 15 minutes. Then, to the reaction solution was added (3aR,7aS)-2-hydroxy-3a,4,7,7a-tetrahydro-1H-isoindol-1,3(2H)-dione (Reference Example 20, 1.84 g), followed by stirring at the same temperature for 30 minutes and then at room temperature for 30 minutes. The reaction solution was diluted with ethyl acetate (200 mL), washed sequentially with ice-cold 10% citric acid (60 mL), saturated sodium bicarbonate (60 mL) and saturated brine (60 mL), dried over anhydrous magnesium sulfate, and filtered. The residue obtained by concentration of the filtrate under reduced pressure was subjected to silica gel column chromatography (hexane/ethyl acetate=2/1) to afford 4.689 g of the title compound as a colorless foamy solid (yield 94%).

$^1$H NMR (400 MHz, CDCl$_3$) δ 1.47 (bs, 9H), 1.59-1.75 (m, 2H), 2.04-2.32 (m, 2H), 2.16-2.35 (m, 2H), 2.61 (d, J=15.2 Hz, 2H), 3.14-3.24 (m, 4H), 4.15-4.22 (m, 1H), 4.71 (q, J=11.6 Hz, 2H), 5.03 (bs, 1H), 5.97 (bs, 2H), 7.26-7.38 (m, 5H); MS m/z 500 [M+H]$^+$.

Example 60a (3aR,7aS)-1,3-Dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate (III-59)

[Chemical Formula 101]

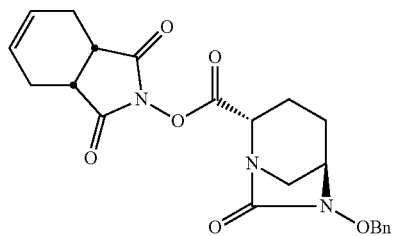

III-59

Step 1

1-tert-Butyl 2-((3aR,7aS)-1,3-dioxo-3a,4,7,7a-tetrahydro-1H-isoindol-2(3H)-yl) (2S,5R)-5-((benzyloxy)((trichloromethoxy)carbonyl)amino)piperidine-1,2-dicarboxylate or 1-tert-butyl 2-((3aR,7aS)-1,3-dioxo-3a,4,7,7a-tetrahydro-1H-isoindol-2(3H)-yl) (2S,5R)-5-((benzyloxy)(chlorocarbonyl)amino)piperidine-1,2-dicarboxylate 1-tert-Butyl 2-((3aR,7aS)-1,3-dioxo-3a,4,7,7a-tetrahydro-1H-isoindol-2(3H)-yl) (2S,5R)-5-((benzyloxy)amino)piperidine-1,2-dicarboxylate (Example 59, 4.689 g, 9.386 mmol) was dissolved in dehydrated chloroform (50 mL), and triethylamine (1.40 g) was added, followed by ice cooling. To the mixture was added triphosgene (1.09 g), followed by stirring for 0.5 hours, and the completion of the reaction for the title compounds was confirmed by TLC. The compounds were subjected to the next step without purification and isolation.

Step 2

(3aR,7aS)-1,3-Dioxo-3a,4,7,7a-tetrahydro-1H-isoindol-2(3H)-yl (2S,5R)-5-((benzyloxy)((trichloromethoxy)carbonyl)amino)piperidine-2-carboxylate or (3aR,7aS)-1,3-dioxo-3a,4,7,7a-tetrahydro-1H-isoindol-2(3H)-yl (2S,5R)-5-((benzyloxy) (chlorocarbonyl)amino)piperidine-2-carboxylate, methanesulfonate To the mixture in Step 1 above was added methanol (0.255 mL) under ice cooling, followed by stirring for 30 minutes. Subsequently, methanesulfonic acid (8.89 g) was added, followed by stirring for 30 minutes, and the completion of the reaction for the title compounds was confirmed by TLC. The compounds were subjected to the next step without purification and isolation.

Step 3

(3aR,7aS)-1,3-Dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (11.1 g/100 mL), followed by stirring for 0.5 hours. Chloroform (30 mL) was added, layers are separated, the organic layer was washed sequentially with 1 M hydrochloric acid (70 mL), saturated sodium bicarbonate (70 mL) and saturated brine (70 mL), dried over anhydrous magnesium sulfate, filtered, and concentrated under reduced pressure. The residue was dissolved in chloroform (16 mL), hexane (24 mL) was added, followed by stirring for 15 minutes. Further, hexane (8 mL) was added, followed by stirring and aging for 15 minutes. The precipitated solid was filtered, washed with a mixed solution of chloroform/hexane (2/3) and dried under reduced pressure to afford 3.51 g of the title compound as a colorless crystalline-powder (total yield over three steps: 88%). Instrumental data were consistent with those of Reference Example 21.

Example 60b (3aR,7aS)-1,3-Dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate (III-59) Sequential synthesis (2S,5R)-5-((Benzyloxy)amino)-1-(tert-butoxycarbonyl) piperidine-2-carboxylic acid (Reference Example 4, 3.504 g, 10 mmol) was dissolved in dehydrated tetrahydrofuran (50 mL), followed by cooling to around −20° C. To the mixture were added dropwise isobutyl chloroformate (1.157 g) and then triethylamine (2.17 g), followed by stirring at the same temperature for 15 minutes. Then, to the reaction solution was added (3aR,7aS)-2-hydroxy-3a,4,7,7a-tetrahydro-1H-isoindol-1,3(2H)-dione (Reference Example 20, 1.84 g), followed by stirring at the same temperature for 30 minutes and then at room temperature for 30 minutes. The reaction solution was diluted with ethyl acetate (200 mL), washed sequentially with ice-cold 10% citric acid (60 mL), saturated sodium bicarbonate (60 mL) and saturated brine (60 mL), dried over anhydrous magnesium sulfate, and filtered. The total amount of the residue 5.21 g (quantitative) obtained by concentration of the filtrate under reduced pressure was dissolved in dehydrated chloroform (50 mL), and triethylamine (1.5 g) was added, followed by ice cooling. To the mixture was added triphosgene (1.157 g), followed by stirring for 30 minutes. Methanol (0.27 mL) was then added, followed by stirring for 30 minutes. To the reaction solution was added dropwise a solution of methanesulfonic acid (9.47 g) in dichloromethane (8 mL), followed by stirring for another 30 minutes. The mixture was added dropwise to ice-cold 1 M potassium bicarbonate (11.84 g/100 ml), followed by stirring for 30 minutes. Chloroform (30 ml) was added and the layers were separated. The organic layer was washed sequentially with 1 M hydrochloric acid (70 mL), saturated sodium bicarbonate (70 mL) and saturated brine (70 mL). Each aqueous layer was back-extracted with chloroform (33 mL) sequentially. The organic layers were combined, dried over anhydrous magnesium sulfate, and filtered. The total amount of the residue obtained by concentration of the solvent under reduced pressure was dissolved in chloroform (16 mL), hexane (29 mL) was added, followed by stirring for 15 minutes. Further, hexane (5 mL) was added, followed by stirring and aging for 15 minutes. The precipitated solid was washed, filtered and dried to afford 3.37 g of the title compound (total yield 79%). Instrumental data were consistent with those of Reference Example 21.

Example 61

1-tert-Butyl 2-((3aR,7aS)-1,3-dioxohexahydro-1H-isoindol-2(3H)-yl) (2S,5R)-5-((benzyloxy)amino)piperidine-1,2-dicarboxylate (II-33)

[Chemical Formula 102]

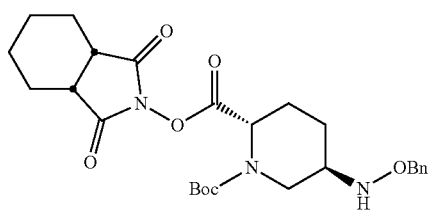

II-33

(2S,5R)-5-((Benzyloxy)amino)-1-(tert-butoxycarbonyl)piperidine-2-carboxylic acid (Reference Example 4, 3.504 g, 10 mmol) was dissolved in dehydrated tetrahydrofuran (50 mL), followed by cooling to around −20° C. To the mixture were added dropwise isobutyl chloroformate (1.51 g) and then triethylamine (2.17 g), followed by stirring at the same temperature for 15 minutes. Then, to the reaction solution was added (3aR,7aS)-2-hydroxyhexahydro-1H-isoindol-1,3(2H)-dione (Reference Example 22, 1.86 g), followed by stirring at the same temperature for 30 minutes and then at room temperature for 30 minutes. The reaction solution was diluted with ethyl acetate (200 mL), washed sequentially with ice-cold 10% citric acid (60 mL), saturated sodium bicarbonate (60 mL) and saturated brine (60 mL), dried over anhydrous magnesium sulfate, and filtered. The residue obtained by concentration of the filtrate under reduced pressure was subjected to silica gel column chromatography (hexane/ethyl acetate=2/1) to afford 4.521 g of the title compound as a colorless foamy solid (yield 90%).
$^1$H NMR (400 MHz, CDCl$_3$) δ 1.35-1.58 (m, 13H), 1.62 (bs, 1H), 1.76 (bs, 2H), 1.90 (bs, 4H), 1.95-2.15 (m, 2H), 3.00 (bs, 2H), 3.15-3.30 (m, 2H), 4.16-4.25 (m, 1H), 4.72 (q, J=11.6 Hz, 2H), 5.30-5.53 (m, 1H), 7.26-7.38 (m, 5H); MS m/z 502 [M+H]$^+$.

Example 62

(3aR,7aS)-1,3-Dioxohexahydro-1H-isoindol-2(3H)-yl (2S,5R)-6-(benzyloxy)-7-oxo-1,6-diazabicyclo[3.2.1]octane-2-carboxylate (III-60)

[Chemical Formula 103]

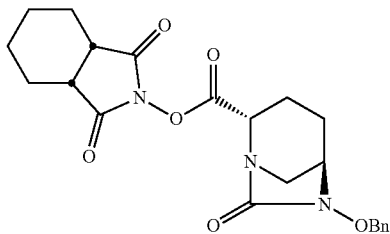

III-60

Step 1

1-tert-Butyl 2-((3aR,7aS)-1,3-dioxohexahydro-1H-isoindol-2(3H)-yl) (2S,5R)-5-((benzyloxy)((trichloromethoxy)carbonyl)amino)piperidine-1,2-dicarboxylate or 1-tert-butyl 2-((3aR,7aS)-1,3-dioxohexahydro-1H-isoindol-2(3H)-yl) (2S,5R)-5-((benzyloxy)(chlorocarbonyl)amino)piperidine-1,2-dicarboxylate 1-tert-Butyl 2-((3aR,7aS)-1,3-dioxohexahydro-1H-isoindol-2(3H)-yl) (2S,5R)-5-((benzyloxy)amino)piperidine-1,2-dicarboxylate (Example 61, 4.521 g, 9.01 mmol) was dissolved in dehydrated chloroform (50 mL), and triethylamine (1.350 g) was added, followed by ice cooling. To the mixture was added triphosgene (1.043 g), followed by stirring for 0.5 hours, and the completion of the reaction for the title compounds was confirmed by TLC. The compounds were subjected to the next step without purification and isolation.

Step 2

(3aR,7aS)-1,3-Dioxohexahydro-1H-isoindol-2(3H)-yl (2S,5R)-5-((benzyloxy) ((trichloromethoxy)carbonyl)amino)piperidine-2-carboxylate or (3aR,7aS)-1,3-dioxohexahydro-1H-isoindol-2(3H)-yl (2S,5R)-5-((benzyloxy)(chlorocarbonyl)amino) piperidine-2-carboxylate, methanesulfonate To the mixture in Step 1 above was added methanol (0.245 mL) under ice cooling, followed by stirring for 30 minutes. Subsequently, methanesulfonic acid (8.53 g) was added, followed by stirring for 30 minutes, and the completion of the reaction for the title compounds was confirmed by TLC. The compounds were subjected to the next step without purification and isolation.

Step 3

(3aR,7aS)-1,3-Dioxohexahydro-1H-isoindol-2(3H)-yl (2S,5R)-6-(benzyloxy)-7-oxo-1,6-diazabicyclo[3.2.1]octane-2-carboxylate The mixture in Step 2 above was added dropwise to ice-cold 1 M potassium bicarbonate (10.668 g/90 mL), followed by stirring for 0.5 hours. Chloroform (33 mL) was added, layers are separated, the organic layer was washed sequentially with 1 M hydrochloric acid (70 mL), saturated sodium bicarbonate (70 mL) and saturated brine (70 mL), dried over anhydrous magnesium sulfate, filtered, and concentrated under reduced pressure. The residue was subjected to silica gel column chromatography (chloroform/ethyl acetate=6/1) to afford 3.106 g of the title compound as a colorless solid (total yield over three steps: 81%). Instrumental data were consistent with those of Reference Example 23.

Example 63 tert-Butyl {2-[({[(2S,5R)-6-benzyloxy-7-oxo-1,6-diazabicyclo[3.2.1]oct-2-yl]carbonyl}amino)oxy]ethyl}carbamate (IV-1-1)

[Chemical Formula 104]

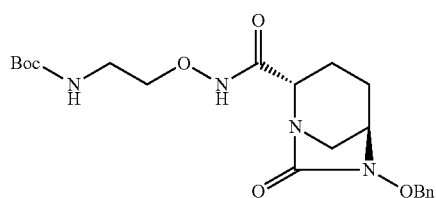

IV-1-1

Example 63a

[Chemical Formula 105]

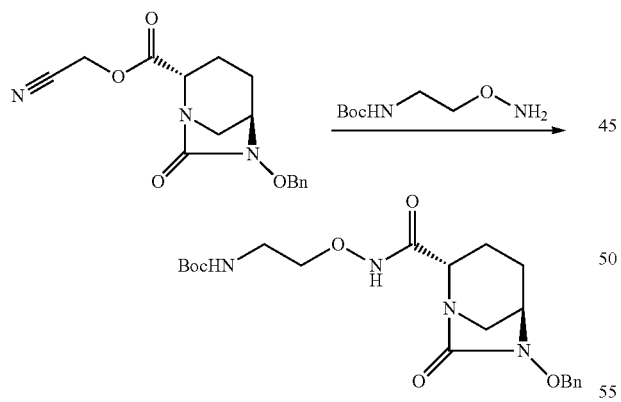

Cyanomethyl (2S,5R)-6-(benzyloxy)-7-oxo-1,6-diazabicyclo[3.2.1]octane-2-carboxylate (Example 36, 315.3 mg, 1.00 mmol) was dissolved in dehydrated dichloromethane (5.0 mL), and a solution of tert-butyl 2-(aminooxy)ethylcarbamate (194 mg) in dehydrated dichloromethane (2.0 mL) was added under ice cooling, followed by stirring for 1 hour. Triethylamine (153 µL) was added, followed by stirring for 30 minutes. Subsequently, the temperature was elevated to room temperature, followed by stirring overnight. The reaction solution was diluted with ethyl acetate (65 mL), washed sequentially with 10% citric acid (20 mL), saturated sodium bicarbonate (20 mL) and saturated brine (20 mL), dried over anhydrous magnesium sulfate, filtered, concentrated under reduced pressure, and subsequently subjected to silica gel column chromatography (hexane/ethyl acetate=92/8 to 0/100) to afford 45.1 mg of the title compound (yield 10%). Instrumental data were consistent with those of Reference Example 3, Step 1.

Example 63b

[Chemical Formula 106]

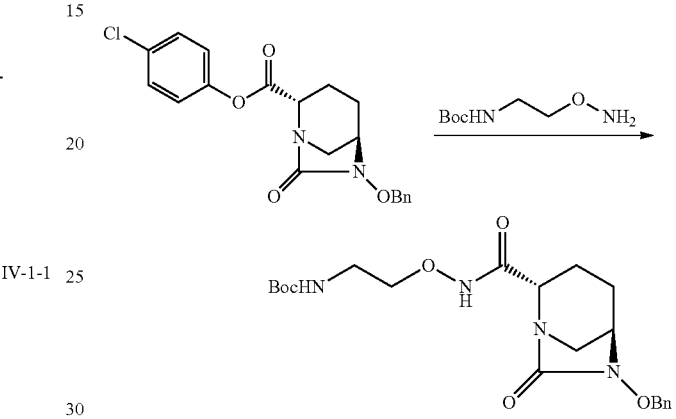

4-Chlorophenyl (2S,5R)-6-(benzyloxy)-7-oxo-1,6-diazabicyclo[3.2.1]octane-2-carboxylate (Example 37, 89.33 mg, 230.9 µmol) was dissolved in dehydrated dichloromethane (1.1 mL), and a solution of tert-butyl 2-(aminooxy)ethylcarbamate (43.0 mg) in dehydrated dichloromethane (443 µL) was added under ice cooling, followed by stirring for 1 hour. Triethylamine (35.4 µL) was added, followed by stirring for 1 hour. Subsequently, the temperature was elevated to room temperature, followed by stirring overnight. The reaction solution was diluted with ethyl acetate (15.0 mL), washed sequentially with 10% citric acid (4.6 mL), saturated sodium bicarbonate (4.6 mL) and saturated brine (4.6 mL), dried over anhydrous magnesium sulfate, filtered, concentrated under reduced pressure, and then subjected to silica gel column chromatography (hexane/ethyl acetate=1/2) to afford 28.1 mg of the title compound (yield 28%). Instrumental data were consistent with those of Reference Example 3, Step 1.

Example 63c

[Chemical Formula 107]

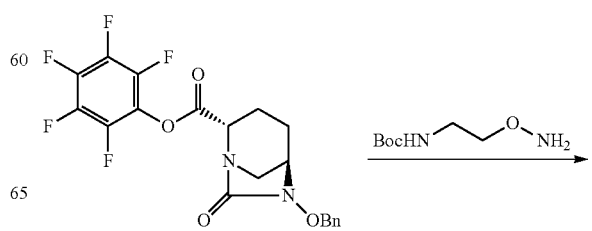

113

-continued

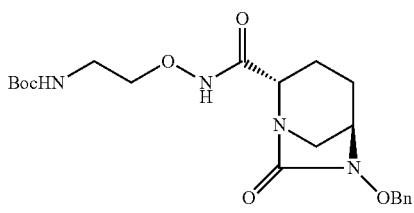

2,3,4,5,6-Pentafluorophenyl (2S,5R)-6-(benzyloxy)-7-oxo-1,6-diazabicyclo[3.2.1]octane-2-carboxylate (Example 39, 69.0 mg, 0.156 mmol) was dissolved in dehydrated dichloromethane (1.3 mL), and a solution of tert-butyl 2-(aminooxy)ethylcarbamate (59.3 mg) in dehydrated dichloromethane (0.4 mL) was added under ice cooling, followed by stirring for 1 hour. The reaction solution was diluted with ethyl acetate (10 mL), washed sequentially with 0.25 M hydrochloric acid, saturated sodium bicarbonate and saturated brine, dried over anhydrous magnesium sulfate, filtered, concentrated under reduced pressure, and subsequently subjected to silica gel column chromatography (hexane/ethyl acetate=1/1 to 0/1) to afford 36.7 mg of the title compound (yield 54%). Instrumental data were consistent with those of Reference Example 3, Step 1.

Example 63d

[Chemical Formula 108]

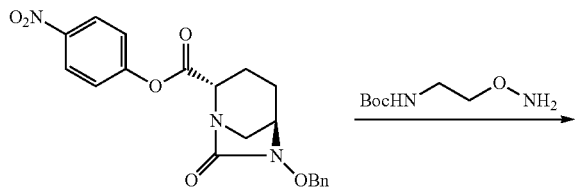

4-Nitrophenyl (2S,5R)-6-(benzyloxy)-7-oxo-1,6-diazabicyclo[3.2.1]octane-2-carboxylate (Example 40, 71.66 mg, 180.3 μmol) was dissolved in dehydrated dichloromethane (902 μL), and a solution of tert-butyl 2-(aminooxy)ethylcarbamate (35.0 mg) in dehydrated dichloromethane (361 μL) was added under ice cooling, followed by stirring for 1 hour. The reaction solution was diluted with ethyl acetate (12 mL), washed sequentially with 10% citric acid (3.6 mL), saturated sodium bicarbonate (3.6 mL) and saturated brine (3.6 mL), dried over anhydrous magnesium sulfate, filtered, concentrated under reduced pressure, and subsequently subjected to silica gel column chromatography (hexane/ethyl acetate=1/2) to afford 29.5 mg of the title compound (yield 38%). Instrumental data were consistent with those of Reference Example 3, Step 1.

114

Example 63e

[Chemical Formula 109]

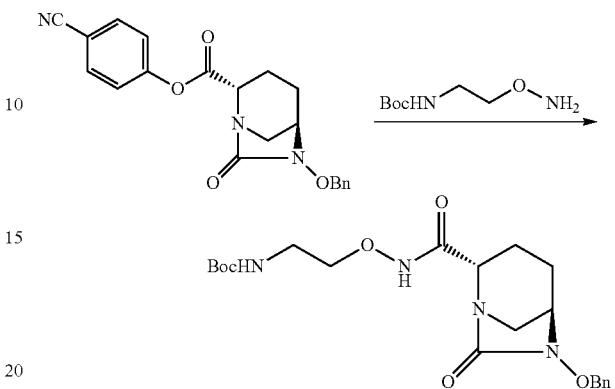

4-Cyanophenyl (2S,5R)-6-(benzyloxy)-7-oxo-1,6-diazabicyclo[3.2.1] octane-2-carboxylate (Example 41, 57 mg, 0.151 mmol) was dissolved in dehydrated dichloromethane (1.5 mL), and a solution of tert-butyl 2-(aminooxy)ethylcarbamate (60.9 mg) in dehydrated dichloromethane (0.4 mL) and triethylamine (42.5 μL) were added under ice cooling, followed by stirring at room temperature for 2 days. The reaction solution was diluted with ethyl acetate (10 mL), washed sequentially with 0.25 M hydrochloric acid, saturated sodium bicarbonate and saturated brine, dried over anhydrous magnesium sulfate, filtered, concentrated under reduced pressure, and subsequently subjected to silica gel column chromatography (hexane/ethyl acetate=1/1 to 0/1) to afford 44.8 mg of the title compound (yield 68%). Instrumental data were consistent with those of Reference Example 3, Step 1.

Example 63f

[Chemical Formula 110]

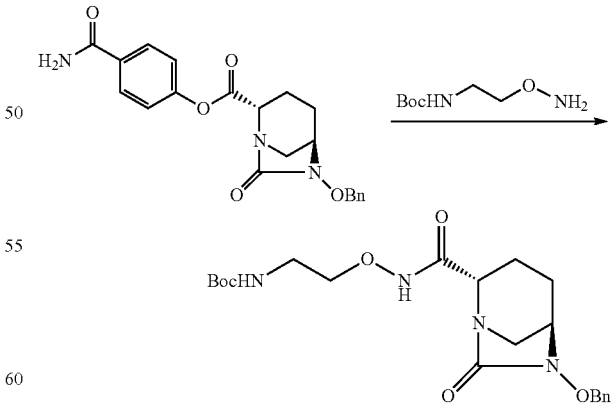

4-Carbamoylphenyl (2S,5R)-6-(benzyloxy)-7-oxo-1,6-diazabicyclo[3.2.1] octane-2-carboxylate (Example 42, 203 mg, 0.513 mmol) was dissolved in dehydrated dichloromethane (3 mL), and a solution of tert-butyl 2-(aminooxy) ethylcarbamate (121 mg) in dehydrated dichloromethane (1.5 mL) and triethylamine (86 µL) were added under ice cooling, followed by stirring at room temperature for 4 days. The reaction solution was diluted with ethyl acetate (10 mL), washed sequentially with 0.25 M hydrochloric acid, saturated sodium bicarbonate and saturated brine, dried over anhydrous magnesium sulfate, filtered, concentrated under reduced pressure, and subsequently subjected to silica gel column chromatography (hexane/ethyl acetate=1/1 to 1/4) to afford 166 mg of the title compound (yield 75%). Instrumental data were consistent with those of Reference Example 3, Step 1.

Example 63g

[Chemical Formula 111]

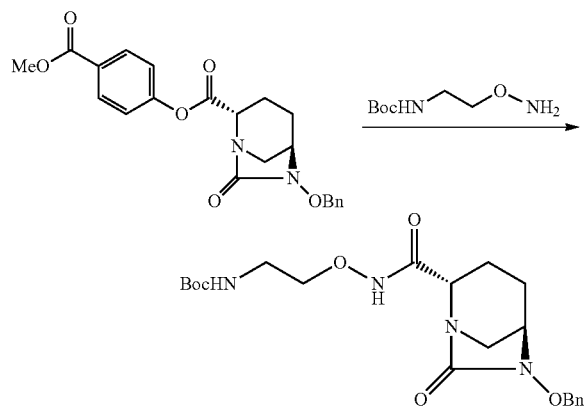

4-Methoxycarbonylphenyl (2S,5R)-6-(benzyloxy)-7-oxo-1,6-diazabicyclo [3.2.1]octane-2-carboxylate (Example 43, 55.7 mg, 0.136 mmol) was dissolved in dehydrated dichloromethane (1 mL), and a solution of tert-butyl 2-(aminooxy) ethylcarbamate (48.8 mg) in dehydrated dichloromethane (0.4 mL) and triethylamine (28.7 µL) were added under ice cooling, followed by stirring at room temperature for 2 days. The reaction solution was diluted with ethyl acetate (10 mL), washed sequentially with 0.25 M hydrochloric acid, saturated sodium bicarbonate and saturated brine, dried over anhydrous magnesium sulfate, filtered, concentrated under reduced pressure, and subsequently subjected to silica gel column chromatography (hexane/ethyl acetate=1/1 to 0/1) to afford 38.7 mg of the title compound (yield 66%). Instrumental data were consistent with those of Reference Example 3, Step 1.

Example 63h

[Chemical Formula 112]

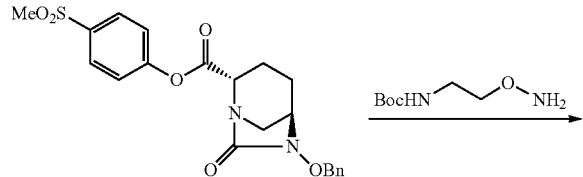

-continued

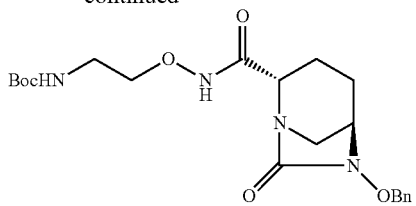

4-Methylsulfonylphenyl (2S,5R)-6-(benzyloxy)-7-oxo-1,6-diazabicyclo [3.2.1]octane-2-carboxylate (Example 44, 76.24 mg, 177.1 µmol) was dissolved in dehydrated dichloromethane (854 µL), and a solution of tert-butyl 2-(aminooxy) ethylcarbamate (33.1 mg) in dehydrated dichloromethane (341 µL) were added under ice cooling, followed by stirring for 1 hour. Further, triethylamine (27.2 µL) was added and stirred for 1 hour. Subsequently, the temperature was elevated to room temperature, followed by stirring overnight. The reaction solution was diluted with ethyl acetate (12 mL), washed sequentially with 10% citric acid (3.5 mL), saturated sodium bicarbonate (3.5 mL) and saturated brine (3.5 mL), dried over anhydrous magnesium sulfate, filtered, concentrated under reduced pressure, and subsequently subjected to silica gel column chromatography (hexane/ethyl acetate=1/2) to afford 34.1 mg of the title compound (yield 44%). Instrumental data were consistent with those of Reference Example 3, Step 1.

Example 63i

[Chemical Formula 113]

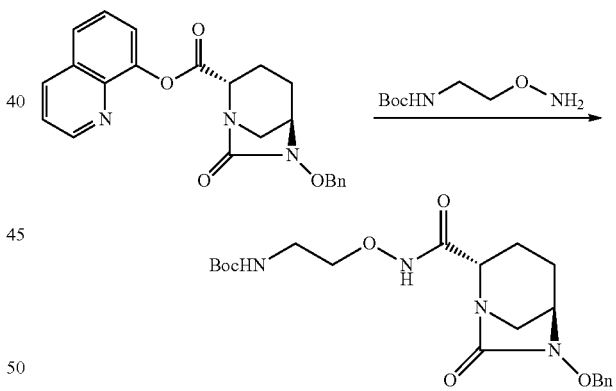

Quinolin-8-yl (2S,5R)-6-(benzyloxy)-7-oxo-1,6-diazabicyclo[3.2.1]octane-2-carboxylate (Example 45, 87.13 mg, 216.0 µmol) was dissolved in dehydrated dichloromethane (1.1 mL), and a solution of tert-butyl 2-(aminooxy)ethylcarbamate (41.9 mg) in dehydrated dichloromethane (432 µL) was added under ice cooling, followed by stirring for 1 hour. The reaction solution was diluted with ethyl acetate (14 mL), washed sequentially with 10% citric acid (4.3 mL), saturated sodium bicarbonate (4.3 mL) and saturated brine (4.3 mL), dried over anhydrous magnesium sulfate, filtered, concentrated under reduced pressure, and subsequently subjected to silica gel column chromatography (hexane/ethyl acetate=2/1) to afford 28.6 mg of the title compound (yield 30%). Instrumental data were consistent with those of Reference Example 3, Step 1.

Example 63j

[Chemical Formula 114]

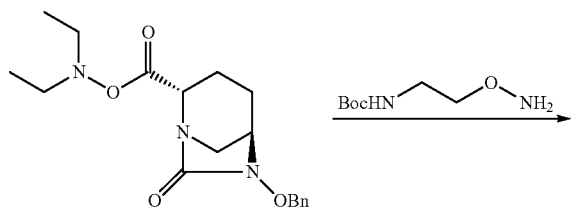

Diethylamino (2S,5R)-6-(benzyloxy)-7-oxo-1,6-diazabicyclo[3.2.1]octane-2-carboxylate (Example 47, 122 mg, 0.350 mmol) was dissolved in dehydrated dichloromethane (2.5 mL), and a solution of tert-butyl 2-(aminooxy)ethylcarbamate (127 mg) in dehydrated dichloromethane (0.5 mL) was added under ice cooling, followed by stirring at room temperature for 4 days. The reaction solution was diluted with ethyl acetate (10 mL), washed sequentially with 0.25 M hydrochloric acid, saturated sodium bicarbonate and saturated brine, dried over anhydrous sodium sulfate, filtered, concentrated under reduced pressure, and subsequently subjected to silica gel column chromatography (hexane/ethyl acetate=1/1 to 0/1) to afford 42.0 mg of the title compound (yield 28%). Instrumental data were consistent with those of Reference Example 3, Step 1.

Example 63k

[Chemical Formula 115]

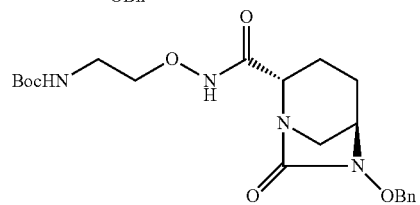

1,3-Dioxo-1,3-dihydro-2H-isoindol-2-yl (2S,5R)-6-(benzyloxy)-7-oxo-1,6-diazabicyclo[3.2.1]octane-2-carboxylate (Example 49, 100.6 mg, 239 µmol) was dissolved in dehydrated dichloromethane (1.2 mL), and a solution of tert-butyl 2-(aminooxy)ethylcarbamate (46.3 mg) in dehydrated dichloromethane (477 µL) was added under ice cooling, followed by stirring for 1 hour. The reaction solution was diluted with ethyl acetate (16 mL), washed sequentially with 10% citric acid (4.8 mL), saturated sodium bicarbonate (4.8 mL) and saturated brine (4.8 mL), dried over anhydrous magnesium sulfate, filtered, concentrated under reduced pressure, and subsequently subjected to silica gel column chromatography (hexane/ethyl acetate=1/2) to afford 41.0 mg of the title compound (yield 40%). Instrumental data were consistent with those of Reference Example 3, Step 1.

Example 63l

[Chemical Formula 116]

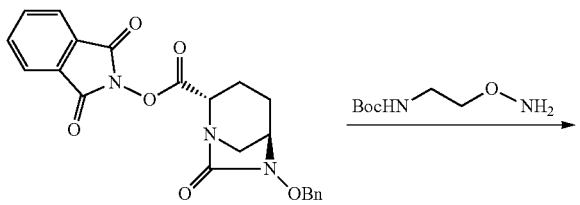

S-(4-Nitrophenyl) (2S,5R)-6-(benzyloxy)-7-oxo-1,6-diazabicyclo[3.2.1] octane-2-carbothioate (Example 52, 49.04 mg, 118.6 µmol) was dissolved in dehydrated dichloromethane (593 µL), and a solution of tert-butyl 2-(aminooxy)ethylcarbamate (23.0 mg) in dehydrated dichloromethane (237 µL) was added under ice cooling, followed by stirring for 1 hour. Triethylamine (18.2 µL) was added, followed by stirring for 30 minutes. Subsequently, the temperature was elevated to room temperature, followed by stirring overnight. The reaction solution was diluted with ethyl acetate (7.7 mL), washed sequentially with 10% citric acid (2.4 mL), saturated sodium bicarbonate (2.4 mL) and saturated brine (2.4 mL), dried over anhydrous magnesium sulfate, filtered, concentrated under reduced pressure, and subsequently subjected to silica gel column chromatography (hexane/ethyl acetate=1/2) to afford 22.3 mg of the title compound (yield 43%). Instrumental data were consistent with those of Reference Example 3, Step 1.

Example 63m

[Chemical Formula 117]

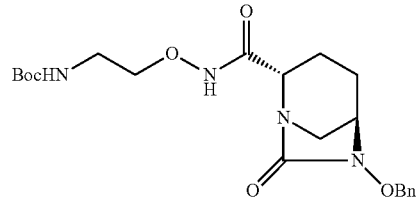

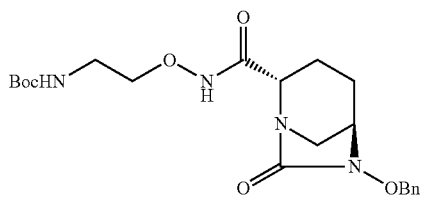

S-(5-Nitropyridine-2-yl) (2S,5R)-6-(benzyloxy)-7-oxo-1,6-diazabicyclo [3.2.1]octane-2-carbothioate (Example 54, 55.1 mg, 0.133 mmol) was dissolved in dehydrated dichloromethane (1.0 mL), and a solution of tert-butyl 2-(aminooxy) ethylcarbamate (32.5 mg) in dehydrated dichloromethane (0.4 mL) was added under ice cooling, followed by stirring for 1 hour. The reaction solution was diluted with ethyl acetate (10 mL), washed sequentially with 0.25 M hydrochloric acid, saturated sodium bicarbonate and saturated brine, dried over anhydrous sodium sulfate, filtered, concentrated under reduced pressure, and subsequently subjected to silica gel column chromatography (hexane/ethyl acetate=1/1 to 0/1) to afford 35.6 mg of the title compound (yield 62%). Instrumental data were consistent with those of Reference Example 3, Step 1.

Example 63n

[Chemical Formula 118]

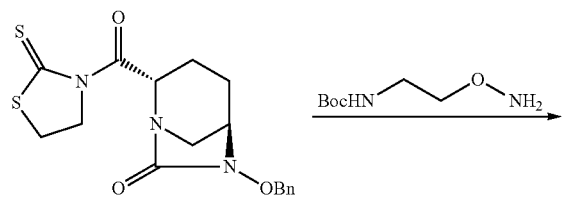

(2S,5R)-6-(Benzyloxy)-2-[(2-thioxo-1,3-thiazolidine-3-yl)carbonyl]-1,6-diazabicyclo[3.2.1]octane-7-one (Example 55, 67.94 mg, 180.0 μmol) was dissolved in dehydrated dichloromethane (900 μL), and a solution of tert-butyl 2-(aminooxy)ethylcarbamate (34.9 mg) in dehydrated dichloromethane (360 μL) was added under ice cooling, followed by stirring for 1 hour. The reaction solution was diluted with ethyl acetate (12 mL), washed sequentially with 10% citric acid (3.6 mL), saturated sodium bicarbonate (3.6 mL) and saturated brine (3.6 mL), dried over anhydrous magnesium sulfate, filtered, concentrated under reduced pressure, and subsequently subjected to silica gel column chromatography (hexane/ethyl acetate=2/1) to afford 62.1 mg of the title compound (yield 79%). Instrumental data were consistent with those of Reference Example 3, Step 1.

Example 63o

[Chemical Formula 119]

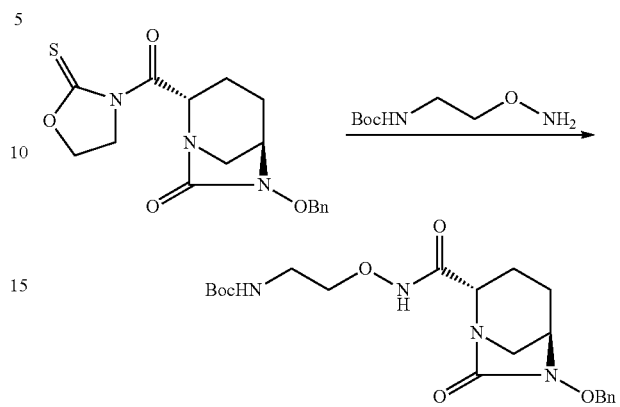

(2S,5R)-6-(Benzyloxy)-2-[(2-thioxo-1,3-oxazolidine-3-yl)carbonyl]-1,6-diazabicyclo[3.2.1]octane-7-one (Example 56, 54.7 mg, 0.151 mmol) was dissolved in dehydrated dichloromethane (1.3 mL), and a solution of tert-butyl 2-(aminooxy)ethylcarbamate (57.5 mg) in dehydrated dichloromethane (0.4 mL) and triethylamine (42.5 μL) were added under ice cooling, followed by stirring at room temperature for 19 hours. The reaction solution was diluted with ethyl acetate (10 mL), washed sequentially with 0.25 M hydrochloric acid, saturated sodium bicarbonate and saturated brine, dried over anhydrous magnesium sulfate, filtered, concentrated under reduced pressure, and subsequently subjected to silica gel column chromatography (hexane/ethyl acetate=1/1 to 0/1) to afford 47.4 mg of the title compound (yield 73%). Instrumental data were consistent with those of Reference Example 3, Step 1.

Example 63p

[Chemical Formula 120]

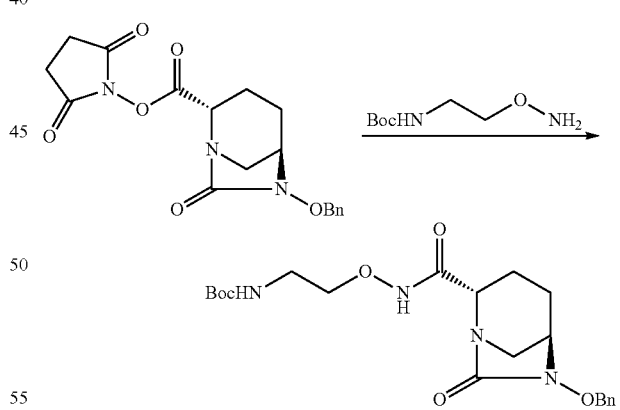

2,5-Dioxopyrrolidine-1-yl (2S,5R)-6-(benzyloxy)-7-oxo-1,6-diazabicyclo [3.2.1]octane-2-carboxylate (Example 57a-c, 373 mg, 1 mmol) was dissolved in dehydrated dichloromethane (5 mL), and a solution of tert-butyl 2-(aminooxy) ethylcarbamate (194 mg) in dehydrated dichloromethane (2 mL, washed with 1 mL) was added under ice cooling, followed by stirring for 1 hour. The reaction solution was diluted with ethyl acetate (65 mL), washed sequentially with 10% citric acid (20 mL), saturated sodium bicarbonate (20 mL) and saturated brine (20 mL), dried over anhydrous magnesium sulfate, filtered, and concentrated under reduced pressure to afford 362 mg of the title com-

Example 63q

[Chemical Formula 121]

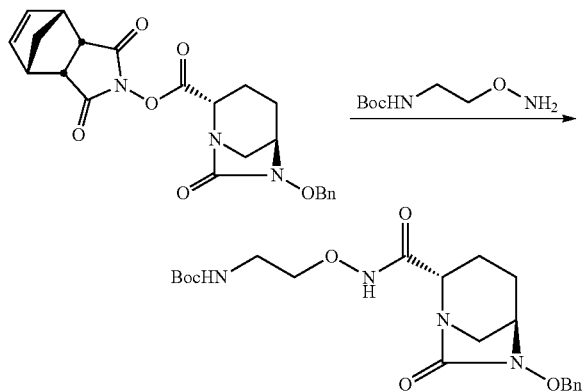

(1R,2S,6R,7S)-3,5-Dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate (Examples 58a-c, 49.7 g, 113.6 mmol) was suspended in dehydrated ethyl acetate (650 mL), and a solution of tert-butyl 2-(aminooxy)ethylcarbamate (24.2 g) in dehydrated ethyl acetate (134 mL) and triethylamine (13.8 g) were added at room temperature, followed by stirring for 2.5 hours. The reaction solution was diluted with ethyl acetate (0.8 L), washed sequentially with ice-cold 0.25 M hydrochloric acid (1 L), saturated sodium bicarbonate (1 L) and water (1 L), and concentrated under reduced pressure to afford 50.67 g of the title compound (net 48.08 g, yield 98%, HPLC area ratio 99% or more). Instrumental data were consistent with those of Reference Example 3, Step 1.

Example 63r

[Chemical Formula 122]

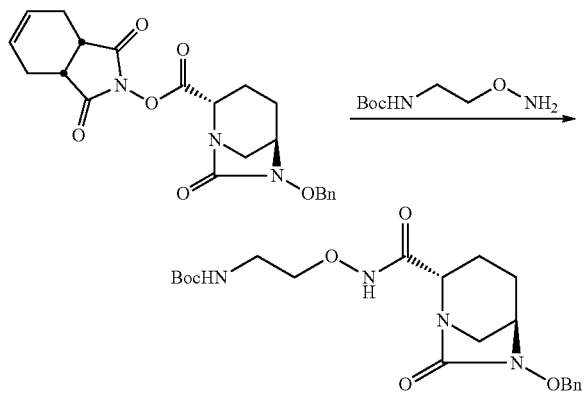

(3aR,7aS)-1,3-Dioxo-3a,4,7,7a-tetrahydro-1H-isoindol-2(3H)-yl (2S,5R)-6-(benzyloxy)-7-oxo-1,6-diazabicyclo[3.2.1]octane-2-carboxylate (Examples 60a-b, 425 mg, 1 mmol) was dissolved in dehydrated chloroform (5 mL), and a solution of tert-butyl 2-(aminooxy)ethyl carbamate (211 mg) in dehydrated ethyl acetate (1.41 g) and triethylamine (121 mg) were added under ice cooling, followed by stirring for 30 minutes. The reaction solution was diluted with ethyl acetate (75 mL), washed sequentially with 10% citric acid aqueous solution (35 mL), saturated sodium bicarbonate (35 mL) and saturated brine (35 mL), and dried over anhydrous magnesium sulfate. The filtrate was concentrated under reduced pressure. The residue was subjected to silica gel column chromatography (hexane/ethyl acetate=1/2) to afford 481 mg of the title compound (quantitative). Instrumental data were consistent with those of Reference Example 3, Step 1.

Example 63s

[Chemical Formula 123]

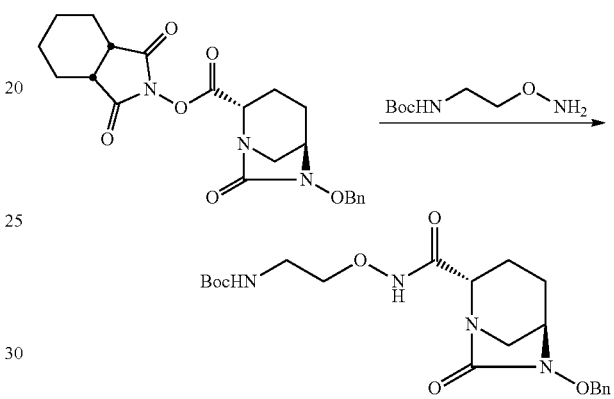

(3aR,7aS)-1,3-Dioxohexahydro-1H-isoindol-2(3H)-yl (2S,5R)-6-(benzyloxy)-7-oxo-1,6-diazabicyclo[3.2.1]octane-2-carboxylate (Example 62, 427 mg, 1 mmol) was dissolved in dehydrated chloroform (5 mL), and a solution of tert-butyl 2-(aminooxy)ethyl carbamate (211 mg) in dehydrated ethyl acetate (1.41 g) and triethylamine (121 mg) were added under ice cooling, followed by stirring for 30 minutes. The reaction solution was diluted with ethyl acetate (75 mL), washed sequentially with 10% citric acid aqueous solution (35 mL), saturated sodium bicarbonate (35 mL) and saturated brine (35 mL), and dried over anhydrous magnesium sulfate. The filtrate was concentrated under reduced pressure. The residue was subjected to silica gel column chromatography (hexane/ethyl acetate=1/2) to afford 418 mg of the title compound (yield 96%). Instrumental data were consistent with those of Reference Example 3, Step 1.

Example 64 tert-Butyl {2-[({[(2S,5R)-6-hydroxy-7-oxo-1,6-diazabicyclo[3.2.1]oct-2-yl] carbonyl}amino)oxy]ethyl}carbamate (V-1)

[Chemical Formula 124]

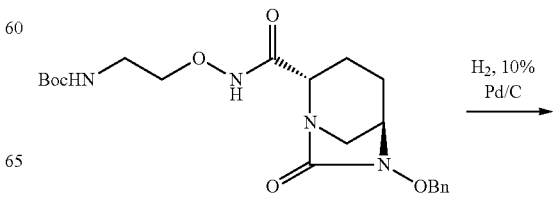

123

-continued

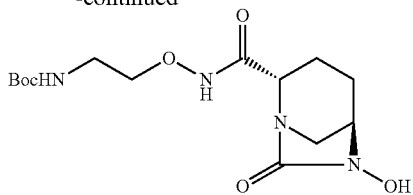

To a solution of tert-butyl {2-[({[(2S,5R)-6-benzyloxy-7-oxo-1,6-diazabicyclo [3.2.1]oct-2-yl]carbonyl}amino)oxy] ethyl}carbamate (Example 63q, net 156.42 g, 360 mmol) in methanol (2.4 L) was added a 10% palladium carbon catalyst (50% water content, 15.64 g), followed by stirring under a hydrogen atmosphere for 1.5 hours. The catalyst was filtered through a Celite pad, and the filtrate was concentrated under reduced pressure to 450 mL, and subsequently acetonitrile (1.5 L) was added, followed by concentration to 450 mL. The mixture was ice cooled and stirred for 30 minutes, and the precipitated crystalline solid was filtered, washed with acetonitrile, and dried in vacuo to afford 118.26 g of the title compound (net 117.90 g, yield 95%). Instrumental data were consistent with those of Reference Example 3, Step 2.

Example 65

(2S,5R)—N-(2-Aminoethoxy)-7-oxo-6-(sulfooxy)-1, 6-diazabicyclo[3.2.1]octane-2-carboxamide (VI-1)

[Chemical Formula 125]

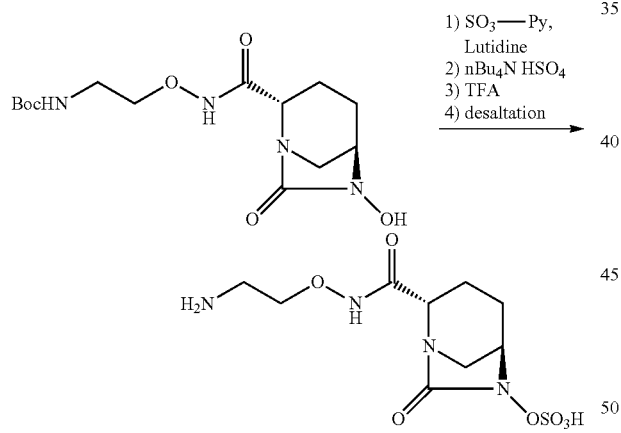

To a solution of tert-butyl {2-[({[(2S,5R)-6-hydroxy-7-oxo-1,6-diazabicyclo[3.2.1]oct-2-yl]carbonyl}amino)oxy] ethyl}carbamate (Example 64, 537.61 g, 1.561 mol) in acetonitrile (7.8 L) were added 2,6-lutidine (512.08 g) and sulfur trioxide-pyridine complex (810.3 g), followed by stirring at room temperature overnight. The mixture was filtered to remove insolubles, and the filtrate was concentrated to 2.5 L and diluted with ethyl acetate (15.1 L). The mixture was extracted with 20% sodium dihydrogen phosphate (7.8 L), to the resulting aqueous layer were added ethyl acetate (15.1 L) and tetrabutylammonium hydrogen sulfate (567.87 g), followed by stirring for 20 minutes. The organic layer was separated, dried over anhydrous magnesium sulfate (425 g), filtered, subsequently concentrated under reduced pressure, and solvent-switched to dichloromethane (3.1 L) to afford 758 g of tetrabutylammonium tert-butyl {2-[({[(2S,5R)-7-oxo-6-(sulfooxy)-1,6-diazabicyclo[3.2.1]oct-2-yl]carbonyl} amino)oxy]ethyl}carbamate (net 586.27 g, yield 84%).

A solution of 719 g of the tetrabutylammonium salt (net 437.1 g, 0.656 mol) in dichloromethane (874 mL) was cooled to −20° C., trifluoroacetic acid (874 mL) was added dropwise for 15 minutes, and the temperature was elevated to 0° C., followed by stirring for 1 hour. The reaction solution was cooled to −20° C., diisopropyl ether (3.25 L) was added dropwise, the temperature of the mixture was elevated to 0° C., followed by stirring for 1 hour. The precipitates was filtered, washed with diisopropyl ether, and dried in vacuo to afford 335.36 g of the crude title compound (net 222.35 g, yield 99%).

The crude title compound (212.99 g, net 133.33 g) and an ice-cold 0.2 M phosphate buffer (pH 6.5, 4.8 L) were mixed alternately in small portions to give a solution having pH 5.3. The solution was concentrated under reduced pressure to 3.6 L, and the pH was again adjusted to pH 5.5 using a 0.2 M phosphate buffer (pH 6.5, 910 mL). The solution was subjected to resin purification (Mitsubishi Kasei, SP207, water to 10% IPA-water) and active fractions were collected, concentrated and lyophilized. 128.3 g of the title compound was then obtained (yield 96%). Instrumental data were consistent with those of Reference Example 3, Step 3.

Example 66

Benzyl {2-[({[(2S,5R)-6-benzyloxy-7-oxo-1,6-diazabicyclo[3.2.1]oct-2-yl]carbonyl}amino)oxy] ethyl}carbamate (IV-1-2)

[Chemical Formula 126]

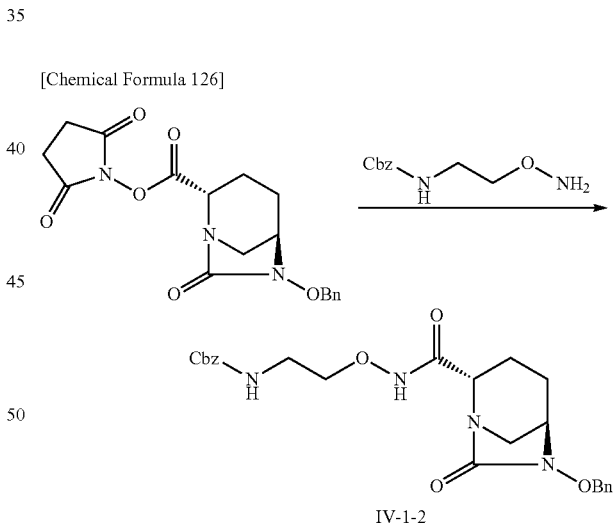

2,5-Dioxopyrrolidine-1-yl (2S,5R)-6-(benzyloxy)-7-oxo-1,6-diazabicyclo[3.2.1]octane-2-carboxylate (Example 57a-c, 201 mg, 0.538 mmol) was dissolved in dehydrated dichloromethane (4 mL), and a solution of benzyl 2-(aminooxy) ethylcarbamate (128 mg) in dehydrated dichloromethane (0.5 mL, washed with 0.5 mL) was added under ice cooling, followed by stirring for 1.5 hours. The reaction solution was diluted with ethyl acetate (30 mL), washed sequentially with 10% citric acid (15 mL), saturated sodium bicarbonate (15 mL) and saturated brine (15 mL), dried over anhydrous magnesium sulfate, filtered, and concentrated under reduced pressure to afford 222 mg of the title compound (yield 88%). Instrumental data were consistent with those of Reference Example 5, Step 3.

Example 67 tert-Butyl {2-[({[(2S,5R)-6-benzyloxy-7-oxo-1,6-diazabicyclo[3.2.1]oct-2-yl] carbonyl}amino)oxy]ethyl}(methyl) carbamate (IV-2)

[Chemical Formula 127]

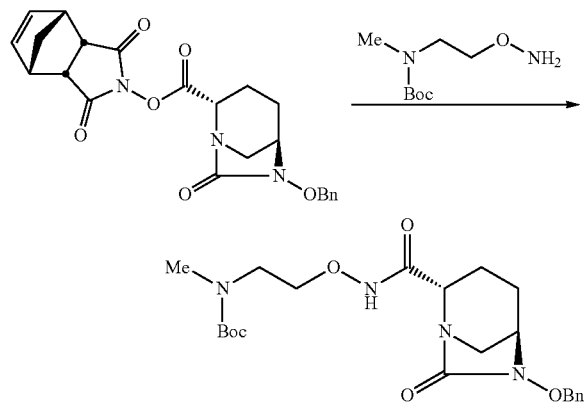

(1R,2S,6R,7S)-3,5-Dioxo-4-azatricyclo[5.2.1.0²,⁶]dec-8-en-4-yl (2S,5R)-6-(benzyloxy)-7-oxo-1,6-diazabicyclo[3.2.1]octane-2-carboxylate (Example 58a-c, 144 mg, 0.329 mmol) was dissolved in dehydrated dichloromethane (2.5 mL), and a solution of tert-butyl (2-(aminooxy)ethyl)(methyl)carbamate (88.8 mg) in dehydrated dichloromethane (0.5 mL) was added, followed by stirring at room temperature for 18 hours. The reaction solution was diluted with ethyl acetate (10 mL), washed sequentially with 0.25 M hydrochloric acid, saturated sodium bicarbonate and saturated brine, dried over anhydrous sodium sulfate, filtered, and concentrated under reduced pressure to afford 132 mg of the title compound (yield 89%). Instrumental data were consistent with those of Reference Example 6, Step 1.

Example 68 tert-Butyl {3-[({[(2S,5R)-6-benzyloxy-7-oxo-1,6-diazabicyclo[3.2.1]oct-2-yl] carbonyl}amino)oxy]propyl}carbamate (IV-7)

[Chemical Formula 128]

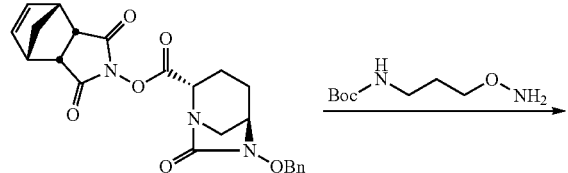

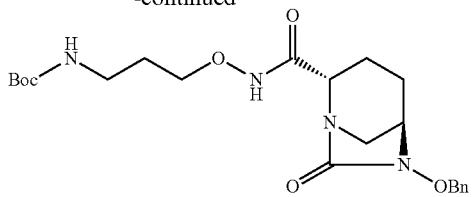

(1R,2S,6R,7S)-3,5-Dioxo-4-azatricyclo[5.2.1.0²,⁶]dec-8-en-4-yl (2S,5R)-6-(benzyloxy)-7-oxo-1,6-diazabicyclo[3.2.1]octane-2-carboxylate (Example 58a-c, 148 mg, 0.339 mmol) was dissolved in dehydrated dichloromethane (2.5 mL), and a solution of tert-butyl 3-(aminooxy)propylcarbamate (90.9 mg) in dehydrated dichloromethane (0.5 mL) was added, followed by stirring at room temperature for 18 hours. The reaction solution was diluted with ethyl acetate (10 mL), washed sequentially with 0.25 M hydrochloric acid, saturated sodium bicarbonate and saturated brine, dried over anhydrous sodium sulfate, filtered, and concentrated under reduced pressure to afford 134 mg of the title compound (yield 88%). Instrumental data were consistent with those of Reference Example 11, Step 1.

Example 69 tert-Butyl (2S)-2-{[({[(2S,5R)-6-benzyloxy-7-oxo-1,6-diazabicyclo[3.2.1]oct-2-yl]carbonyl}amino)oxy]methyl}azetidine-1-carboxylate (IV-8)

[Chemical Formula 129]

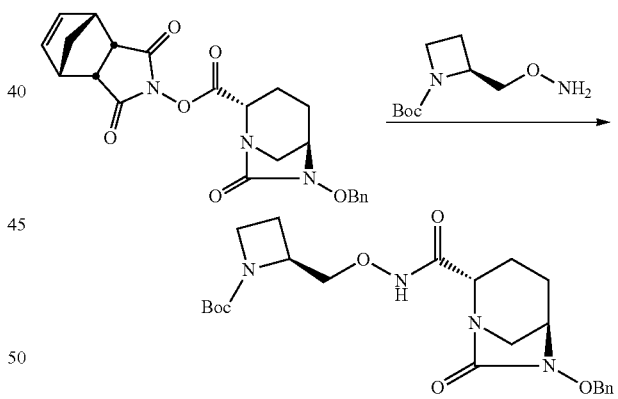

(1R,2S,6R,7S)-3,5-Dioxo-4-azatricyclo[5.2.1.0²,⁶]dec-8-en-4-yl (2S,5R)-6-(benzyloxy)-7-oxo-1,6-diazabicyclo[3.2.1]octane-2-carboxylate (Example 58a-c, 145 mg, 0.331 mmol) was dissolved in dehydrated dichloromethane (2.5 mL), and a solution of (S)-tert-butyl 2-((aminooxy)methyl)azetidine-1-carboxylate (93.2 mg) in dehydrated dichloromethane (0.5 mL) was added, followed by stirring at room temperature for 21 hours. The reaction solution was diluted with ethyl acetate (10 mL), washed sequentially with 0.25 M hydrochloric acid, saturated sodium bicarbonate and saturated brine, dried over anhydrous sodium sulfate, filtered, and concentrated under reduced pressure to afford 127 mg of the title compound (yield 83%). Instrumental data were consistent with those of Reference Example 12, Step 1.

Example 70 tert-Butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate (IV-11)

[Chemical Formula 130]

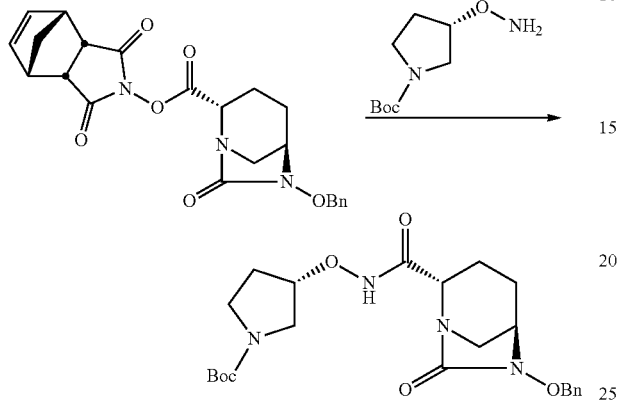

(1R,2S,6R,7S)-3,5-Dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate (Example 58a-c, 145 mg, 0.332 mmol) was dissolved in dehydrated dichloromethane (2.5 mL), and a solution of (S)-tert-butyl 3-(aminooxy)pyrrolidine-1-carboxylate (91.6 mg) in dehydrated dichloromethane (0.5 mL) was added, followed by stirring at room temperature for 19 hours. The reaction solution was diluted with ethyl acetate (10 mL), washed sequentially with 0.25 M hydrochloric acid, saturated sodium bicarbonate and saturated brine, dried over anhydrous sodium sulfate, filtered, and concentrated under reduced pressure to afford 145 mg of the title compound (yield 95%). Instrumental data were consistent with those of Reference Example 15, Step 1.

Example 71 tert-Butyl 3-{[({[(2S,5R)-6-benzyloxy-7-oxo-1,6-diazabicyclo[3.2.1]oct-2-yl] carbonyl}amino)oxy]methyl}azetidine-1-carboxylate (IV-12)

[Chemical Formula 131]

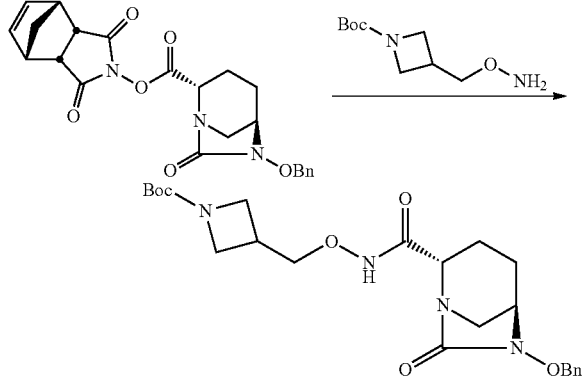

(1R,2S,6R,7S)-3,5-Dioxo-4-azatricyclo[5.2.1.0$^{2,6}$]dec-8-en-4-yl (2S,5R)-6-(benzyloxy)-7-oxo-1,6-diazabicyclo[3.2.1]octane-2-carboxylate (Example 58a-c, 140 mg, 0.320 mmol) was dissolved in dehydrated dichloromethane (2.5 mL), and a solution of tert-butyl 3-((aminooxy)methyl)azetidine-1-carboxylate (91.5 mg) in dehydrated dichloromethane (0.5 mL) was added, followed by stirring at room temperature for 20 hours. The reaction solution was diluted with ethyl acetate (10 mL), washed sequentially with 0.25 M hydrochloric acid, saturated sodium bicarbonate and saturated brine, dried over anhydrous sodium sulfate, filtered, and concentrated under reduced pressure to afford 132 mg of the title compound (yield 90%). Instrumental data were consistent with those of Reference Example 16, Step 1.

The invention claimed is:
1. A process for producing a compound represented by a Formula (III), comprising: reacting a compound represented by the following Formula (I):

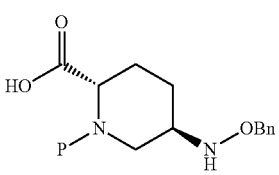

with a compound selected from the group consisting of 1-hydroxypyrrolidine-2,5-dione, 2-hydroxy-3a,4,7,7a-tetrahydro-1H-isoindol-1,3(2H)-dione, 2-hydroxyhexahydro-1H-isoindol-1,3(2H)-dione and 4-hydroxy-4-azatricyclo[5.2.1.0$^{2,6}$]dec-8-ene-3,5-dione, allowing a carbonylating agent selected from the group consisting of phosgene, diphosgene and triphosgene to act on the resultant compound to obtain a compound represented by the following Formula (II):

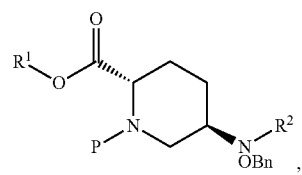

removing the protecting group P and treating the resultant compound with a base to produce a compound represented by the following Formula (III):

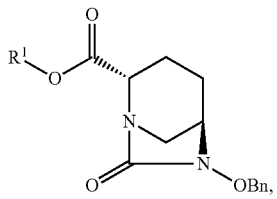

wherein in said Formulas (I), (II) and (III), OBn is benzyloxy; P is an NH protecting group capable of being removed with an acid; R$^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl or 3,5-dioxo-4-azatricyclo[5.2.1.0$^{2,6}$]dec-8-en-4-yl and R$^2$ is hydrogen, ClCO— or Cl$_3$COCO—.

2. The process according to claim 1, wherein P is tert-butoxycarbonyl.

3. The process according to claim 1, wherein R$^1$ is 2,5-dioxopyrrolidin-1-yl.

4. The process according to claim 1, wherein R$^1$ is 1,3-dioxo-3a,4,7,7a-tetrahydro-1H-isoindol-2(3H)-yl.

5. The process according to claim 1, wherein R$^1$ is 1,3-dioxohexahydro-1H-isoindol-2(3H)-yl.

6. The process according to claim 1, wherein R$^1$ is 3,5-dioxo-4-azatricyclo[5.2.1.0$^{2,6}$] dec-8-en-4-yl.

7. A process for producing a compound represented by a Formula (III), comprising: allowing a carbonylating agent selected from the group consisting of phosgene, diphosgene and triphosgene to act on a compound represented by the following Formula (II):

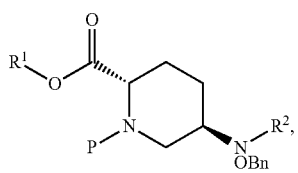

II removing the protecting group P and treating the resultant compound with a base to produce the compound represented by the following Formula (III):

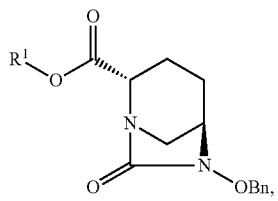

III wherein in said Formulas (II) and (III), OBn is benzyloxy; P is an NH protecting group capable of being removed with an acid; R$^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl or 3,5-dioxo-4-azatricyclo[5.2.1.0$^{2,6}$]dec-8-en-4-yl and R$^2$ is hydrogen.

8. The process according to claim 7, wherein P is tert-butoxycarbonyl.

9. The process according to claim 7, wherein R$^1$ is 2,5-dioxopyrrolidin-1-yl.

10. The process according to claim 7, wherein R$^1$ is 1,3-dioxo-3a,4,7,7a-tetrahydro-1H-isoindol-2(3H)-yl.

11. The process according to claim 7, wherein R$^1$ is 1,3-dioxohexahydro-1H-isoindol-2(3H)-yl.

12. The process according to claim 7, wherein R$^1$ is 3,5-dioxo-4-azatricyclo[5.2.1.0$^{2,6}$] dec-8-en-4-yl.

* * * * *

UNITED STATES PATENT AND TRADEMARK OFFICE
CERTIFICATE OF CORRECTION

PATENT NO. : 10,000,492 B2
APPLICATION NO. : 15/613620
DATED : June 19, 2018
INVENTOR(S) : Takao Abe et al.

Page 1 of 9

It is certified that error appears in the above-identified patent and that said Letters Patent is hereby corrected as shown below:

On the Title Page

Column 1, item (*), Line 3, after "0 days." delete "days.".

In the Specification

Column 6, Line 66, delete "1-hydroxypyrrolidin-2,5-dione," and insert --1-hydroxypyrrolidine-2,5-dione,--.

Column 9, Line 61, delete "1-hydroxypyrrolidin-2,5-dione," and insert --1-hydroxypyrrolidine-2,5-dione,--.

Column 11, Line 9, delete "2,5-dioxypyrrolidin-1-yl." and insert --2,5-dioxopyrrolidin-1-yl.--.

Column 16, Line 34, delete "9-fluororenylmethoxycarbonyl" and insert --9-fluorenylmethoxycarbonyl--.

Column 17, Line 36, delete "amino) piperidine" and insert --amino)piperidine--.

Column 18, Line 6, delete "amino) piperidine" and insert --amino)piperidine--.

Column 18, Line 58, delete "diazabicyclo [3.2.1]" and insert --diazabicyclo[3.2.1]--.

Column 20, Line 52, delete "[3.2.1] octane" and insert --[3.2.1]octane--.

Column 20, Line 54, delete "oct-2-yl] carbonyl}" and insert --oct-2-yl]carbonyl}--.

Column 20, Line 57, delete "[3.2.1] oct-2-yl]"" and insert --[3.2.1]oct-2-yl]--.

Column 20, Line 60, delete "[3.2.1] oct-2-yl]"" and insert --[3.2.1]oct-2-yl]--.

Signed and Sealed this
Thirteenth Day of November, 2018

Andrei Iancu
*Director of the United States Patent and Trademark Office*

CERTIFICATE OF CORRECTION (continued)
U.S. Pat. No. 10,000,492 B2

Column 20, Line 63, delete "oct-2-yl] carbonyl}" and insert --oct-2-yl]carbonyl}--.

Column 20, Line 66, delete "oct-2-yl] carbonyl}" and insert --oct-2-yl]carbonyl}--.

Column 21, Line 4, delete "oct-2-yl] carbonyl}" and insert --oct-2-yl]carbonyl}--.

Column 21, Line 7, delete "oct-2-yl] carbonyl}" and insert --oct-2-yl]carbonyl}--.

Column 21, Line 11, delete "oct-2-yl] carbonyl}" and insert --oct-2-yl]carbonyl}--.

Column 21, Line 14, delete "oct-2-yl] carbonyl}" and insert --oct-2-yl]carbonyl}--.

Column 21, Line 17, delete "[3.2.1] octan-7-one;" and insert --[3.2.1]octan-7-one;--.

Column 21, Line 19, delete "[3.2.1] octan-7-one;" and insert --[3.2.1]octan-7-one;--.

Column 21, Line 23, delete "amino) oxy]" and insert --amino)oxy]--.

Column 21, Line 26, delete "oct-2-yl] carbonyl}" and insert --oct-2-yl]carbonyl}--.

Column 21, Line 32, delete "oct-2-yl] carbonyl}" and insert --oct-2-yl]carbonyl}--.

Column 21, Line 38, delete "oct-2-yl] carbonyl}" and insert --oct-2-yl]carbonyl}--.

Column 21, Line 42, delete "oct-2-yl] carbonyl}" and insert --oct-2-yl]carbonyl}--.

Column 21, Line 45, delete "oct-2-yl] carbonyl}" and insert --oct-2-yl]carbonyl}--.

Column 21, Line 48, delete "oct-2-yl] carbonyl}" and insert --oct-2-yl]carbonyl}--.

Column 21, Line 51, delete "oct-2-yl] carbonyl}" and insert --oct-2-yl]carbonyl}--.

Column 21, Line 57, delete "oct-2-yl] carbonyl}" and insert --oct-2-yl]carbonyl}--.

Column 21, Line 60, delete "oct-2-yl] carbonyl}" and insert --oct-2-yl]carbonyl}--.

Column 22, Line 2, delete "oct-2-yl] carbonyl}" and insert --oct-2-yl]carbonyl}--.

Column 22, Line 7, delete "oct-2-yl] carbonyl}" and insert --oct-2-yl]carbonyl}--.

Column 22, Line 17, delete "[3.2.1] octane" and insert --[3.2.1]octane--.

Column 22, Line 21, delete "oct-2-yl] carbonyl}" and insert --oct-2-yl]carbonyl}--.

Column 22, Line 24, delete "oct-2-yl] carbonyl}" and insert --oct-2-yl]carbonyl}--.

Column 22, Line 27, delete "oct-2-yl] carbonyl}" and insert --oct-2-yl]carbonyl}--.

Column 22, Line 29, delete "[3.2.1] oct-2-yl]" and insert --[3.2.1]oct-2-yl]--.

Column 22, Line 32, delete "oct-2-yl] carbonyl}" and insert --oct-2-yl]carbonyl}--.

Column 22, Line 37, delete "oct-2-yl] carbonyl}" and insert --oct-2-yl]carbonyl}--.

Column 22, Line 40, delete "oct-2-yl] carbonyl}" and insert --oct-2-yl]carbonyl}--.

Column 22, Line 43, delete "oct-2-yl] carbonyl}" and insert --oct-2-yl]carbonyl}--.

Column 22, Line 46, delete "oct-2-yl] carbonyl}" and insert --oct-2-yl]carbonyl}--.

Column 22, Line 49, delete "oct-2-yl] carbonyl}" and insert --oct-2-yl]carbonyl}--.

Column 22, Line 52, delete "oct-2-yl] carbonyl}" and insert --oct-2-yl]carbonyl}--.

Column 22, Line 58, delete "oct-2-yl] carbonyl}" and insert --oct-2-yl]carbonyl}--.

Column 22, Line 62, delete "oct-2-yl] carbonyl}" and insert --oct-2-yl]carbonyl}--.

Column 22, Line 65, delete "oct-2-yl] carbonyl}" and insert --oct-2-yl]carbonyl}--.

Column 26, Line 58, delete "propylphosphonic" and insert --propylphosphoric--.

Column 30, Line 13, delete "(2) dihydrochloride" and insert --(2)dihydrochloride--.

Column 31, Line 53, delete "(2) dihydrochloride" and insert --(2)dihydrochloride--.

Column 33, Line 48, delete "oct-2-yl] carbonyl}" and insert --oct-2-yl]carbonyl}--.

Column 34, Line 18, delete "oct-2-yl] carbonyl}" and insert --oct-2-yl]carbonyl}--.

Column 34, Line 21, delete "diazabicyclo [3.2.1]" and insert --diazabicyclo[3.2.1]--.

Column 34, Line 41, delete "diazabicyclo [3.2.1]" and insert --diazabicyclo[3.2.1]--.

Column 35, Line 44, delete "oct-2-yl] carbonyl}" and insert --oct-2-yl]carbonyl}--.

Column 36, Line 38, delete "oct-2-yl] carbonyl}" and insert --oct-2-yl]carbonyl}--.

Column 37, Line 17, delete "oct-2-yl] carbonyl}" and insert --oct-2-yl]carbonyl}--.

Column 37, Line 21, delete "oct-2-yl] carbonyl}" and insert --oct-2-yl]carbonyl}--.

Column 37, Line 41, delete "oct-2-yl] carbonyl}" and insert --oct-2-yl]carbonyl}--.

Column 37, Line 59, delete "oct-2-yl] carbonyl}" and insert --oct-2-yl]carbonyl}--.

Column 38, Line 35, delete "diazabicyclo [3.2.1]" and insert --diazabicyclo[3.2.1]--.

Column 38, Line 42, delete "oct-2-yl] carbonyl}" and insert --oct-2-yl]carbonyl}--.

Column 39, Line 7, delete "oct-2-yl] carbonyl}" and insert --oct-2-yl]carbonyl}--.

Column 39, Line 21, delete "diazabicyclo [3.2.1]" and insert --diazabicyclo[3.2.1]--.

Column 40, Line 11, delete "oil. (yield 40%)" and insert --oil (yield 40%).--.

Column 41, Line 55, delete "[3.2.1] oct-2-yl]" and insert --[3.2.1]oct-2-yl]--.

Column 42, Line 48, delete "[3.2.1] octane" and insert --[3.2.1]octane--.

Column 42, Line 55, delete "oct-2-yl] carbonyl}" and insert --oct-2-yl]carbonyl}--.

Column 43, Line 8, delete "oct-2-yl] carbonyl}" and insert --oct-2-yl]carbonyl}--.

Column 43, Line 23, delete "[3.2.1] octane" and insert --[3.2.1]octane--.

Column 44, Line 31, delete "1-car boxylate" and insert --1-carboxylate--.

Column 46, Line 20, delete "diazabicyclo [3.2.1]" and insert --diazabicyclo[3.2.1]--.

Column 47, Line 45, delete "[3.2.1] octane" and insert --[3.2.1]octane--.

Column 47, Line 53, delete "oct-2-yl] carbonyl}" and insert --oct-2-yl]carbonyl}--.

Column 48, Line 4, delete "oct-2-yl] carbonyl}" and insert --oct-2-yl]carbonyl}--.

Column 48, Line 20, delete "[3.2.1] octane" and insert --[3.2.1]octane--.

Column 49, Line 4, delete ") carbonyl)" and insert --)carbonyl)--.

Column 49, Line 51, delete "[3.2.1] octane" and insert --[3.2.1]octane--.

Column 54, Line 46, delete "1H" and insert --$^1$H--.

Column 55, Line 12, delete "1H" and insert --$^1$H--.

Column 57, Line 4, delete "amino) piperidine" and insert --amino)piperidine--.

Column 59, Line 31, delete "amino) piperidine" and insert --amino)piperidine--.

Column 60, Line 9, delete "amino) piperidine" and insert --amino)piperidine--.

Column 62, Line 5, delete "amino) piperidine" and insert --amino)piperidine--.

Column 62, Line 34, delete "drired" and insert --dried--.

Column 63, Line 29, delete "carbonyl) piperidine" and insert --carbonyl)piperidine--.

Column 64, Line 4, delete ") carbonyl)" and insert --)carbonyl)--.

Column 67, Line 4, delete "carbonyl) piperidine" and insert --carbonyl)piperidine--.

Column 67, Line 49, delete ") carbonyl)" and insert --)carbonyl)--.

Column 68, Line 28, delete "carbonyl) piperidine" and insert --carbonyl)piperidine--.

Column 69, Line 4, delete "carbonyl) piperidine" and insert --carbonyl)piperidine--.

Column 69, Line 41, delete ") carbonyl)" and insert --)carbonyl)--.

Column 69, Line 62, delete "Subsequenty." and insert --Subsequently,--.

Column 70, Line 53, delete ") carbonyl)" and insert --)carbonyl)--.

Column 71, Line 28, delete "amino) piperidine" and insert --amino)piperidine--.

Column 73, Line 30, delete "amino) piperidine" and insert --amino)piperidine--.

Column 74, Line 24, delete "amino) piperidine" and insert --amino)piperidine--.

Column 74, Line 42, delete "amino) piperidine" and insert --amino)piperidine--.

Column 74, Lines 43 to 44, delete "amino) piperidine" and insert --amino)piperidine--.

Column 75, Line 47, delete "amino) piperidine" and insert --amino)piperidine--.

Column 75, Lines 48 to 49, delete "amino) piperidine" and insert --amino)piperidine--.

Column 77, Line 57, delete "amino) piperidine" and insert --amino)piperidine--.

Column 78, Line 43, delete ") carbonyl)" and insert --)carbonyl)--.

Column 78, Line 61, delete "amino) piperidine" and insert --amino)piperidine--.

Column 79, Line 57, delete "amino) piperidine" and insert --amino)piperidine--.

Column 79, Line 60, delete "amino) piperidine" and insert --amino)piperidine--.

Column 80, Line 17, delete "diazabicyclo [3.2.1]" and insert --diazabicyclo[3.2.1]--.

Column 80, Line 34, after "[M+H]$^+$" insert --.--.

Column 80, Line 37, delete "diazabicyclo [3.2.1]" and insert --diazabicyclo[3.2.1]--.

Column 80, Line 60, delete ") carbonyl)" and insert --)carbonyl)--.

Column 80, Line 67, delete "amino) piperidine" and insert --amino)piperidine--.

Column 81, Line 29, delete "diazabicyclo [3.2.1]" and insert --diazabicyclo[3.2.1]--.

Column 81, Line 45, after "[M+H]$^+$" insert --.--.

Column 82, Line 5, delete ") carbonyl)" and insert --)carbonyl)--.

Column 82, Line 27, delete "amino) piperidine" and insert --amino)piperidine--.

Column 83, Line 24, delete ") carbonyl)" and insert --)carbonyl)--.

Column 84, Line 12, delete "[3.2.1] octane" and insert --[3.2.1]octane--.

Column 84, Line 64, delete "[3.2.1] octane" and insert --[3.2.1]octane--.

Column 85, Line 21, delete "[3.2.1] octane" and insert --[3.2.1]octane--.

Column 85, Line 45, delete "amino) piperidine" and insert --amino)piperidine--.

Column 85, Line 47, delete "amino) piperidine" and insert --amino)piperidine--.

Column 85, Line 60, delete ") carbonyl)" and insert --)carbonyl)--.

Column 86, Line 9, delete "diazabicyclo [3.2.1]" and insert --diazabicyclo[3.2.1]--.

Column 86, Line 34, delete "[3.2.1] octane" and insert --[3.2.1]octane--.

Column 86, Line 60, delete "amino) piperidine" and insert --amino)piperidine--.

Column 87, Line 19, delete "[3.2.1] octane" and insert --[3.2.1]octane--.

Column 87, Line 40, delete "[3.2.1] octane" and insert --[3.2.1]octane--.

Column 87, Line 60, delete ") carbonyl)" and insert --)carbonyl)--.

Column 88, Line 46, after "[M+H]$^+$" insert --.--.

Column 88, Line 51, delete "[3.2.1] octane" and insert --[3.2.1]octane--.

Column 89, Line 8, delete "amino) piperidine" and insert --amino)piperidine--.

Column 89, Line 12, delete "amino) piperidine" and insert --amino)piperidine--.

Column 89, Line 46, delete "[3.2.1] octane" and insert --[3.2.1]octane--.

Column 89, Line 67, after "[M+H]$^+$" insert --.--.

Column 90, Line 32, delete "carbonyl) piperidine" and insert --carbonyl)piperidine--.

Column 90, Line 44, delete ") oxy)" and insert --)oxy)--.

Column 91, Line 38, delete ") carbonyl)" and insert --)carbonyl)--.

Column 91, Line 50, delete ") carbonyl)" and insert --)carbonyl)--.

Column 91, Line 51, delete "(benzyloxy)((3R,6S)" and insert --benzyloxy) ((3R,6S)--.

Column 92, Line 11, delete "3H),3.09" and insert --3H), 3.09--.

Column 93, Line 60, delete "carbonyl) piperidine" and insert --carbonyl)piperidine--.

Column 94, Line 4, delete ") carbonyl)" and insert --)carbonyl)--.

Column 94, Line 39, delete "[3.2.1] octane" and insert --[3.2.1]octane--.

Column 94, Line 67, delete ") carbonyl)" and insert --)carbonyl)--.

Column 95, Line 29, delete "[3.2.1] octane" and insert --[3.2.1]octane--.

Column 96, Line 12, delete "carbonyl) piperidine" and insert --carbonyl)piperidine--.

Column 96, Line 44, delete "[3.2.1] octane" and insert --[3.2.1]octane--.

Column 97, Line 31, delete "carbonyl) piperidine" and insert --carbonyl)piperidine--.

Column 98, Line 14, delete "[3.2.1] octane" and insert --[3.2.1]octane--.

Column 98, Lines 36 to 37, delete "carbonyl) piperidine" and insert --carbonyl)piperidine--.

CERTIFICATE OF CORRECTION (continued)
U.S. Pat. No. 10,000,492 B2

Column 98, Line 39, delete ") carbonyl)" and insert --)carbonyl)--.

Column 98, Line 64, delete "[3.2.1] octane" and insert --[3.2.1]octane--.

Column 99, Line 48, delete ") carbonyl)" and insert --)carbonyl)--.

Column 100, Line 60, delete ") carbonyl)" and insert --)carbonyl)--.

Column 101, Line 40, delete "[3.2.1] octane" and insert --[3.2.1]octane--.

Column 101, Line 64, delete "amino) piperidine" and insert --amino)piperidine--.

Column 101, Line 67, delete "amino) piperidine" and insert --amino)piperidine--.

Column 102, Line 14, delete ") carbonyl)" and insert --)carbonyl)--.

Column 102, Line 29, delete "diazabicyclo [3.2.1]" and insert --diazabicyclo[3.2.1]--.

Column 102, Line 50, delete "diazabicyclo [3.2.1]" and insert --diazabicyclo[3.2.1]--.

Column 103, Line 28, delete "diazabicyclo [3.2.1]" and insert --diazabicyclo[3.2.1]--.

Column 106, Line 8, delete "presssure," and insert --pressure,--.

Column 106, Line 9, delete "carreid" and insert --carried--.

Column 106, Line 43, delete "2-43aR,7aS)" and insert --2-((3aR,7aS)--.

Column 110, Line 49, delete "amino) piperidine" and insert --amino)piperidine--.

Column 113, Line 13, delete "diazabicyclo [3.2.1]" and insert --diazabicyclo[3.2.1]--.

Column 114, Line 24, delete "[3.2.1] octane" and insert --[3.2.1]octane--.

Column 114, Line 64, delete "[3.2.1] octane" and insert --[3.2.1]octane--.

Column 115, Line 38, delete "diazabicyclo [3.2.1]" and insert --diazabicyclo[3.2.1]--.

Column 116, Line 12, delete "diazabicyclo [3.2.1]" and insert --diazabicyclo[3.2.1]--.

Column 118, Line 35, delete "[3.2.1] octane" and insert --[3.2.1]octane--.

Column 119, Line 12, delete "diazabicyclo [3.2.1]" and insert --diazabicyclo[3.2.1]--.

Column 120, Line 57, delete "diazabicyclo [3.2.1]" and insert --diazabicyclo[3.2.1]--.

Column 122, Line 53, delete "oct-2-yl] carbonyl}" and insert --oct-2-yl]carbonyl}--.

Column 123, Line 12, delete "diazabicyclo [3.2.1]" and insert --diazabicyclo[3.2.1]--.

Column 125, Line 9, delete "oct-2-yl] carbonyl}" and insert --oct-2-yl]carbonyl}--.

Column 125, Line 53, delete "oct-2-yl] carbonyl}" and insert --oct-2-yl]carbonyl}--.

Column 127, Line 45, delete "oct-2-yl] carbonyl}" and insert --oct-2-yl]carbonyl}--.